США010662177B2

(12) United States Patent
Talukdar et al.

(10) Patent No.: US 10,662,177 B2
(45) Date of Patent: May 26, 2020

(54) BLOCKING TOLL-LIKE RECEPTOR 9 SIGNALING WITH SMALL MOLECULE ANTAGONIST

(71) Applicant: Council of Scientific & Industrial Research, New Delhi (IN)

(72) Inventors: Arindam Talukdar, Jadavpur (IN); Dipyaman Ganguly, Jadavpur (IN); Barnali Paul, Jadavpur (IN); Ayan Mukherjee, Jadavpur (IN); Shounak Roy, Jadavpur (IN); Swarnali Roy, Jadavpur (IN); Amrit Raj Ghosh, Jadavpur (IN); Roopkatha Bhattacharya, Jadavpur (IN); Oindrila Rahaman, Jadavpur (IN); Biswajit Kundu, Jadavpur (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/086,926

(22) PCT Filed: Mar. 21, 2017

(86) PCT No.: PCT/IN2017/050103
§ 371 (c)(1),
(2) Date: Sep. 20, 2018

(87) PCT Pub. No.: WO2017/163264
PCT Pub. Date: Sep. 28, 2017

(65) Prior Publication Data
US 2019/0092758 A1 Mar. 28, 2019

(30) Foreign Application Priority Data
Mar. 21, 2016 (IN) .............................. 201611009670

(51) Int. Cl.
| C07D 403/04 | (2006.01) |
| C07D 403/12 | (2006.01) |
| C07D 401/12 | (2006.01) |
| C07D 239/95 | (2006.01) |
| A61P 37/04  | (2006.01) |
| C07D 403/14 | (2006.01) |

(52) U.S. Cl.
CPC ............ *C07D 403/12* (2013.01); *A61P 37/04* (2018.01); *C07D 239/95* (2013.01); *C07D 401/12* (2013.01); *C07D 403/04* (2013.01); *C07D 403/14* (2013.01)

(58) Field of Classification Search
CPC .......................... C07D 403/04; C07D 403/14
See application file for complete search history.

(56) References Cited

U.S. PATENT DOCUMENTS

| 6,156,758 A  * | 12/2000 | Kung ................... C07D 401/04 514/252.14 |
| 6,221,882 B1   | 4/2001  | Macfarlane |
| 6,472,391 B2 * | 10/2002 | Matsuno ............... A61K 31/496 514/243 |
| 6,479,504 B1   | 11/2002 | Macfarlane et al. |
| 6,750,218 B2 * | 6/2004  | Matsuno ............... A61K 31/496 514/248 |
| 7,410,975 B2   | 8/2008  | Lipford et al. |

(Continued)

FOREIGN PATENT DOCUMENTS

| JP | 2000281660 A | 10/2000 |
| WO | 03103586 A2 | 12/2003 |

(Continued)

OTHER PUBLICATIONS

B. Paul et al., 159 European Journal of Medicinal Chemistry, 187-205 (2018) (Year: 2018).*

(Continued)

*Primary Examiner* — Alexander R Pagano
(74) *Attorney, Agent, or Firm* — Dinsmore & Shohl, LLP

(57) ABSTRACT

The present invention relates to small molecule 4-(piperazin-1-yl)quinazolin-2-amino compounds with formula (I) useful for inhibiting signalling by certain toll-like receptors (TLRs), especially TLR9. Toll-like receptors (TLRs) are members of the larger family of evolutionarily conserved pattern recognition receptors which are critical first line of defense for self-nonself discrimination by the host immune response. Aberrant TLR9 activation is implicated in autoreactive inflammation in different autoimmune diseases. The invention depicts compounds with formula (I), composition and methods can be used in a number of clinical applications, including as pharmaceutical agents and methods for treating conditions involving unwanted immune activity due to TLR9 activation.

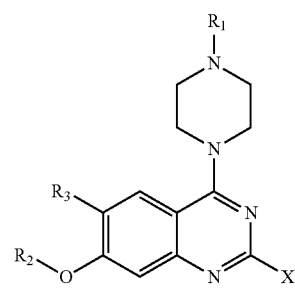

Formula (I)

17 Claims, 8 Drawing Sheets

(56) References Cited

U.S. PATENT DOCUMENTS

Figure 1:
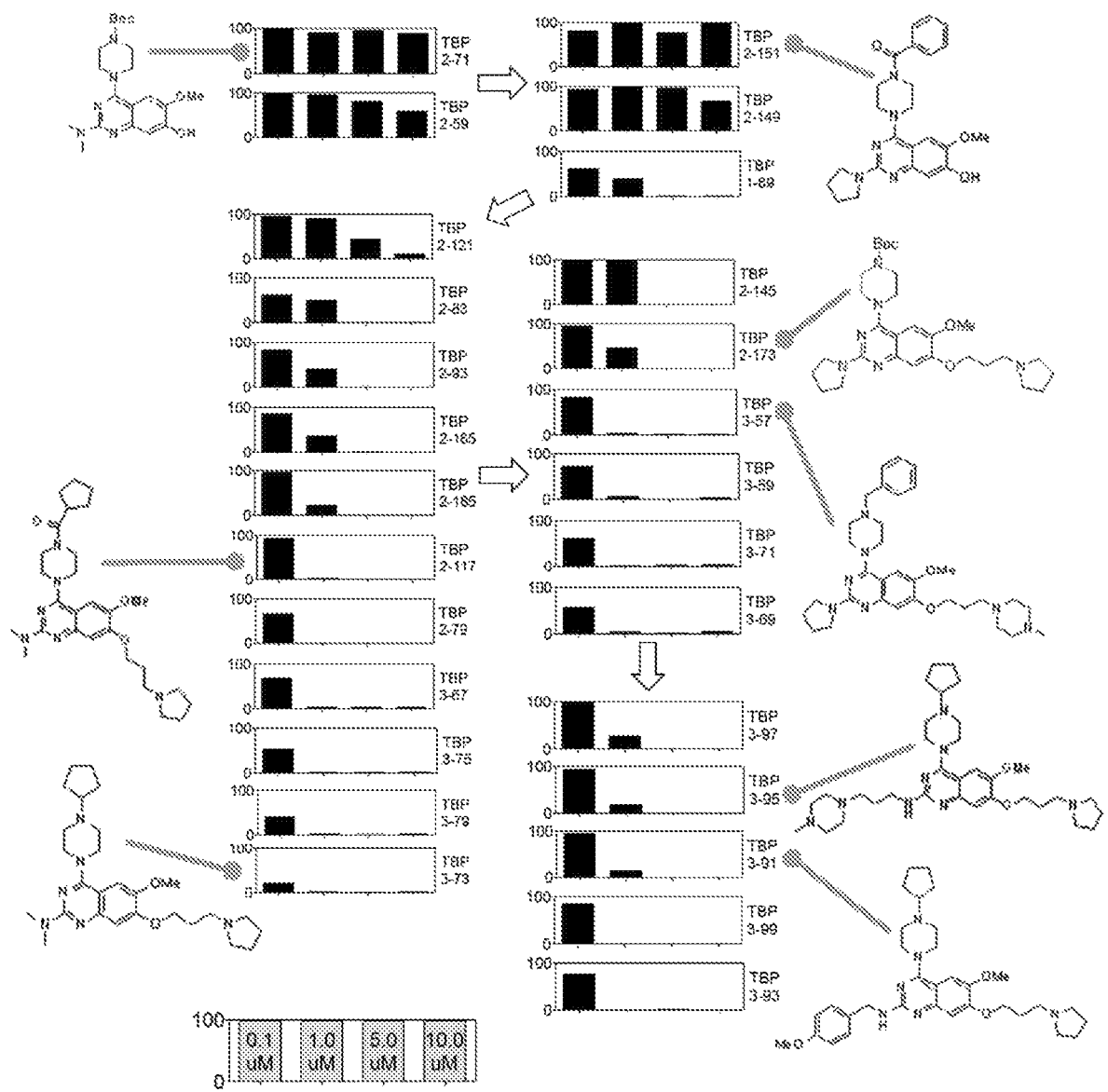

| | | | | |
|---|---|---|---|---|
| 8,044,068 B2* | 10/2011 | Okubo | ............... | C07D 401/12 514/314 |
| 8,999,988 B2* | 4/2015 | Hurley | ............... | C07D 403/14 514/252.16 |
| 2009/0099165 A1 | 4/2009 | Hurley et al. | | |

FOREIGN PATENT DOCUMENTS

| | | |
|---|---|---|
| WO | 2005007672 A2 | 1/2005 |
| WO | 2008030455 A2 | 3/2008 |
| WO | 2010036908 A1 | 4/2010 |

OTHER PUBLICATIONS

Takeda et al., "Toll-Like Receptors", Annu. Rev. Immunol, 2003, 21, pp. 335-376.

Alexopoulou et al., "Recognition of double-stranded RNA and activation of NF-KB by Toll-like receptor 3", Nature, 2001, vol. 413, pp. 732-738.

Bamboat et al., "Toll-Like Receptor 9 Inhibition Confers Protection from Liver Ischemia-Reperfusion Injury", Hepatology, 2010, 51(2), pp. 621-632.

Barrat et al., "Treatment of lupus-prone mice with a dual inhibitor of TLR7 and TLR 9 leads to reduction of autoantibody production and amelioration of disease symptoms", European Journal of Immunology, 2007, 37:, pp. 3582-3586.

Barton et al., "Intracellular localization of Toll-like receptor 9 prevents recognition of self DNA but facilitates access to viral DNA", Nature Immunology, 2006, vol. 7, No. 1, pp. 49-56.

Calcaterra et al., "Critical Role of TLR9 in Acute Graft-versus-Host Disease", The Journal of Immunology, 2008, vol. 181, No. 9, pp. 6132-6139.

Ganguly et al., "Self-RNA-antimicrobial peptide complexes activate human dendritic cells through TLR7 and TLR8", The Journal of Experimental Medicine, 2009, vol. 206, No. 9, pp. 1983-1994.

Ganguly et al., "The role of dendritic cells in autoimmunity", Nat Rev Immunol., 2013, vol. 13, No. 8, pp. 566-577.

Heil et al., "Species-Specific Recognition of Single-Stranded RNA via Toll-like Receptor 7 and 8", Science, 2004, vol. 303, No. 5663, pp. 1526-1529.

Hemmi et al., "A Toll-like receptor recognizes bacterial DNA", Nature, 2000, vol. 408, No. 6813, pp. 740-745.

Hoque et al., "TLR9 and the NLRP3 Inflammasome Link Acinar Cell Death With Inflammation in Acute Pancreatitis", Gastroenterology, 2011,vol. 141, No. 1, pp. 358-369; Author Manuscript, pp. 1-18.

Itagaki et al., "Bacterial DNA Induces Pulmonary Damage via TLR9 through Cross-Talk with Neutrophils", Shock, 2011, vol. 36, No. 6, pp. 548-552; Author Manuscript, pp. 1-12.

Lande et al., Plasmacytoid dendritic cells sense self-DNA coupled with antimicrobial peptide, Nature, 2007, vol. 449, pp. 564-571.

Lande et al., "Neutrophils Activate Plasmacytoid Dendritic Cells by Releasing Self-DNA-Peptide Complexes in Systemic Lupus Erythematosus", www.ScienceTranslationalMedicine.org, 2011, vol. 3, Issue 73, pp. 1-11; Research Article.

Leadbetter et al., "Chromatin-IgG complexes activate B cells by dual engagement of IgM and Toll-like receptors", Nature, 2002, vol. 416, No. 6881, pp. 603-607.

Lund et al., "Recognition of single-stranded RNA viruses by Toll-like receptor 7", ProcNatlAcadSci U.S.A., 2004, vol. 101, No. 15, pp. 5598-5603.

Marshak-Rothstein "Toll-like receptors in systemic autoimmune disease", Nature Reviews, Immunology, 2006, vol. 6, No. 11, pp. 823-835.

Medzhitov et a., "A human homologue of the *Drosophila* Toll protein signals activation of adaptive immunity", Nature, 1997, vol. 388, pp. 394-397.

Christensen et al., "Toll-like receptor 9 controls anti-DNA autoantibody production in murine lupus", The Journal of Experimental Medicine, 2005, vol. 202, No. 2, pp. 321-331.

Wallace, "The use of chloroquine and hydroxychloroquine for non-infectious conditions other than rheumatoid arthritis or lupus: a critical review", Lupus, 5 Suppl 1, 1996, pp. S59-S64.

Medzhitov, "Toll-Like Receptors and Innate Immunity", Nature Reviews Immunology, vol. 1, 2001, pp. 135-145.

International Search Report and Written Opinion, completed Aug. 9, 2017, pertaining to PCT/IN2017/050103, filed Mar. 21, 2017.

* cited by examiner

| MOLECULE ID | $IC_{50}$ (µM) |
|---|---|
| TBP 2-93 (13a) | 0.2820 |
| TBP-2-121 (13b) | 3.398 |
| TBP 2-117 (13c) | 0.6292 |
| TBP 3-79 (13d) | 0.07428 |
| TBP 3-73 (13e) | 0.01924 |
| TBP 3-75 (13f) | 0.02222 |
| TBP 3-67 (13g) | 0.1057 |
| TBP-3-113 (13h) | 0.03668 |
| TBP-2-173 (17a) | 1.012 |
| TBP-2-145 (17e) | 3.001 |
| TBP-3-69 (18b) | 0.02544 |
| TBP-2-185 (19) | 0.6272 |
| TBP-3-57 (20) | 0.08773 |
| TBP-3-59 (21a) | 0.1295 |
| TBP-3-71(21b) | 0.04707 |
| TBP-3-91 (25a) | 0.09100 |
| TBP-3-93 (25b) | 0.04142 |
| TBP-3-95 (25c) | 0.0939 |
| TBP-3-97 (25d) | 0.1886 |
| TBP-3-99 (25e) | 0.0176 |
| TBP-3-149 (27) | 0.09421 |
| TBP-4-11 (28a) | 0.1007 |
| TBP-3-155 (28b) | 5.145 |
| TBP-3-157 (28c) | 3.450 |

Fig. 5A (table 2)

| | |
|---|---|
| TBP-2-159 (29a) | 0.1197 |
| TBP-2-149 (30c) | 11.38 |
| TBP-3-135 (30a) | 8.802 |
| TBP-3-137 (30b) | 20.24 |
| TBP-2-151 (31) | 20.00 |
| TBP-3-123 (33) | 1.121 |
| TBP-3-145 (32b) | 32.15 |
| TBP-3-127 (34a) | 0.5690 |

Fig. 5B (table 2)

BLOCKING TOLL-LIKE RECEPTOR 9 SIGNALING WITH SMALL MOLECULE ANTAGONIST

FIELD OF INVENTION

The invention relates small molecule antagonist of compounds with formula (I) in free form or in acceptable salt form useful for altering immune function by blocking toll-like receptor 9 signalling.

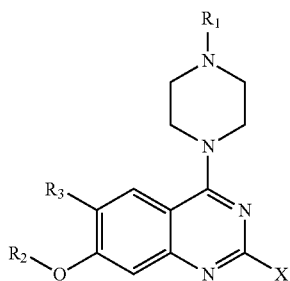

Formula (I)

BACKGROUND OF THE INVENTION

The innate immunity is comprised of several types of cells including dendritic cells (DC's), macrophages and monocytes, polymorphonuclear cells, natural killer (NK) cells, innate lymphoid cells and natural killer T cells (NKT cells) which detects various pathogens as well as aberrant host cells with potential for danger to tissue integrity through specialized receptors like toll-like receptors. Toll-like receptors (TLRs) are a family of germline-encoded cell surface pattern recognition molecules containing an pathogen binding ectodomain (ECD) with 19-25 leucine-rich repeats (LRRs), a transmembrane domain and a characteristic cytoplasmic domain called the TIR (Toll/IL-1 receptor) domain. TIR domain is responsible for downstream signalling, whereas LRRs containing 24-29 amino acids are responsible for ligand recognition and binding. TLRs get triggered in response to bacterial and fungal infections (Medzhitov, R; Nat. Rev. Immunol. 1, 135-145, 2001) followed by induction of downstream signalling, leading to expression of inflammatory genes like those of the nuclear factor-κB (NF-κB) family of transcription factors and antimicrobial peptides. There are 11 human and 12 mice TLRs have been identified which recognize different molecular patterns on the pathogens.

Major group of the TLRs are expressed on the cell surface. The leucine-rich repeats in the ectodomains of these molecules bind to unique molecular entities on pathogens (PAMPs), which detect and initiate responses to invading microorganisms (Akira, S; et al. Annu Rev Immunol. 21, 335-76, 2003). Another group of TLRs (endosomal TLRs) are located inside the cell within the endosomal-lysosomal compartments, instead of being expressed on the cell surface (Akira, S; et al. Annu Rev Immunol. 21, 335-76, 2003). This group comprises of TLR3 (Alexopoulou, L; et al. Nature, 413(6857), 732-8, 2001), TLR7 (Hemmi, H; et al. Nature, 408(6813), 740-5, 2001; Lund, J. M; et al. Proc Natl Acad Sci USA. 101(15), 5598-603, 2004), TLR8 (Heil, F; et al. Science, 303(5663), 1526-9, 2004) and TLR9 (Hemmi, H; et al. Nature, 408(6813), 740-5, 2001). The endosomal TLRs are specialized for detecting microbial nucleic acids after microbes get phagocytosed and reach the endosomal compartments.

The downstream signalling goes through recruitment of intracellular adaptor molecules such as Myd88 (or the myeloid differentiation primary-response gene 88), TIRAP (or the TIR-domain containing adaptor protein), TRIF (or the TIRAP inducing IFN-beta) and TRAM (or the TRIF-related adaptor molecule). TLR-adaptor molecule interactions in turn recruit other proteins to the signalling complex, which initiates multiple downstream signalling pathways, leading to activation of NFkB or mitogen-activated protein kinases (MAPKs) or recruitment of the IFN regulatory factors (IRFs). These different pathways in turn result in the transcription of genes encoding different cytokines, chemokines, co-stimulatory molecules or other proteins, thereby sculpting the ensuing immune response (Akira, S; et al. Annu Rev Immunol. 21, 335-76, 2003). The intracellular localization of the nucleic acid-recognizing TLRs (TLR3, 7, 8, 9) is one of the mechanisms that prevent their spontaneous activation by circulating host-derived nucleic acids (Barton, G. M; et al. Nat Immunol. 7(1):49-56, 2006), however under certain pathological conditions the endogenous nucleic acids can overcome this regulation. It has been previously shown by us and others that the circulating immune complexes found in sera of patients suffering from systemic lupus erythematosus (SLE) typically contain nucleic acids associated with various proteins such as antibodies, the chromatin-associated protein HMGB1, the antimicrobial peptide LL37, ribonuclear proteins and others (Lande, R; et al. Nature, 449(7162), 564-9, 2011; Ganguly, D. et al. Nat Rev Immunol. 13(8), 566-77, 2013). Our previous studies have also shown that TLR9, 7 and 8 activation driven by self nucleic acid and LL37 complexes may also play an important pathogenic role in Psoriasis (Lande, R; et al. Nature, 449(7162), 564-9, 2007; Ganguly, D. et al. J Exp Med. 206(9), 1983-94, 2009). These associated proteins may protect the bound nucleic acid from degradation and/or facilitate their entry into the cell, as is the case for Fc receptor-mediated uptake of antibody-nucleic acid complexes (Leadbetter, F. A; et al. Nature, 416(6881), 603-7, 2002; Ganguly, D. et al. J Exp Med. 206(9), 1983-94, 2009). Once inside the endolysosomal compartments, the nucleic acid cargo can then stimulate the intracellular TLRs, priming the immune system for a cascade of inflammation inciting cytotoxic and/or humoral response. For example, this cycle of innate immune recognition, generation of autoreactive antibodies, and consequent immune complex formation is believed to play critical role in the pathogenesis of SLE and possibly Sjogren's syndrome (Marshak-Rothstein, A; Nat Rev Immunol. 6(11), 823-35, 2006; Lande, R; et al. Nature, 449(7162), 564-9, 2011; Ganguly, D. et al. Nat Rev Immunol. 13(8), 566-77, 2013), a finding confirmed in animal models treated with TLR7 and TLR9-competitive antagonist oligonucleotides (Banat, F. J; et al. Eur J Immunol. 37(12), 3582-6, 2007; Christensen, S. R; et al. J Exp Med. 202(2), 321-31, 2005). TLR-mediated pathological responses to nucleic acids have also been shown to contribute to other pathologies like psoriasis (Lande R et al, Nature, 2007; Ganguly D et al, J Exp Med, 2009), ischemic liver injury (Bamboat, Z. M; et al. Hepatology, 51(2), 621-32, 2010) lung infection (Itagaki, K; et al. Shock, 36(6), 548-52, 2011), pancreatitis (Hogue, R; et al. Gastroenterology, 141(1), 358-69, 2011) and graft-versus-host disease (Calcaterra, C; et al. J Immunol. 181(9), 6132-9, 2008).

Hydroxychloroquine and chloroquine are not only used as anti-malarial agents but has been commonly prescribed to treat various clinical contexts of autoreactive inflammation (autoimmune diseases) such as rheumatoid arthritis (RA) and SLE (Wallace, D. J; *Lupus,* 5 Suppl 1, S59-64, 1996). In literature there are several reports of small molecule analogues and derivatives of chloroquine with substituted quinoline and quinazoline scaffold which can inhibit stimulation of the immune system. U.S. Pat. Nos. 6,221,882; 6,479,504; 7,410,975 B2; WO 2008/030455, published Mar. 13, 2008; U.S. Pat. No. 7,410,975 B2; PCT published application PCT/US03/17733 (WO 03/103586 A2); and PCT published application PCT/US2009/058401 (WO2010/036908).

OBJECTIVES OF THE INVENTION

The main object of the present invention is to provide compounds of general formula I. Another object of the present invention is to provide a screening method involving human peripheral blood mononuclear cells to screen compounds of general formula I against TLR9.

Yet another objective of the present invention is to provide a method for testing TLR9 antagonism of compounds of general formula I, in primary human plasmacytoid dendritic cells (pDCs) purified from human peripheral blood mononuclear cells.

Yet another objective of the present invention is to provide a method for testing TLR9 antagonism of compounds of general formula I a reporter assay method involving a cell line expressing TLR9 to screen compounds of general formula I for TLR9 antagonism.

Yet another objective of the present invention is to correlate the assays results involving human peripheral blood mononuclear cells, human primary pDCs and transfected TLR9 cells.

Yet another object of the present invention is to provide composition and methods of compounds of general formula I with TLR9 antagonistic activity that can modulate immune responses.

Yet another object of the present invention is to provide composition and methods of compounds of general formula I that can be used in a number of clinical applications, including as pharmaceutical agents and methods for treating conditions involving untoward immune hyperactivity.

Yet another object of the present invention is to provide composition and methods of compounds of general formula I without considerable cytotoxicity in HepG2 (a hepatic epithelial cell line) and SW480 (an intestinal mucosal epithelial cell line) cells at concentrations below 100 μM.

SUMMARY OF THE INVENTION

In an embodiment of the present invention, compounds of general formula I is provided.

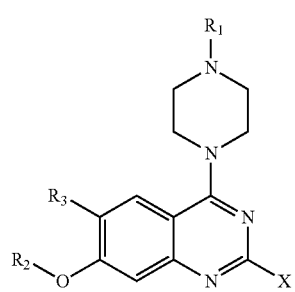

Formula (I)

wherein

X is independently selected from groups referred to as follows:

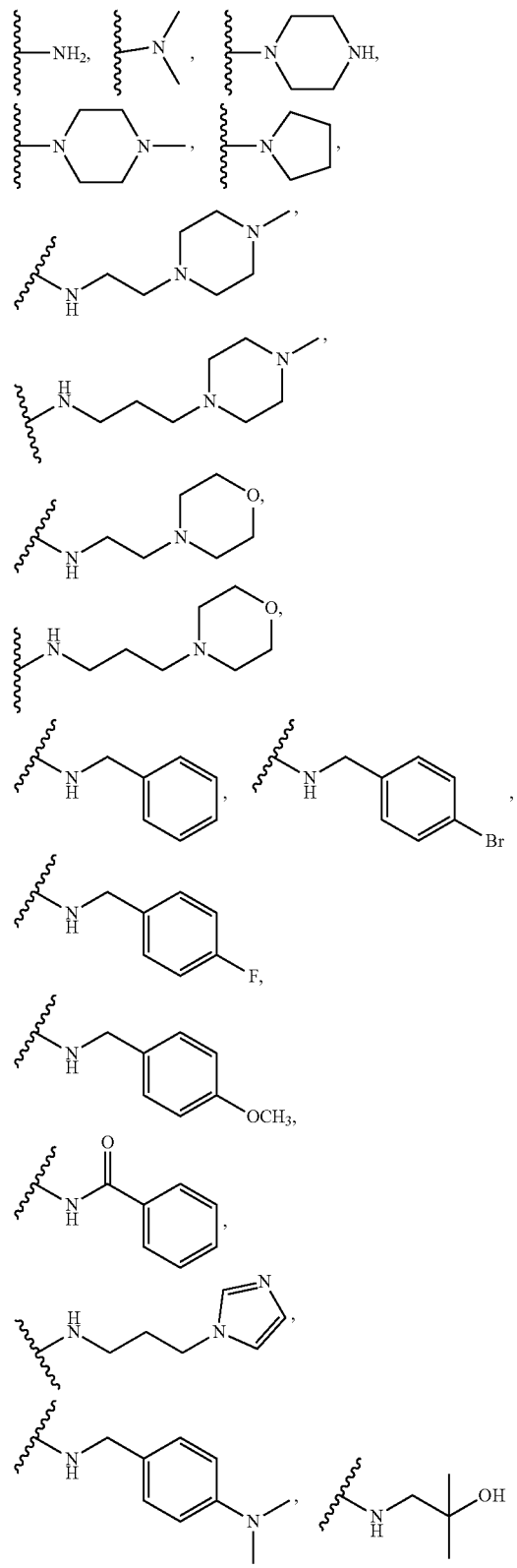

wherein R₁ is independently selected from groups referred to as follows:

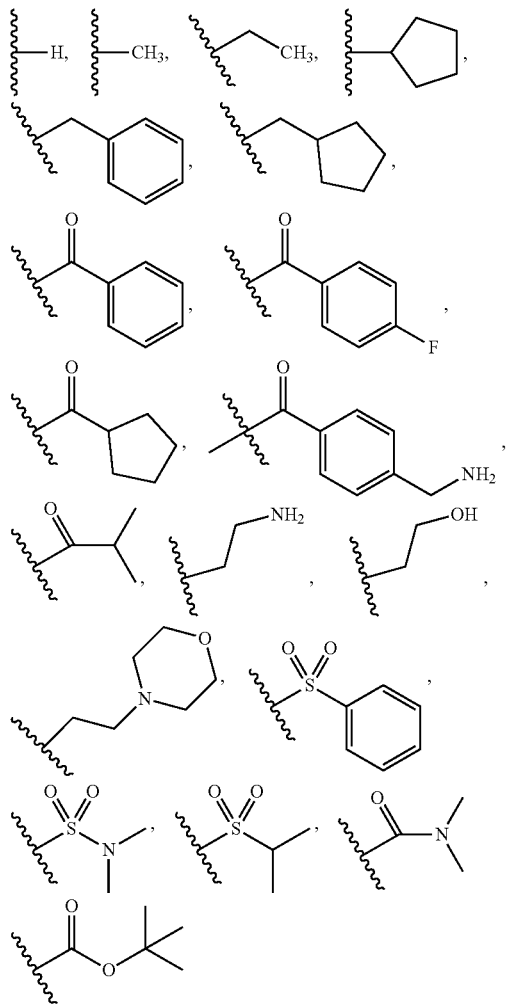

wherein R₂ is a group having structure

R2=H,

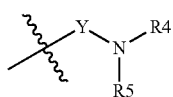

Where Y is optionally substituted or unsubstituted C₀ to C₃alkyl; R₅ and R₆ are independently hydrogen or substituted or unsubstituted alkyl or R₅ and R₆ is joined to form substituted or unsubstituted heterocycle.

wherein R₂ is independently selected from groups referred to as follows:

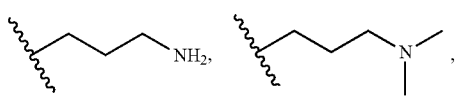

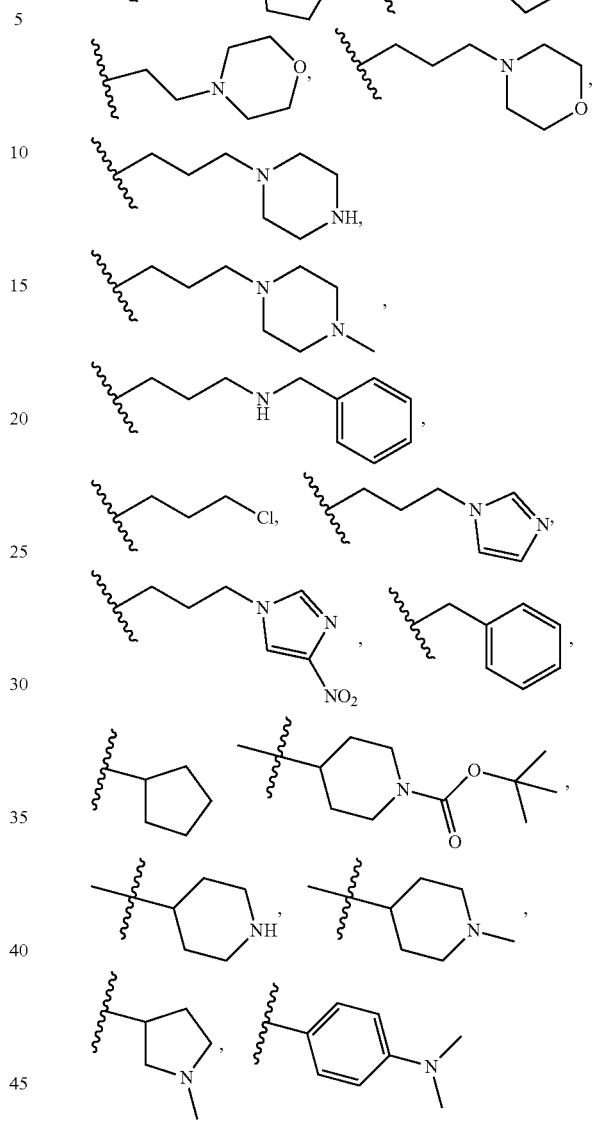

wherein R₃ is independently selected from groups referred to as hydrogen, —OH and —OCH₃ groups.

In another embodiment the compounds of general formula 1 is represented by compounds encompassing:

4-(4-(Isopropylsulfonyl)piperazin-1-yl)-6-methoxy-N,N-dimethyl-7-(3-(pyrrolidin-1-yl)propoxy)quinazolin-2-amine 13a (TBP-2-93);

4-(4-(Dimethylamino)-6-methoxy-7-(3-(pyrrolidin-1yl)propoxy)quinazolin-4-yl)-N,N-dimethylpiperazin-1-sulfonamide 13b (TBP-2-121);

Cyclopentyl(4-(2-(dimethylamino)-6-methoxy-7-(3-(pyrrolidin-1yl)propoxy)quinazolin-4-yl)piperazine-1yl)methanone 13c (TBP-2-117);

4-(4-(Cyclopentylmethyl)piperazin-1-yl)-6-methoxy-N,N-dimethyl-7-(3-(pyrrolidin-1yl)propoxy)quinazolin-2-amine 13d (TBP-3-79);

4-(4-(Cyclopentylpiperazin-1-yl)-6-methoxy-N,N-dimethyl-7-(3-(pyrrolidin-1yl)propoxy)quinazolin-2-amine 13e (TBP-3-73);

(4-(2-(Dimethylamino)-6-methoxy-7-(3-(pyrrolidin-1-yl)propoxy)quinazoline-4-yl)piperazin-1-yl)(phenyl)methanone 13f (TBP-3-75);

4-(4-Benzylpiperazin-1-yl)-6-methoxy-N,N-dimethyl-7-(3-(pyrrolidin-1-yl)propoxy)quinazolin-2-amine 13g (TBP-3-67);

(4-(Aminomethyl)phenyl)(4-(2-(dimethylamino)-6-methoxy-7-(3-(pyrrolidin-1-yl)propoxy)quinazolin-4-yl)piperazin-1-yl)methanone 13h (TBP-3-113);

6-((4-(4-(2-(Dimethylamino)-6-methoxy-7-(3-(pyrrolidin-1-yl)propoxy)quinazolin-4-yl)piperazine-1-carbonyl)benzyl)amino)-6-oxohexanoic acid 13i (TBP-3-115);

6-((4-(4-(2-(Dimethylamino)-6-methoxy-7-(3-(pyrrolidin-1-yl)propoxy)quinazolin-4-yl)piperazine-1-carbonyl)benzyl)amino)-6-oxohexanoic acid 13i (TBP-3-115);

2-(4-(2-(dimethylamino)-6-methoxy-7-(3-(pyrrolidin-1-yl)propoxy)quinazolin-4-yl)piperazin-1-yl)-1-(4-fluorophenyl)ethanone 13j (TBP-4-81);

t-Butyl-4-(6-methoxy-7-(3-morpholinpropoxy)-2-(pyrrolidin-1-yl)quinazoline-4-yl)piperazine-1-carboxylate 17a (TBP-2-173);

t-Butyl-4-(6-methoxy-7-(3-(4-methylpiperazin-1-yl)propoxy)-2-(pyrrolidin-1-yl)quinazoline-4-yl)piperazine-1-carboxylate 17b (TBP-2-189);

t-Butyl-4-(7-(3-(1H-imidazol-1-yl)propoxy)-6-methoxy-2-(pyrrolidin-1-yl)quinazolin-4-yl)piperazine-1-carboxylate 17c (TBP-2-191);

t-Butyl-4-(7-(3-(1H-imidazol-1-yl)propoxy)-6-methoxy-2-(pyrrolidin-1-yl)quinazoline-4-yl)piperazine-1-carboxylate 17d (TBP-3-47);

t-Butyl-4-(6-methoxy-2-(pyrrolidin-1-yl)-7-(3-(pyrrolidin-1-yl)propoxy)quinazolin-4-yl)piperazine-1-carboxylate 17e (TBP-2-145);

4-(3-(6-Methoxy-4-(piperazin-1-yl)-2-(pyrrolidin-1-yl)quinazolin-7-yloxy)propyl)morpholine 18a (TBP-2-179);

7-(3-(1H-Imidazol-1-yl)propoxy)-6-methoxy-4-(piperazin-1-yl)-2-(pyrrolidin-1-yl)quinazoline 18b (TBP-3-69);

3-((6-Methoxy-4-(piperazin-1-yl)-2-(pyrrolidin-1-yl)quinazolin-7-yl)oxy)-N,N-dimethylpropan-1-amine 18c (TBP-3-49);

4-(3-(6-Methoxy-4-(4-(phenylsulfonyl)piperazin-1-yl)-2-(pyrrolidin-1-yl)quinazolin-7-yloxy)propyl)morpholine 19 (TBP-2-185);

4-(4-Benzylpiperazin-1-yl)-6-methoxy-7-(3-(4-methylpiperazin-1-yl)propoxy)-2-(pyrrolidin-1-yl)quinazoline 20 (TBP-3-57);

3-(4-(4-Benzylpiperazin-1-yl)-6-methoxy-2-(pyrrolidin-1-yl)quinazolin-7-yloxy)-N,N-dimethylpropan-1-amine 21a (TBP-3-59);

(4-(7-(3-(Dimethylamino)propoxy)-6-methoxy-2-(pyrrolidin-1-yl)quinazolin-4-yl)piperazin-1-yl)(phenyl)methanone 21b (TBP-3-71);

4-(4-Cyclopentylpiperazin-1-yl)-6-methoxy-N-(4-methoxybenzyl)-7-(3-(pyrrolidin-1-yl)propoxy)quinazolin-2-amine 25a (TBP-3-91);

4-(4-Cyclopentylpiperazin-1-yl)-N-(4-fluorobenzyl)-6-methoxy-7-(3-(pyrrolidin-1-yl)propoxy)quinazolin-2-amine 25b (TBP-3-93);

4-(4-Cyclopentylpiperazin-1-yl)-6-methoxy-N-(3-(4-methylpiperazin-1-yl)propyl)-7-(3-(pyrrolidin-1-yl)propoxy)quinazolin-2-amine 25c (TBP-3-95);

N-(3-(1H-Imidazol-1-yl)propyl)-4-(4-cyclopentylpiperazin-1-yl)-6-methoxy-7-(3-(pyrrolidin-1-yl)propoxy)quinazolin-2-amine 25d (TBP-3-97);

4-(4-Cyclopentylpiperazin-1-yl)-6-methoxy-2-(4-methylpiperazin-1-yl)-7-(3-(pyrrolidin-1-yl)propoxy)quinazoline 25e (TBP-3-99);

7-(Cyclopentyloxy)-6-methoxy-N,N-dimethyl-4-(piperazin-1-yl)quinazolin-2-amine 27 (TBP-3-149);

7-(Cyclopentyloxy)-6-methoxy-N,N-dimethyl-4-(4-methylpiperazin-1-yl)quinazolin-2-amine 28a (TBP-4-11);

1-(4-(7-(Cyclopentyloxy)-2-(dimethylamino)-6-methoxyquinazolin-4-yl)piperazin-1-yl)-2-methylpropan-1-one 28b (TBP-3-155);

4-(7-(Cyclopentyloxy)-2-(dimethylamino)-6-methoxyquinazolin-4-yl)-N,N-dimethylpiperazine-1-carboxamide 28c (TBP-3-157);

6-methoxy-N,N-dimethyl-4-(4-methylpiperazin-1-yl)-7-(piperidin-4-yloxy)quinazolin-2-amine 28d (TBP-4-67);

6-methoxy-N,N-dimethyl-4-(4-methylpiperazin-1-yl)-7-((1-methylpiperidin-4-yl)oxy)quinazolin-2-amine 28e (TBP-4-69);

6-methoxy-N,N-dimethyl-4-(4-methylpiperazin-1-yl)-7-((1-methylpyrrolidin-3-yl)oxy)quinazolin-2-amine 28f (TBP-4-71);

7-(4-(dimethylamino)phenoxy)-6-methoxy-N,N-dimethyl-4-(4-methylpiperazin-1-yl)quinazolin-2-amine 28g (TBP-4-73);

4-(4-cyclopentylpiperazin-1-yl)-6-methoxy-N,N-dimethyl-7-(1-methylpiperidin-4-yloxy)quinazolin-2-amine 28h (TBP-4-77);

4-(4-cyclopentylpiperazin-1-yl)-6-methoxy-N,N-dimethyl-7-(1-methylpyrrolidin-3-yloxy)quinazolin-2-amine 28i (TBP-4-79);

7-(Benzyloxy)-6-methoxy-N,N-dimethyl-4-(piperazin-1-yl)quinazolin-2-amine 29a (TBP-2-159);

(4-(7-(Benzyloxy)-2-(dimethylamino)-6-methoxyquinazolin-4-yl)piperazin-1-yl)(phenyl)methanone 30a (TBP-3-135);

4-(7-(Benzyloxy)-2-(dimethylamino)-6-methoxyquinazolin-4-yl)-N,N-dimethylpiperazine-1-sulfonamide 30b (TBP-3-137);

7-(Benzyloxy)-6-methoxy-4-(piperazin-1-yl)-2-(pyrrolidin-1-yl)quinazoline 30c (TBP-2-149);

(4-(7-(Benzyloxy)-6-methoxy-2-(pyrrolidin-1-yl)quinazolin-4-yl)piperazin-1-yl)(phenyl)methanone 31 (TBP-2-151);

t-Butyl-4-(7-(benzyloxy)-6-methoxy-2-((4-methoxybenzyl)amino)quinazolin-4-yl)piperazine-1-carboxylate 32a (TBP-3-121);

t-Butyl-4-(7-(benzyloxy)-2-((2-hydroxy-2-methylpropyl)amino)-6-methoxyquinazolin-4-yl)piperazine-1-carboxylate 32b (TBP-3-145);

7-(Benzyloxy)-6-methoxy-2-(4-methoxyphenethyl)-4-(piperazin-1-yl)quinazoline 33 (TBP-3-123);

7-(Benzyloxy)-6-methoxy-2-(4-methoxyphenethyl)-4-(4-methylpiperazin-1-yl)quinazoline 34a (TBP-3-127);

(4-(7-(Benzyloxy)-6-methoxy-2-(4-methoxyphenethyl)quinazolin-4-yl)piperazin-1-yl)(phenyl)methanone 34b (TBP-3-139), tert-butyl 4-(2-(dimethylamino)-7-hydroxy-6-methoxyquinazolin-4-yl)piperazine-carboxylate 9 (TBP-2-71), 4-(4-cyclopentylpiperazin-1-yl)-2-(dimethylamino)-6-methoxyquinazolin-7-ol (TBP-4-75), tert-butyl 4-(7-hydroxy-6-methoxy-2-(pyrrolidin-1-yl)quinazolin-4-yl)piperazine-1-carboxylate 15 (TBP-2-135)

(4-(7-hydroxy-6-methoxy-2-(pyrrolidin-1-yl)quinazolin-4-yl)piperazin-1-yl)(phenyl)methanone (TBP-2-151), 2-(dimethylamino)-6-methoxy-4-(4-methylpiperazin-1-yl)quinazolin-7-ol (TBP-4-9), 2-(dimethylamino)-6-methoxy-4-(piperazin-1-yl)quinazolin-7-ol (TBP-2-169), tert-butyl 4-(2-(dimethylamino)-6-methoxy-7-(3-morpholinopropoxy)quinazolin-4-yl)piperazine-1-carboxylate (TBP-2-165), tert-butyl 4-(2-(dimethylamino)-6-methoxy-7-(3-(pyrrolidin-1-yl)propoxy)quinazolin-4-yl)piperazine-1-carboxylate 11 (TBP-2-79),
In another embodiment the structural formulae of general formula 1 is consisting the representative compounds:
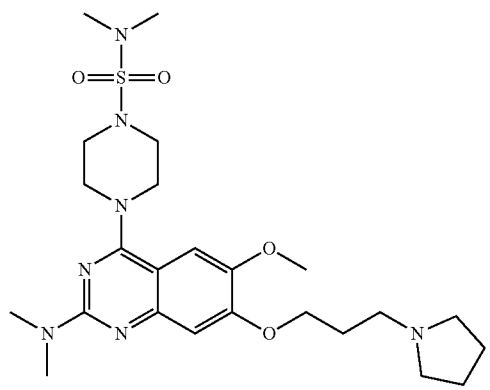
(TBP-2-93)
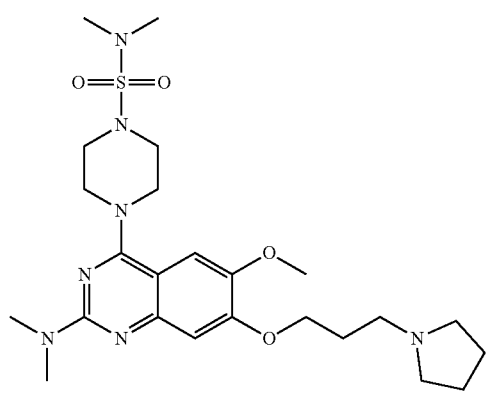
(TBP-2-121)
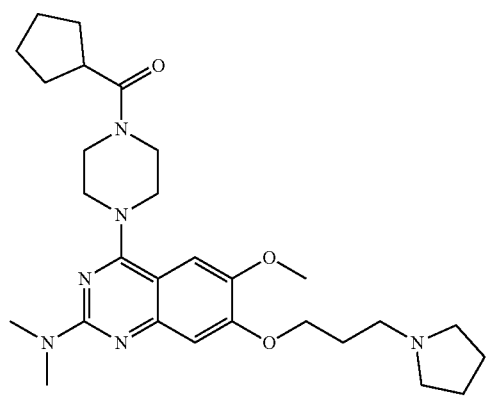
(TBP-2-117)
-continued
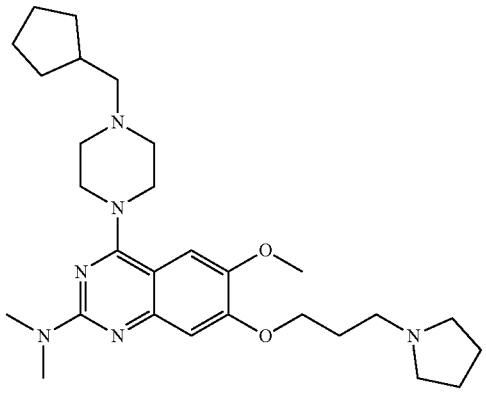
(TBP-3-79)
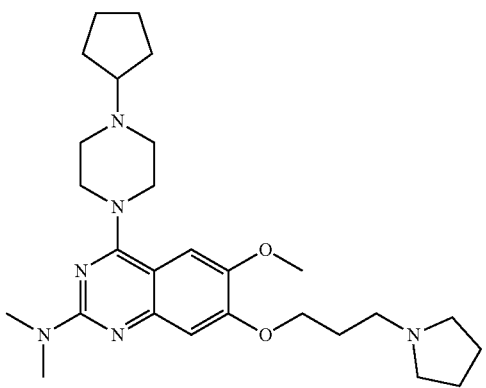
(TBP-3-73)
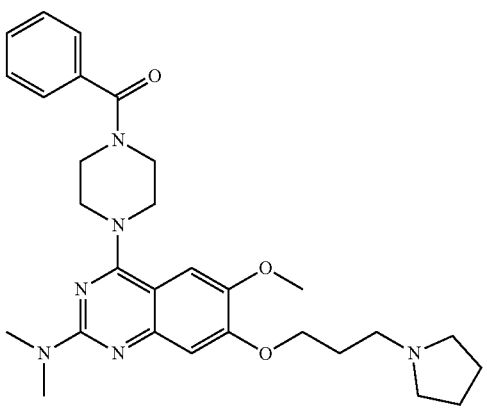
(TBP-3-75)

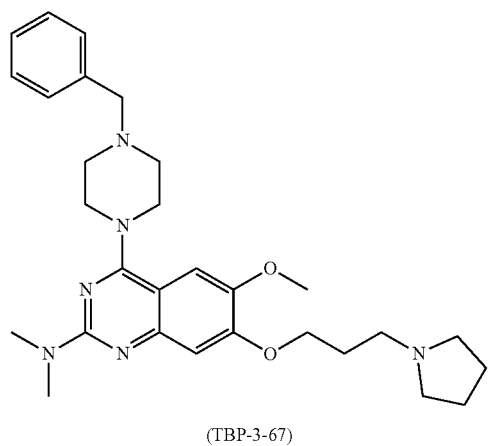
(TBP-3-67)
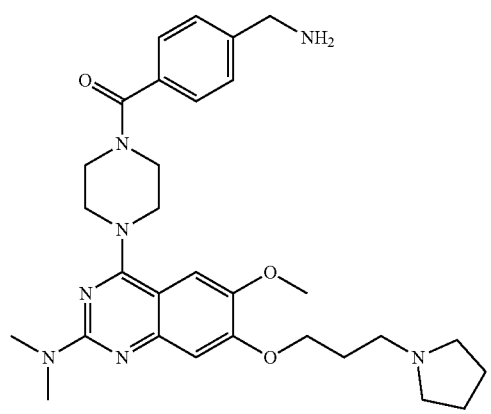
TBP-3-113
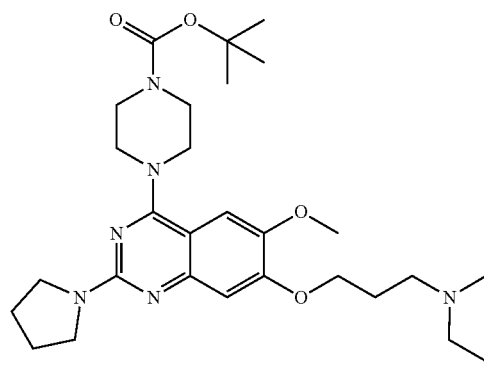
(TBP-2-173)
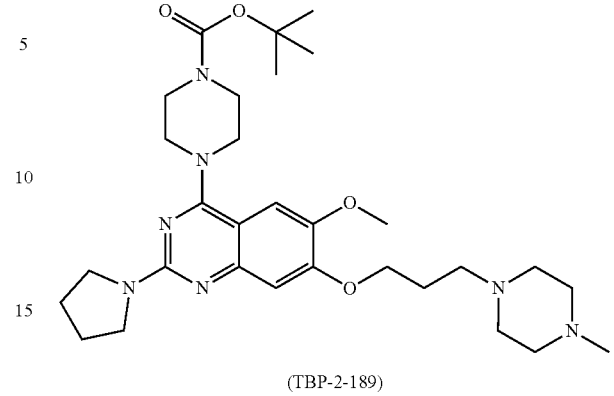
(TBP-2-189)
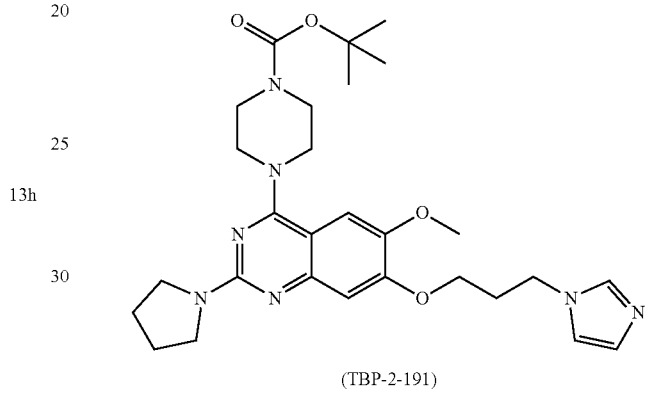
(TBP-2-191)
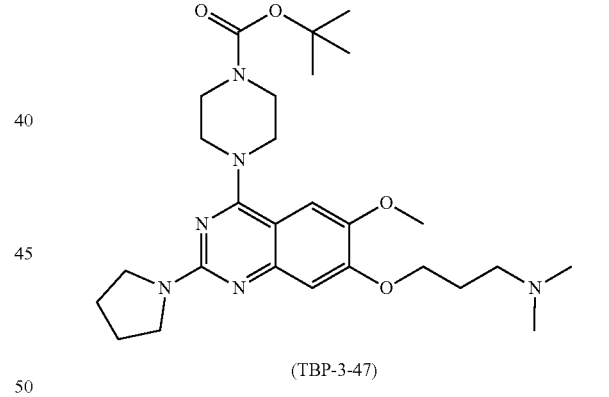
(TBP-3-47)
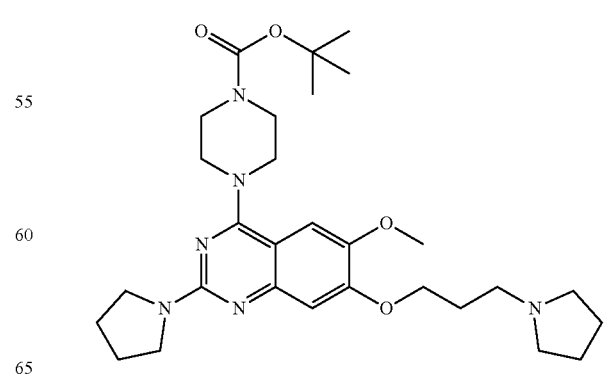
(TBP-2-145)

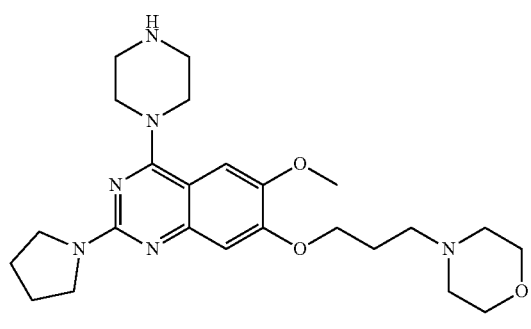
(TBP-2-179)
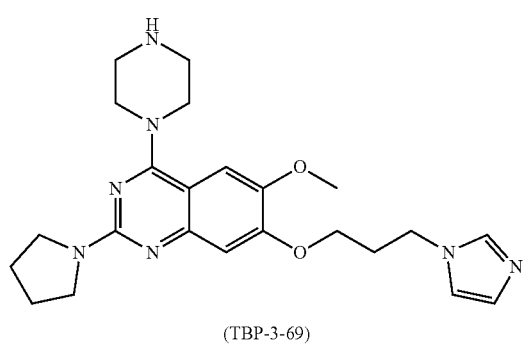
(TBP-3-69)
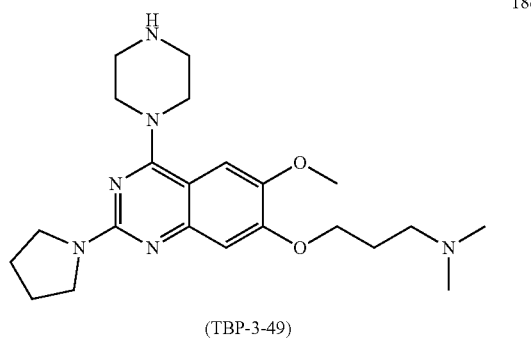
(TBP-3-49)
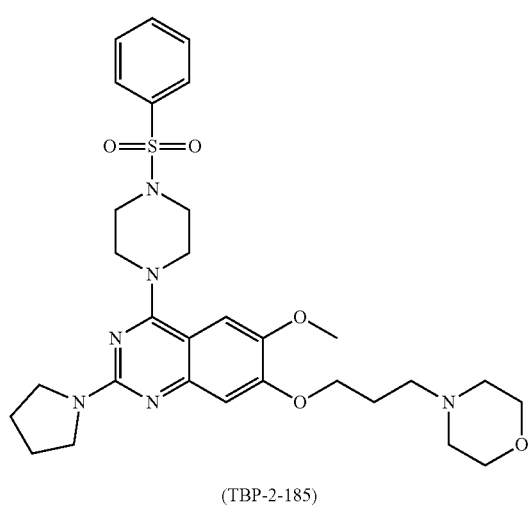
(TBP-2-185)
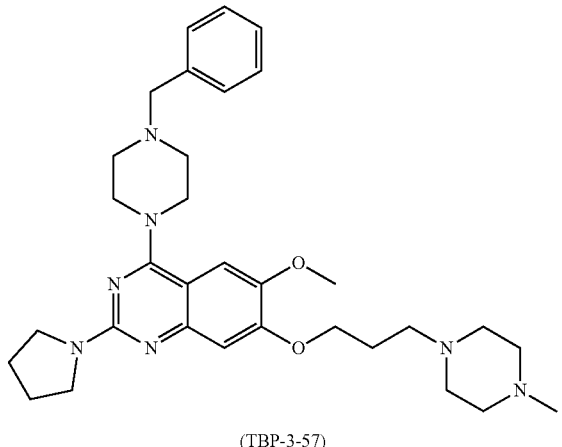
(TBP-3-57)
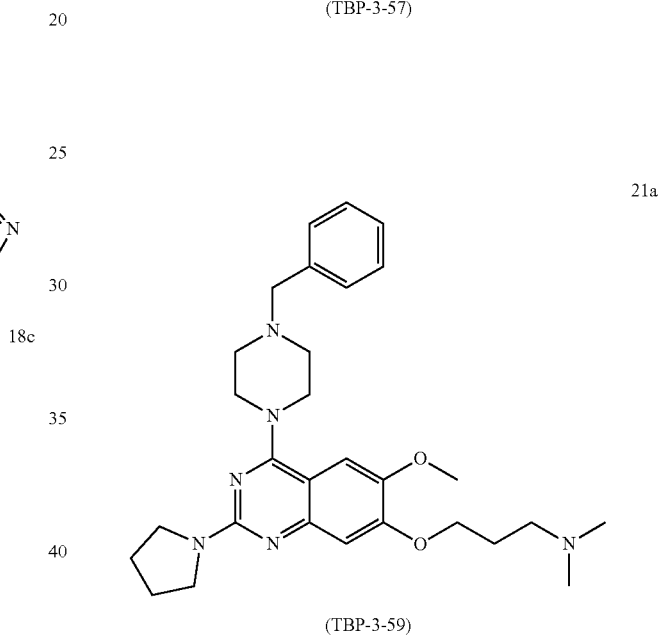
(TBP-3-59)
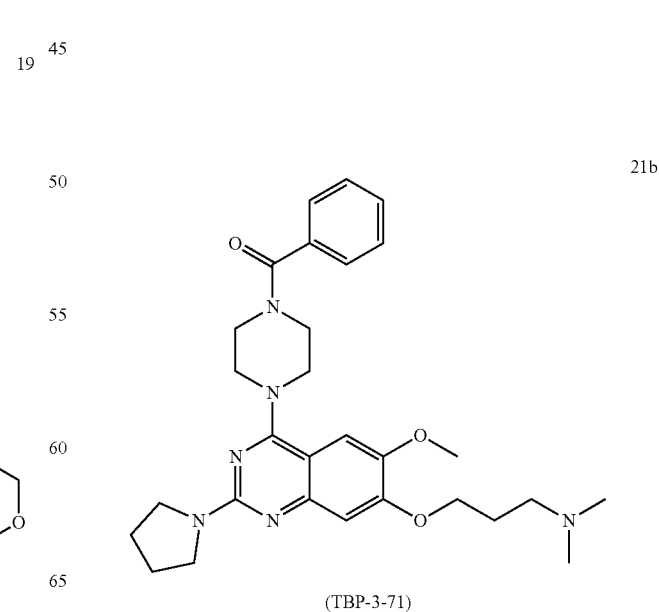
(TBP-3-71)

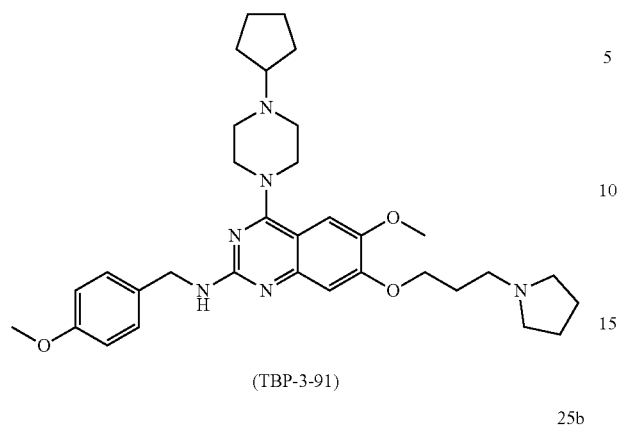
(TBP-3-91)
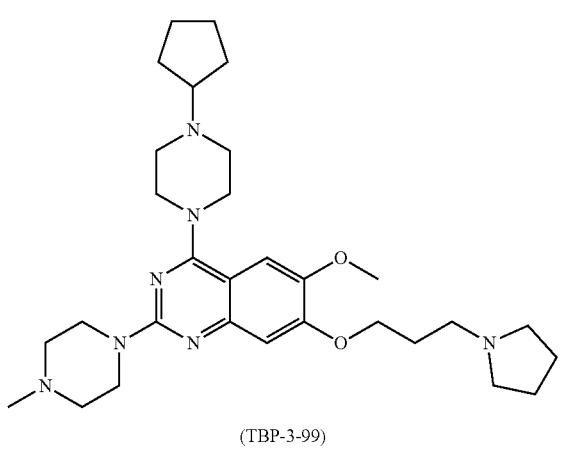
(TBP-3-99)
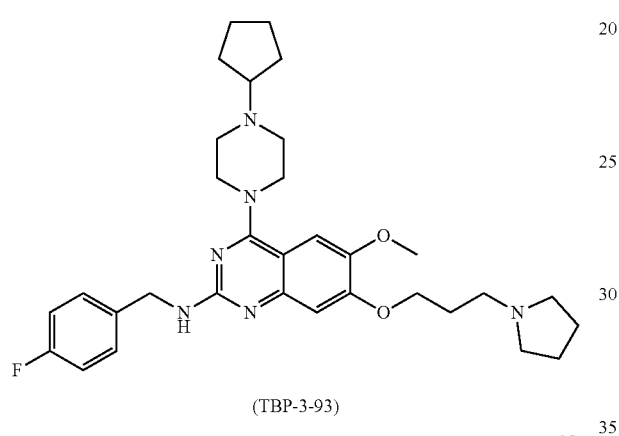
(TBP-3-93)
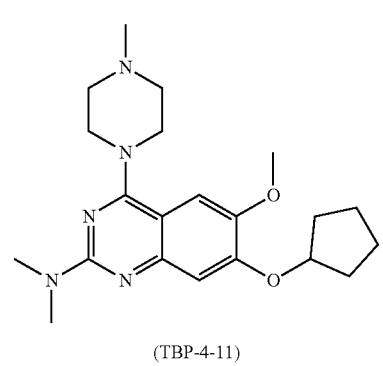
(TBP-4-11)
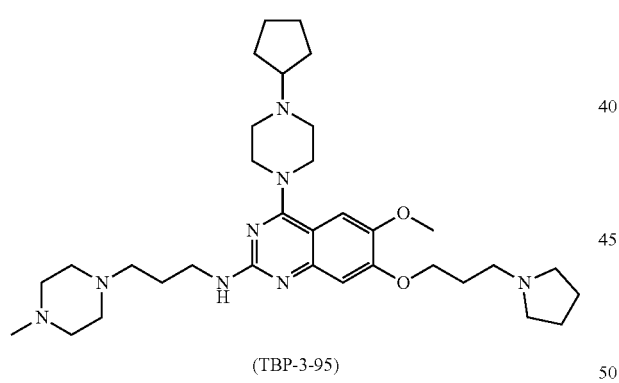
(TBP-3-95)
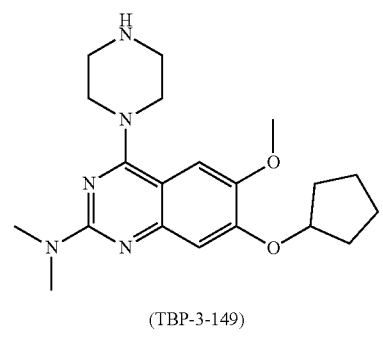
(TBP-3-149)
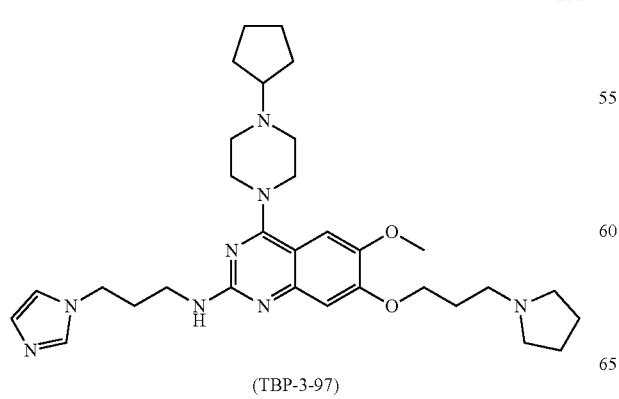
(TBP-3-97)
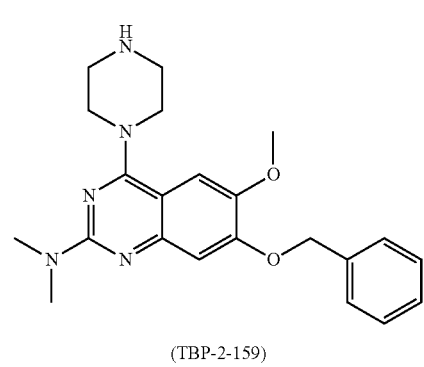
(TBP-2-159)

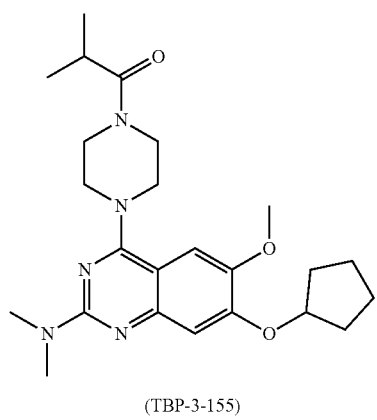
(TBP-3-155)
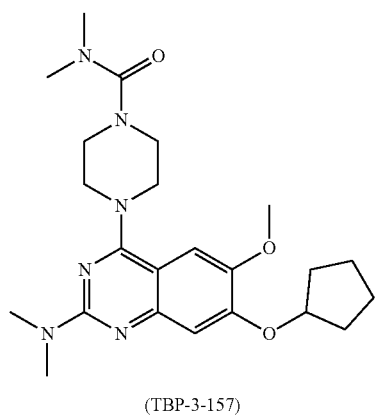
(TBP-3-157)
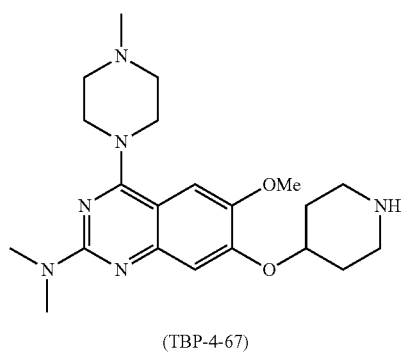
(TBP-4-67)
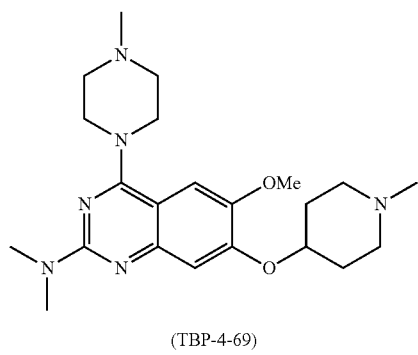
(TBP-4-69)
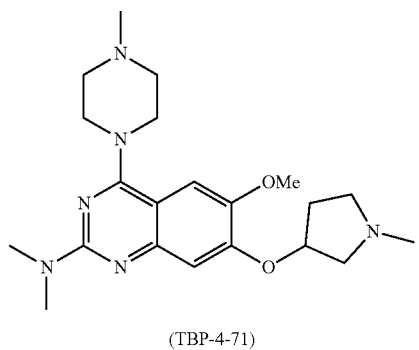
(TBP-4-71)
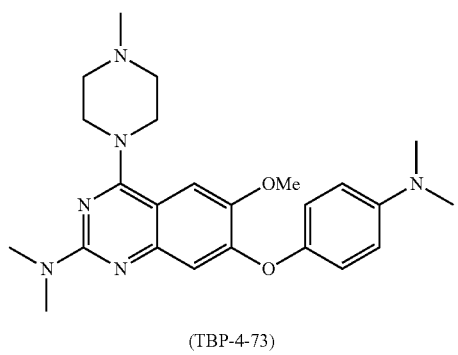
(TBP-4-73)
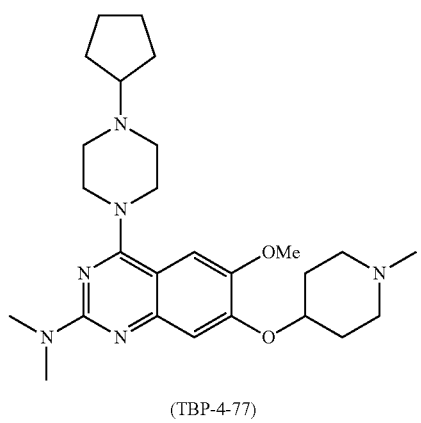
(TBP-4-77)
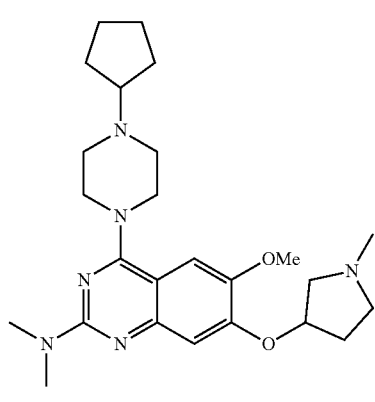
(TBP-4-79)

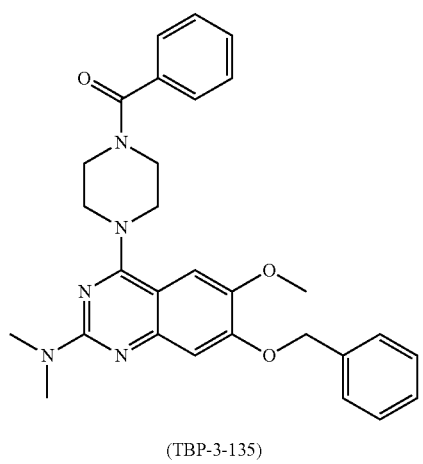
(TBP-3-135)
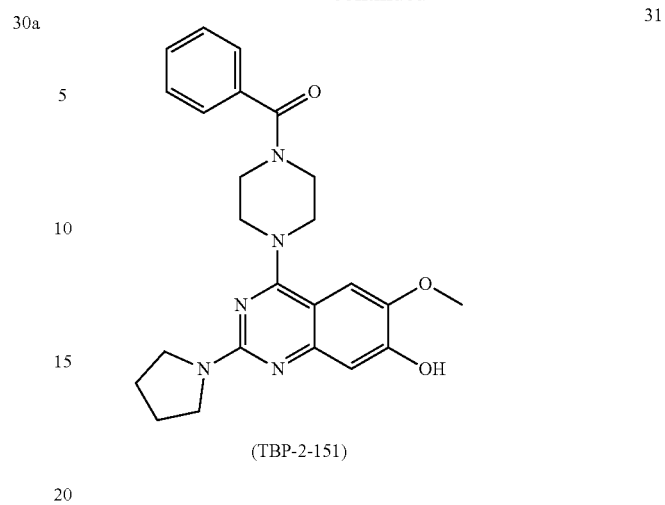
(TBP-2-151)
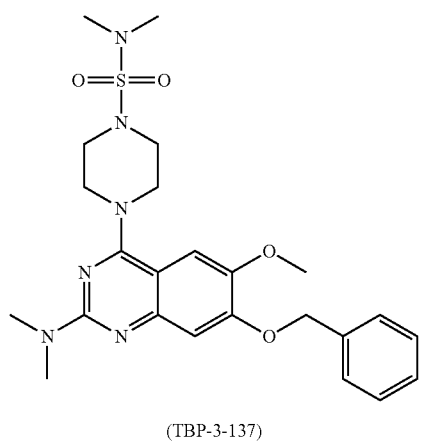
(TBP-3-137)
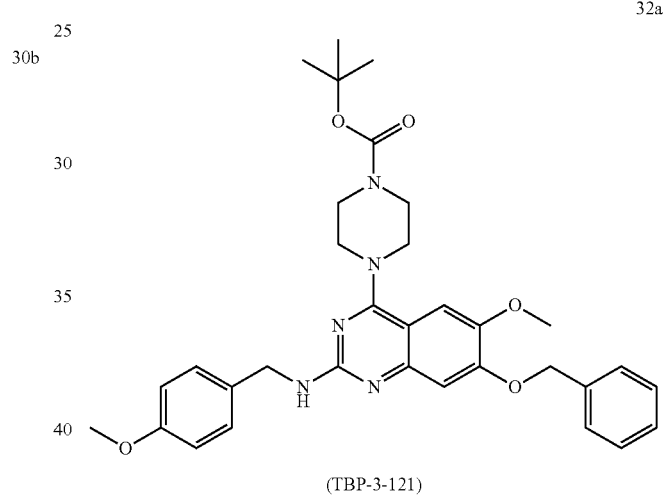
(TBP-3-121)
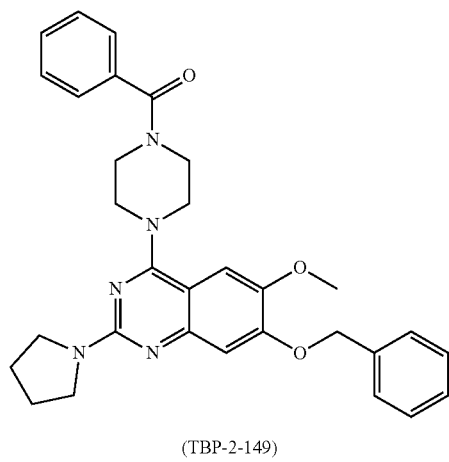
(TBP-2-149)
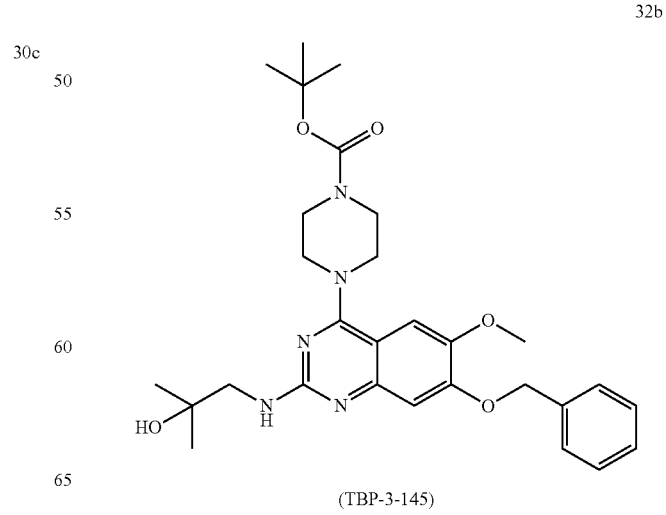
(TBP-3-145)

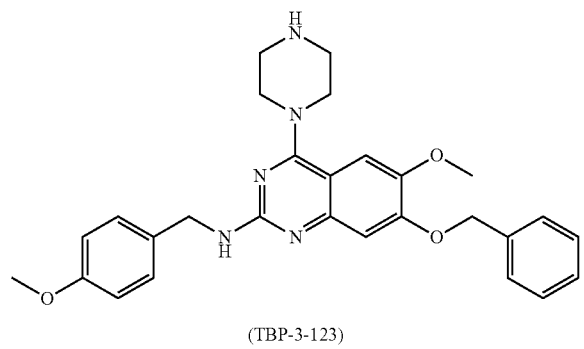
(TBP-3-123)
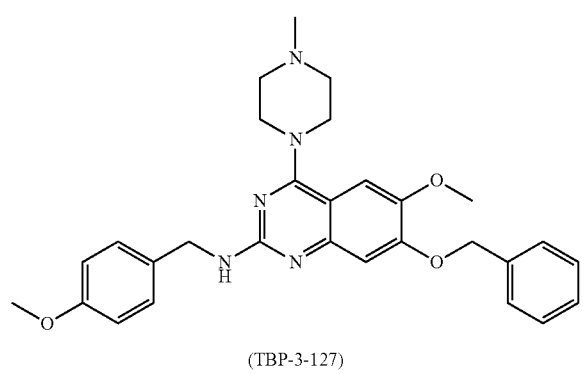
(TBP-3-127)
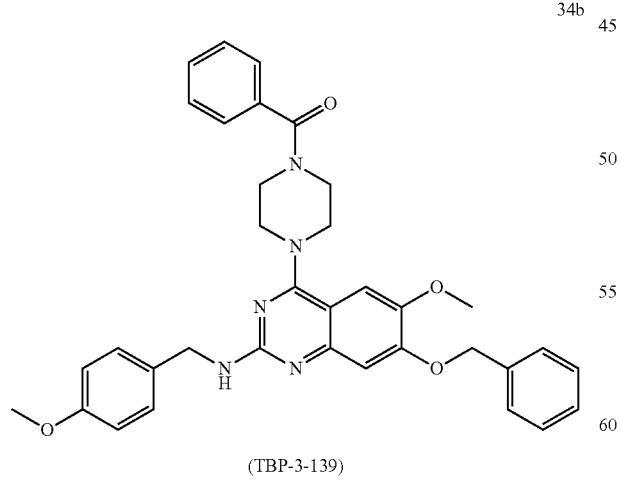
(TBP-3-139)
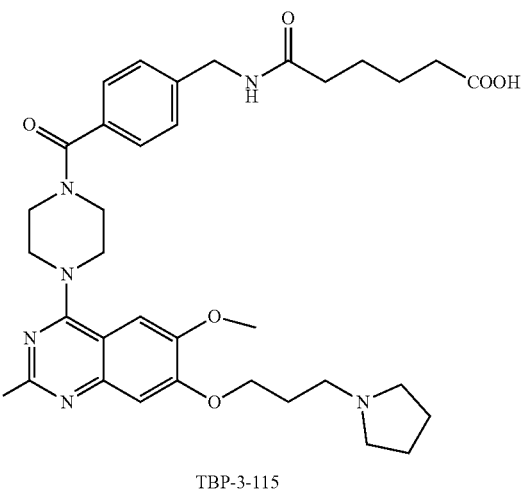
TBP-3-115
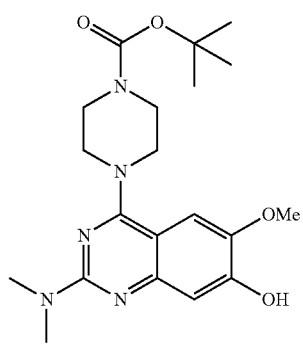
(TBP-4-81)
(TBP-2-71)

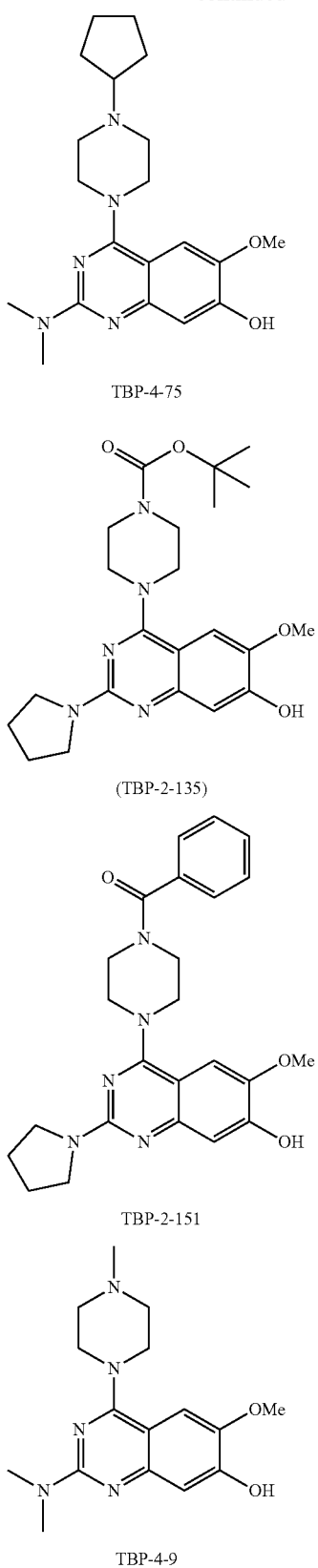
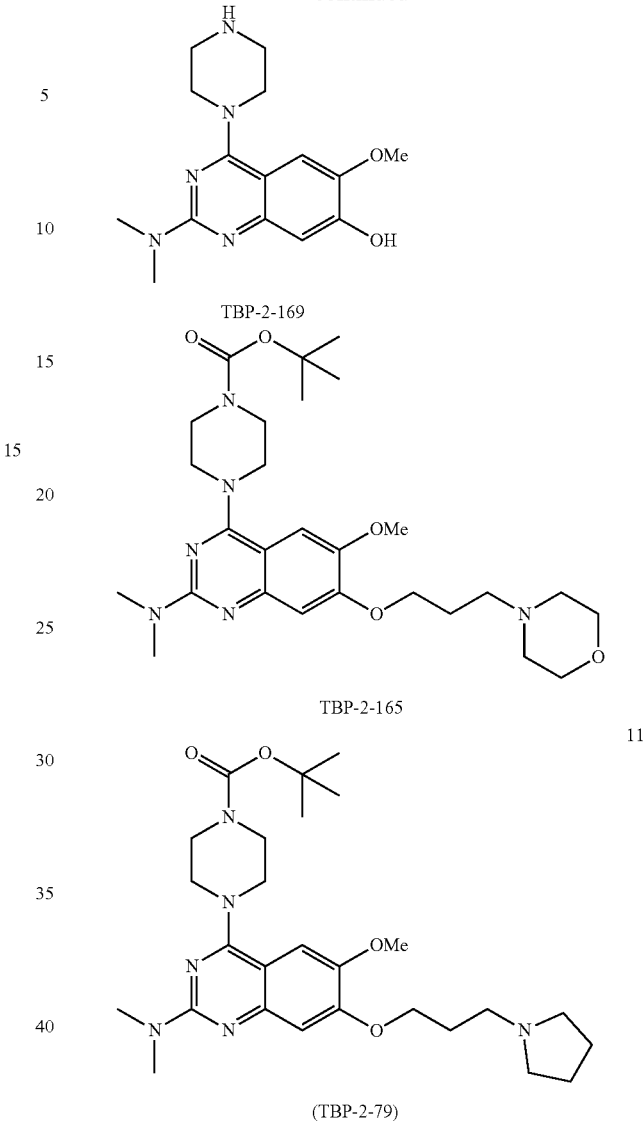

In another embodiment the process for the preparation of compounds of formula 1 comprising the steps of:

a. reacting compound of 6 with Boc-piperazxine to obtain compound 7;
b. reacting compound 7 obtained in step a) with amine to obtain compound of formula 8 or 14 or 32;
c. reacting compound 8 or 14 or 32 of step b) either with hydrogen in presence of Pd/C to obtain compound of 9 or 15 or reacting with TFA to obtain 29a or 29b or 33;
d. reacting compound 9 or 15 of step c) either with 1-chloro-3-bromopropane or bromocyclopentane to obtain compound 10 or 26 or 16;
e. reacting compound 10 or 16 of step d) with amine to compound 11 or 17;
f. reacting compound 11 or 17 of step e) or compound 26 of step d) or compound 14 of step b) with TFA to obtain 12 or 18 or 27;
g. reacting compound 12 obtained in step f) or 29a or 29b of step c) with sulphonyl chloride, alkyl or aryl carboxylic acid or alkyl halide or aldehyde or reacting compound 33 of step c) with alkyl halide or benzoic acid to obtain the compound of formula 1.

In another embodiment, further comprises, reacting compound 27 of step f) with alkyl halide or acid chloride to obtain compound of formula 1 or compound 31;

In another embodiment, the compound 31 further reacted with hydrogen in presence of Pd/C to obtain compound of formula 1.

In another embodiment, the process further comprising (i) reacting compound 6 with N-cyclopentylpiperazine or N-methyl piperazine followed by dimethyl amine to obtain an intermediate (ii) reacting the intermediate with hydrogen in presence of Pd/C to obtain compound 22 or 9b or 9c; and (iii) reacting compound 22, 9b or 9c with 1-(3-chloropropyl)pyrrolidine or bromaamine or 4-hydroxy amine to obtain compound of formula 1.

In another embodiment, the amine used in step b) r step e) is selected from the group consisting of,

NH₃,

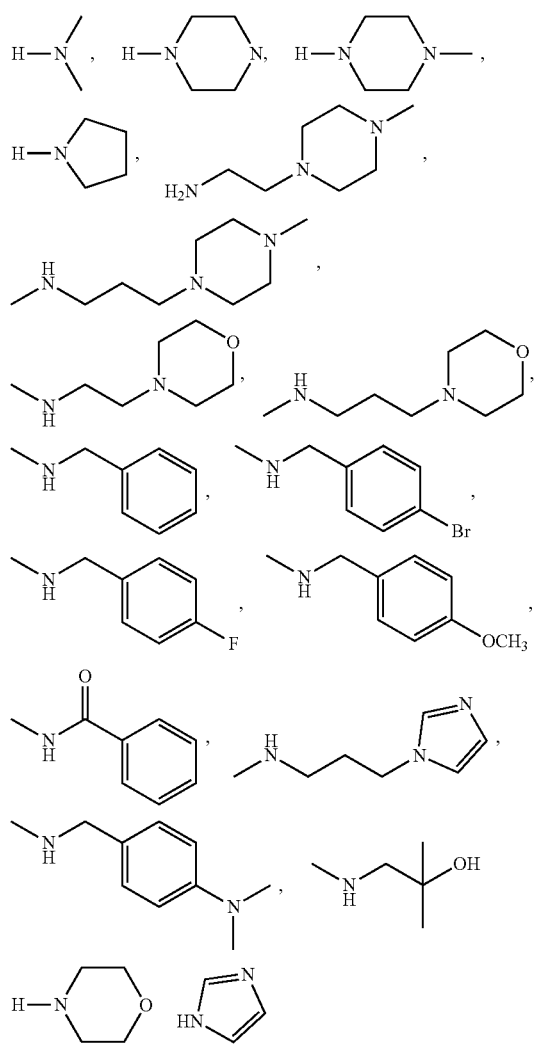

In another embodiment, the sulphonyl chloride is selected from the group consisting of, In another embodiment, the alkyl or aryl carboxylic acid or acid chloride is selected from the group consisting of, Y = OH, Cl In another embodiment, the alkyl halide is selected from the group consisting of, X = halogen In another embodiment, the alkyl or aryl aldehyde is selected from the group consisting of, In another embodiment of the present invention, a general screening method is provided involving human peripheral blood mononuclear cells to screen compounds of general formula I against all TLRs.

In another embodiment of the present invention, a method is provided for testing TLR9 antagonism of compounds of general formula I, in primary human plasmacytoid dendritic cells (pDCs) purified from human peripheral blood mononuclear cells.

In yet another embodiment of the present invention, a reporter assay method is provided involving a cell line expressing TLR9 to screen compounds of general formula I for TLR9 antagonism.

Assays results involving human peripheral blood mononuclear cells, human primary pDCs and transfected TLR9 cells are correlating.

In yet another embodiment of the present invention, said compounds with formula (I) described by the present invention affect immune stimulation via interaction with a TLR9.

In yet another embodiment of the present invention, it is believed that many of the small molecules described by the present invention inhibit immune stimulation via TLR9 antagonism.

In yet another embodiment of the present invention, the methods of the invention are useful whenever it is desirable to alter TLR9 mediated signalling in response to a suitable TLR ligand or TLR signalling agonist.

In yet another embodiment of the present invention, it is believed that the said compounds with formula (I) can be useful to inhibit an immune stimulatory nucleic acid associated response in a subject.

In yet another embodiment of the present invention, it is believed that the said compounds with formula (I) shows TLR9 antagonistic activity that can modulate autoreactive inflammation in different autoimmune diseases since aberrant TLR9 activation is implicated in such diseases.

In yet another embodiment of the present invention, it is believed that the said compounds with formula (I) can be used in a number of clinical applications, including as pharmaceutical agents and methods for treating conditions involving unwanted immune activity due to TLR9 activation.

In yet another embodiment of the present invention, the said compounds with formula (I) are without considerable cytotoxicity in HepG2 (a hepatic epithelial cell line) and SW480 (an intestinal mucosal epithelial cell line) cells at concentrations below 100 µM.

In yet another embodiment of the present invention, it is believed that the said compounds with formula (I) can be useful in the treatment of different clinical context of autoreactive inflammation, inflammation, allergy, asthma, graft rejection, and GvHD where aberrant TLR9 activation is present.

In yet another embodiment of the present invention, the small molecules with formula (I) is believed to affect TLRs directly and thus affect TLR-bearing cells, such as antigen-presenting cells (APCs), such agents can be used in conjunction with additional agents which affect non-APC immune cells, such as T lymphocytes (T cells). This will provide immune modulatory intervention at two levels: innate immunity and acquired immunity. The combination intervention is synergistic, since innate immunity is believed to initiate and support acquired immunity.

In one aspect of the invention, a method of affecting TLR mediated signalling in response to a TLR ligand is provided. The method according to this aspect involves detecting TLR9 antagonism of effective amount of a compound of Formula (I) using a reporter cell line that reports nuclear factor kappa B expression downstream of TLR9 signalling.

BRIEF DESCRIPTION OF ACCOMPANYING DRAWING

FIG. 1: Structural evolution of the quinazoline scaffold (FORMULA I) small molecules along with respective TLR9-antagonistic activity. The figure denotes percent interferon alpha production in response to TLR9-agonist ODN2216 from human peripheral blood mononuclear cells in the presence of different doses of the antagonist molecules (0, 0.1, 1, 5, 10 µM). Each row represents a single molecule with increasing antagonist concentrations from left to right as shown in the figure. TLR9-antagonist activity of one representative molecule belonging to each structural subset is indicated.

Figure 2:
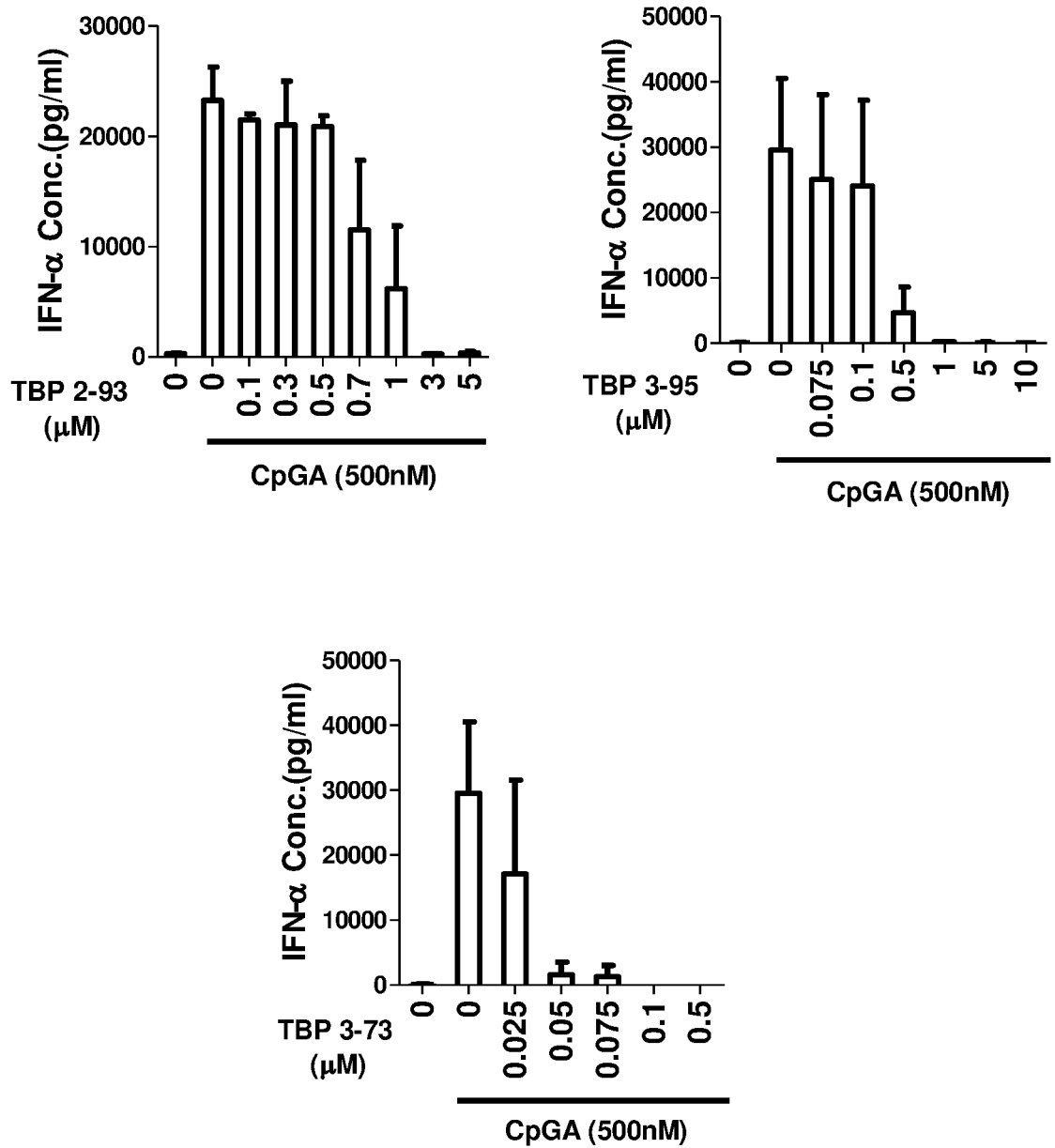

FIG. 2: TLR9 inhibition in pDCs by selected compounds with formula (I). The graphs denote dose-dependent reduction in IFN-α production in response to TLR9-agonist ODN2216 from human plasmacytoid dendritic cells (pDC) in the presence of different doses of the antagonist molecules. Each data is derived from two donors. Average values are reported.

Figure 3A:
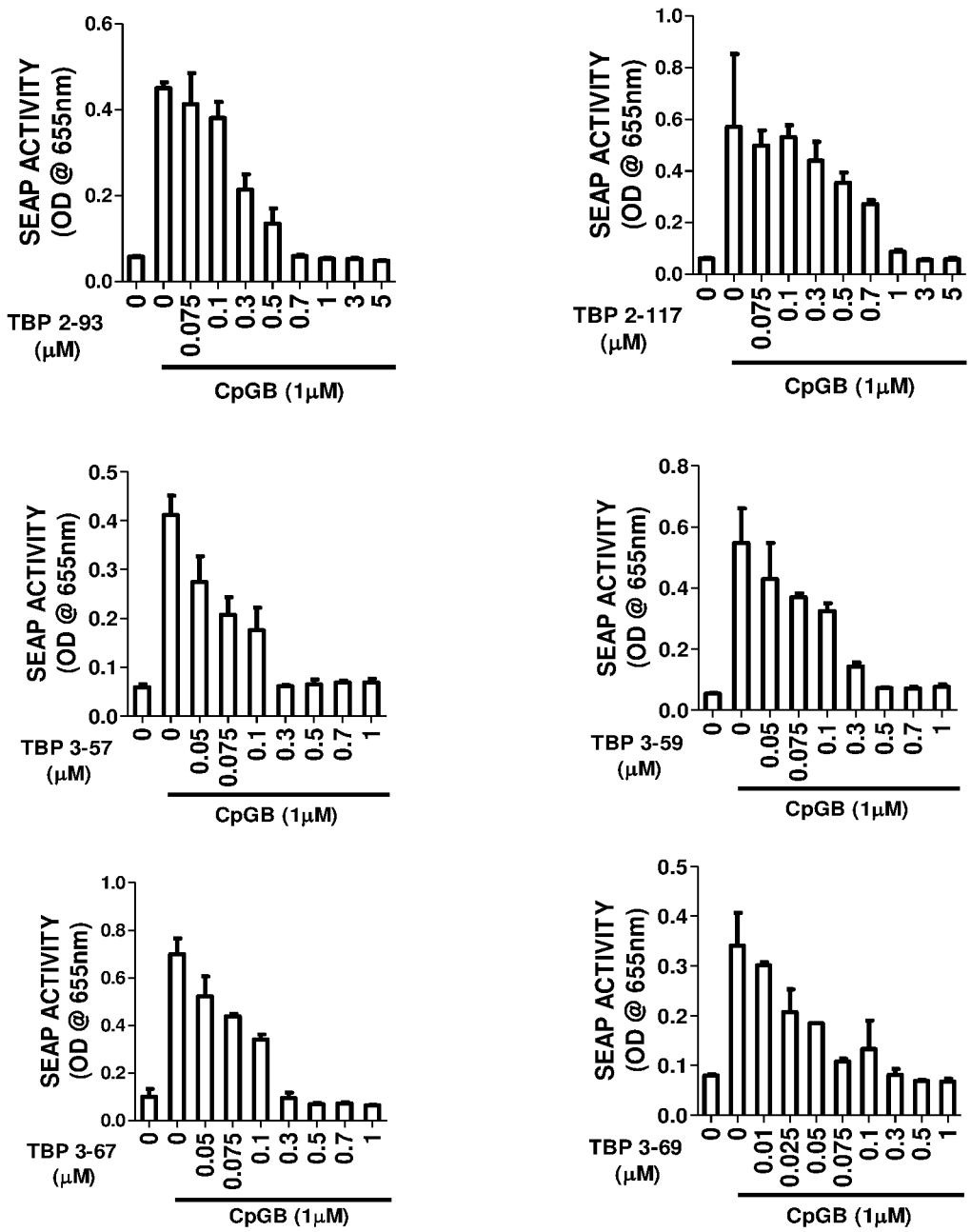

FIG. 3A: TLR9 inhibition in HEK-Blue-hTLR9 reporter cell line by selected compounds with formula (I). The graphs denote dose-dependent inhibition of TLR9 activation in a HEK-Blue-hTLR9 reporter cell line in the presence of different doses of the antagonist molecules, which is represented in terms of decrease in SEAP activity. Data shown are mean of triplicate wells±SD.

Figure 3B:
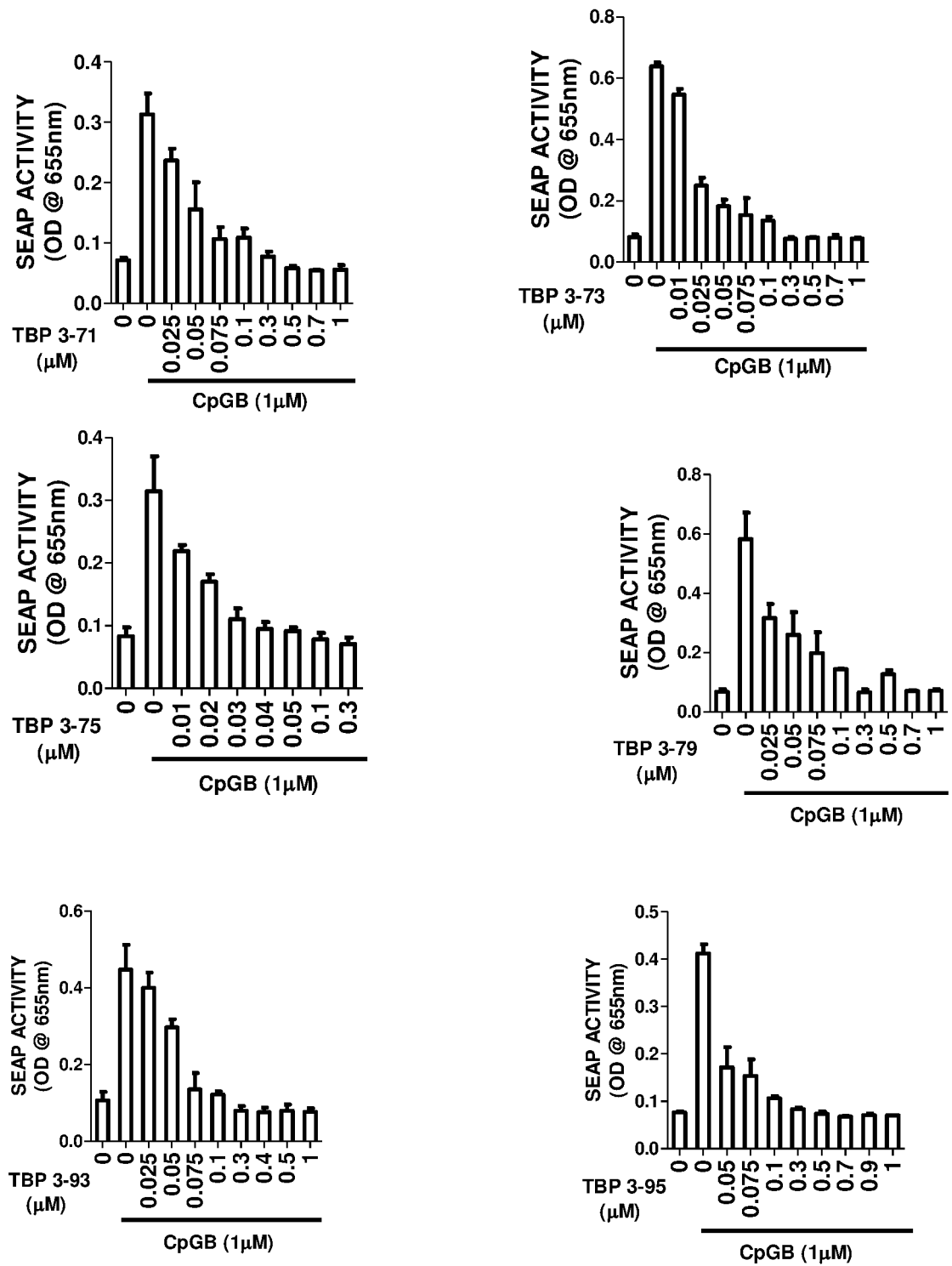

FIG. 3B: TLR9 inhibition in HEK-Blue-hTLR9 reporter cell line by selected compounds with formula (I). The graphs denote dose-dependent inhibition of TLR9 activation in a HEK-Blue-hTLR9 reporter cell line in the presence of different doses of tghe antagonist molecules, which is represented in terms of decrease in SEAP activity. Data shown are mean of triplicate wells±SD.

Figure 3C:
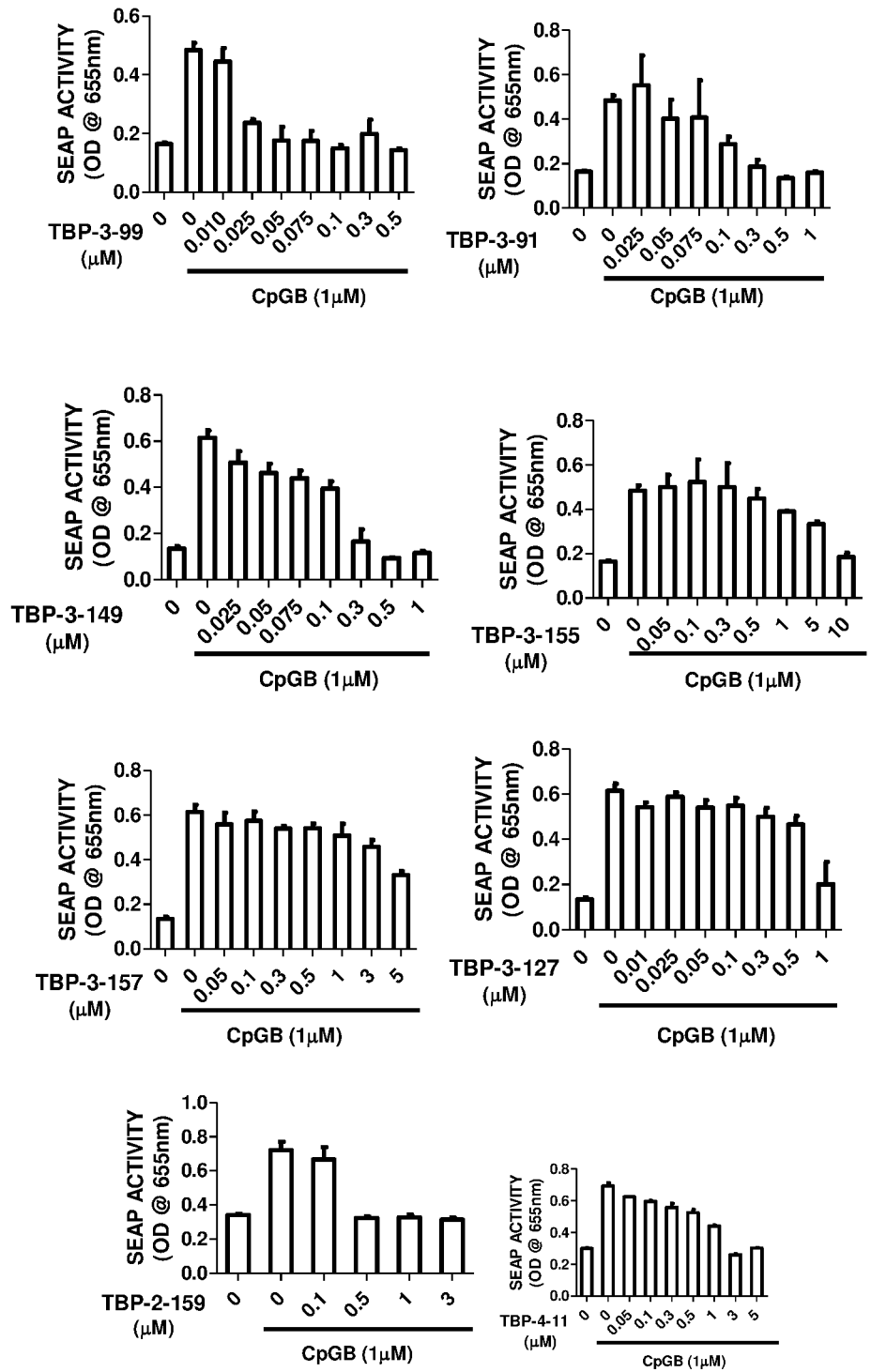

FIG. 3C: TLR9 inhibition in HEK-Blue-hTLR9 reporter cell line by selected compounds with formula (I). The graphs denote dose-dependent inhibition of TLR9 activation in a HEK-Blue-nTlR9 reporter cell line in the presence of different doses of the antagonist molecules, which is represented in terms of decrease in SEAP activity. Data shown are mean of triplicate wells±SD.

Figure 3D:
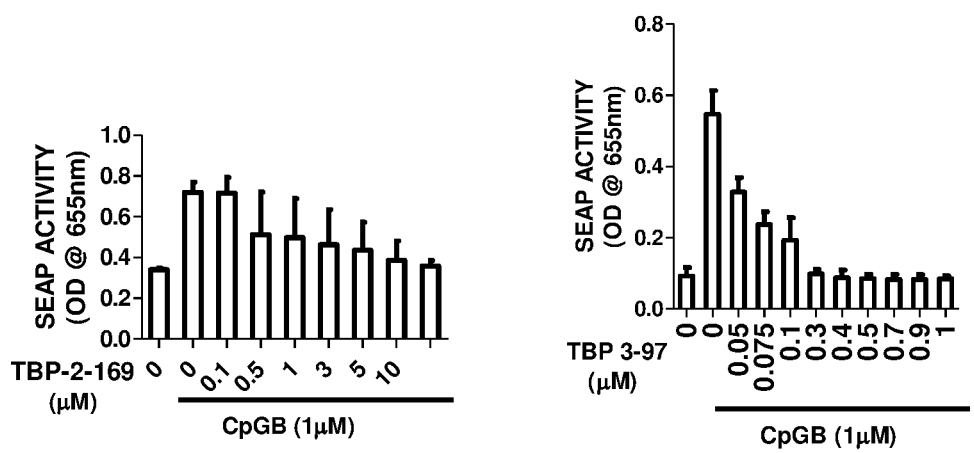

FIG. 3D: TLR9 inhibition HEK-Blue-hTLR9 reporter cell line by selected compounds with formula (I). The graphs denote dose-dependent inhibition of TLR9 activation in a HEK-hTLR9 reporter cell line in the presence of different doses of the antagonist molecules, which is represented in terms of decrease in SEAP activity. Data shown are mean of triplicate wells±SD.

Figure 4:
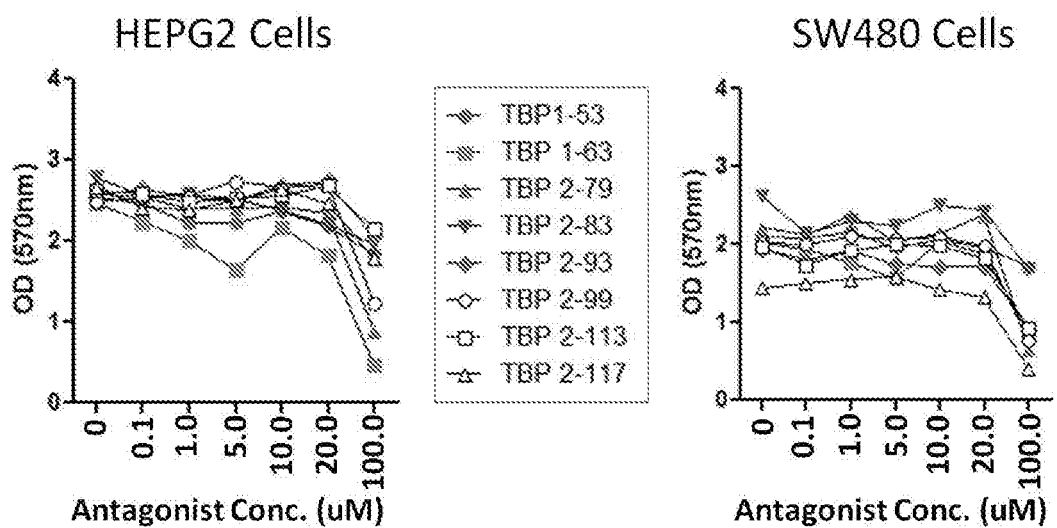

FIG. 4: Cytotoxicity based on MTT assay of the identified TLR9 antagonist molecules. HepG2 and SW480 cells were cultured in presence of different concentrations (0.1, 0.5, 1, 10, 20 and 100 µM) of different candidate small molecule antagonists for 24 hrs. At 24 hrs MTT assay was performed as described in the text. Respective absorbance at 570 nm is represented. Each line represents a specific small molecule as denoted in the legend.

FIG. 5A: Table 2 depicts IC50 values of the compounds with quinazoline scaffold with formula (I) composition of the Invention.

FIG. 5B Table 2 depicts IC50 values of the compounds with quinazoline scaffold with formula (I) composition of the Invention.

DETAILED DESCRIPTION OF THE INVENTION

In the present invention the synthesis of compounds of general formula I was prepared as follows.

Intermediate 6 was synthesized through the 5 steps synthetic sequences as shown in Example 1, from commercially available 3-methoxy-4-hydroxybenzonitrile. Benzylation of compound 1 followed by nitration and reduction produces 4-(benzyloxy)-5-methoxy-2-nitrobenzonitrile 4, which upon amine amide coupling by CDI reagent forms quinazolinedione derivative 5. On POCl$_3$ treatment 5 was converted to the intermediate 2,4-dichloroquinazoline derivative 6.

Derivatives 13 were prepared via 7 steps from the dichloroquinazoline intermediate 6 (Example 1). On treatment with Bocpiperizine followed by dimethylamine addition 6 was converted to diaminosubstituted quinazoline 8. On debenzylation by Pd/C and hydrogen gas of 8 followed by SN2 reaction by 1-bromo-3-chloropropane and pyrrolidine substitution at 7-position of quinazoline afforded compound 11. Boc group deprotection using TFA and subsequent sulphonyl chloride substitution afforded compounds 13a, 13b and benzylbromide, bromocyclopentane, bromomethylcyclopentane substitution afforded 13g, 13e, 13d, and carboxylic acid coupling reactions with the corresponding secondary amine using HATU produces the derivatives 13c, 13f. Compound 7 on substitution by pyrrolidine followed by hydrogenation and SN2 reaction by 1-bromo-3-chloropropane gave compound 16, which upon treatment with different bases provided compounds 17 series as shown in Scheme 3. Boc group deprotection using TFA afforded derivatives 18a, 18b, and 18c (Scheme 4). Compound 6 on treatment with 1-cyclopentylpiperazine followed by hydrogenation and 1-(3-chloropropyl)pyrrolidine attachment provided compound 24, which upon treatment with different bases at 2-position in quinazoline scaffold gave the 25 derivative series (Scheme-6). Following the above reaction procedure few more derivatives (28a, 28b, 28c, 30a, 30b, 32a, 32b, 34a, 34b) containing different substitution at the three variable position of quinazoline have been synthesized in Scheme-7, 8, 9 and 10.

The synthesized compounds of general formula I were screened for toll-like receptor 9 antagonistic activities by a medium throughput biological assay based on toll-like receptor 9 activation in primary human immune cells. Type A and type B unmethylated cytosine-guanine rich DNA oligonucleotides (CpG oligonucleotides) are the bona fide ligands for TLR 9. On activation of TLR9 by CpG oligonucleotides, type I interferons (e.g. IFN-alpha) are released. The synthesized compounds of general formula I was able to alter the release of type I interferons (e.g. IFN-alpha).

Type I interferons (IFN-alpha) production from human peripheral blood mononuclear cells in response to type A CpG oligonucleotides (CpGA) almost exclusively results from TLR9 triggering on the PDCs. Based on this principle the screening assay was designed where we isolated peripheral blood mononuclear cells (PBMCs) from venous blood collected from healthy donors using density gradient centrifugation. The synthesized compounds of general formula I having TLR9 antagonistic activity inhibited IFN-alpha production in this screening assay.

The synthesized compounds of general formula I were screened for toll-like receptor 9 antagonistic activities by a medium throughput biological assay based on toll-like receptor 9 activation in plasmacytoid dendritic cells (pDC) which were isolated from PBMCs of healthy donors. The synthesized compounds of general formula I having TLR9 antagonistic activity inhibited IFN-alpha production in response to CpGA in this screening assay.

The synthesized compounds of general formula I were screened for toll-like receptor 9 antagonism using a HEK-Blue-hTLR9 Secreted Alkaline Phosphatase (SEAP) reporter assay. The synthesized compounds of general formula I having TLR9 antagonistic activity inhibited TLR9-mediated NF-kB activation in a dose-dependent manner.

The synthesized compounds of general formula I were screened for cytotoxicity. MTT assay is a colorimetric assay for assessing cell viability. HepG2 (a hepatic epithelial cell line) and SW480 (an intestinal mucosal epithelial cell line) cells were used to check cytotoxicity. The synthesized compounds of general formula I did not show any considerable cytotoxicity at concentrations below 100 uM on this assay (FIG. 4).

Experimental Details:

The following examples are intended for illustrative purposes only and are not to be construed as being limitations for the invention thereon in any manner. Temperatures are given in degree Celsius. The structure of final products, intermediates and starting materials is confirmed by standard analytical methods, e.g. spectroscopic characterization, e.g., MS, NMR. Abbreviations used are those conventional in the art. All starting materials, reagents, catalysts, building blocks, acids, bases, dehydrating agent and solvents utilized to synthesize the compounds of the present invention are either commercially available or can be produced by known organic synthesis methods in the art.

Abbreviations

BnBr Benzylbromide
DMF N,N-dimethylformamide
AcOH Acetic acid
CDI 1,1'-Carbonyldiimidazole
$POCl_3$ phosphorous oxychloride
DIPEA N,N-Diisopropylethylamine
DCM Dichloromethane
TFA Trifluoroacetic acid
DMSO Dimethyl sulfoxide
Boc Tert butyl carbamate
THF Tetrahydrofurane
HATU 1-[Bis(dimethylamino)methylene]-1H-1,2,3-triazolo[4,5-b]pyridinium-3-oxid hexafluorophosphate
HBTU 2-(1H-benzotriazol-1,1,3,3-tetramethyluronium hexafluorophosphate)

EXAMPLES

Example 1

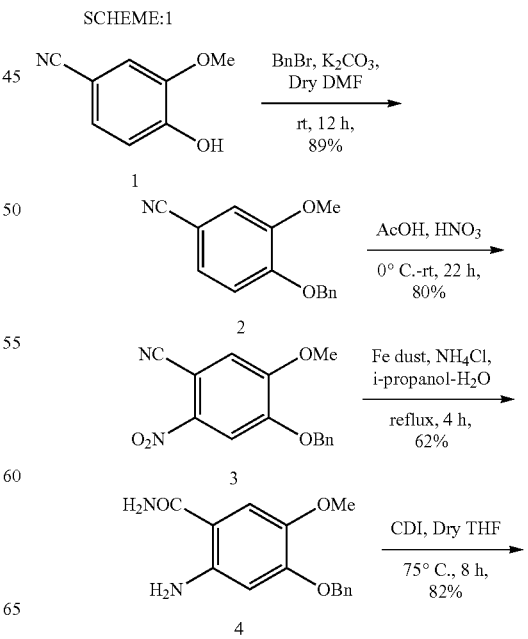

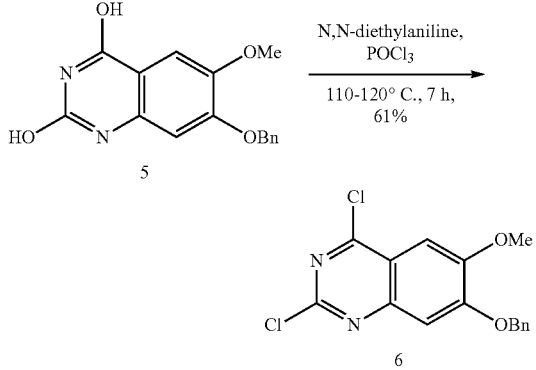

consumption of starting material. The precipitate was filtered and washed with THF to afford compound 5 (1.85, 82% yield) as a yellow solid. $^1$H NMR (300 MHz, DMSO-$d_6$) δ 3.86 (s, 3H), 5.14 (s, 2H), 6.79 (s, 1H), 7.28 (s, 1H), 7.28-7.48 (m, 5H). FAB [M+H]$^+$:299.2.

7-(Benzyloxy)-2,4-dichloro-6-methoxyquinazoline (6)

Compound 5 (2 g, 6.71 mmol) was taken in 5 mL N,N-diethylaniline, the reaction mixture was cooled to 0° C. Then POCl$_3$ (10 mL) was added very slowly and the reaction mixture was stirred at 110° C.-120° C. for overnight. The reaction mixture was neutralized with saturated sodium bicarbonate aqueous solution. The resulting mixture was extracted with chloroform. The organic solvents were dried, concentrated, and purified by silica gel chromatography (hexane to 20% ethyl acetate in hexanes) to give compound 6 as a light yellow solid (1.40 g, 61% yield). $^1$H NMR (300 MHz, CDCl$_3$) δ 4.06 (s, 3H), 5.31 (s, 2H), 7.26 (s, 1H), 7.30 (s, 1H), 7.33-7.51 (m, 5H). FAB [M+H]$^+$:335.2.

4-(Benzyloxy)-3-methoxybenzonitrile (2)

4-hydroxy-3-methoxybenzonitrile (10.0 g, 67.11 mmol) and potassium carbonate (19 g, 134 mmol) were taken in Dry DMF (20 mL) at 0° C. And then benzyl bromide (9.0 mL, 80.5 mmol) was added to the reaction mixture very slowly. The reaction mixture was stirred 12 h at room temperature, and brine solution (100 mL) was added. The resulting precipitate was collected, washed with water and dried to provide 4-benzyloxy-3-methoxybenzonitrile as a white solid (13.9 g, 89% yield). $^1$H NMR (300 MHz, CDCl$_3$) δ 3.88 (s, 3H), 5.18 (s, 2H), 6.88 (d, J=8.4 Hz, 1H), 7.03 (s, 1H), 7.21 (dd, J=8.4, 2.0 Hz, 1H), 7.32-7.42 (m, 5H). ESI [M+Na]$^+$: 262.25).

4-(Benzyloxy)-5-methoxy-2-nitrobenzonitrile (3)

To an ice cold solution of compound 2 (8.0 g, 33.6 mmol) in 20 mL acetic acid, 69% Nitric acid (126.4 mmol) was added dropwise. Reaction mixture was slowly allowed to come at room temperature and kept in that condition 22 h. The reaction mixture was neutralized with 4N NaOH solution and then residue was extracted with DCM, washed with brine and dried over sodium sulphate. Concentrating DCM part provide compound 3 as a yellow solid (6.8 g, 82% yield). $^1$H NMR (300 MHz, CDCl$_3$) δ 4.01 (s, 3H), 5.26 (s, 2H), 7.21 (s, 1H), 7.36-7.42 (m, 5H), 7.85 (s. 1H). ESI [M+Na]$^+$: 307.14).

2-Amino-4-(benzyloxy)-5-methoxybenzamide (4)

A mixture of compound 3 (5.0 g, 17.6 mmol), iron dust (3.0 g, 54.8 mmol), and ammonium chloride (3.8 g, 70.4 mmol) in isopropyl alcohol-water (2:1) 50 mL was heated to reflux for 4 h. Then, the reaction mixture filtered through celite and the filtrate part was extracted with 5% methanol in DCM. The organic part was dried, concentrated and purified by silica gel chromatography with 10% methanol in DCM to afford compound 4 as light yellow solid (2.7 g, 52% yield). $^1$H NMR (300 MHz, CDCl$_3$) δ 3.89 (s, 3H), 5.15 (s, 2H), 6.20 (s, 1H), 6.88 (s, 1H), 7.29-7.51 (m, 5H). FAB [M+H]$^+$: 272.6.

7-(Benzyloxy)-6-methoxyquinazoline-2,4-diol (5)

Compound 4 (2.0 g, 61 mmol) was taken in dry THF, to the clean solution CDI (8.05 mmol) was added and the reaction mixture was heated at 75° C. A precipitate formed and the reaction was continued for 8 hr for complete Example 2

SCHEME:2

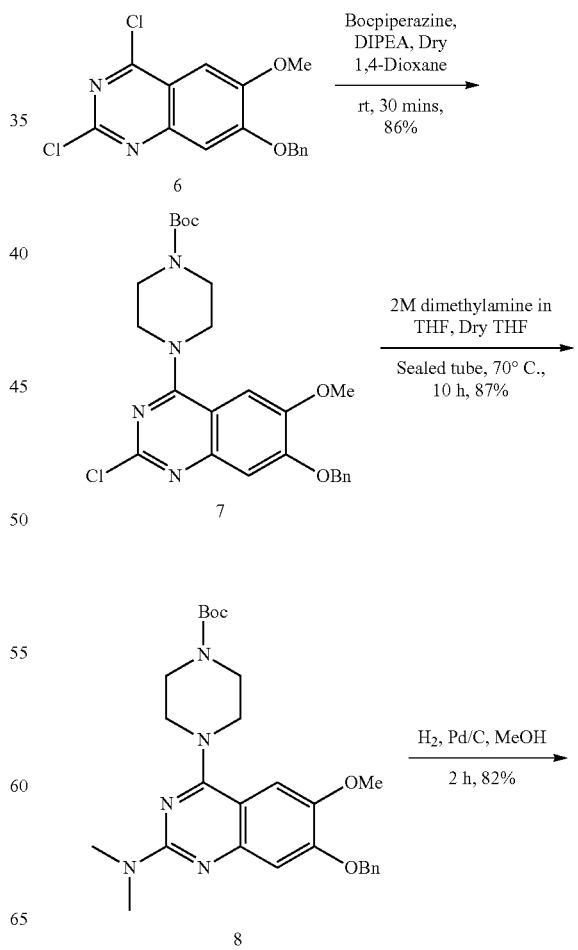

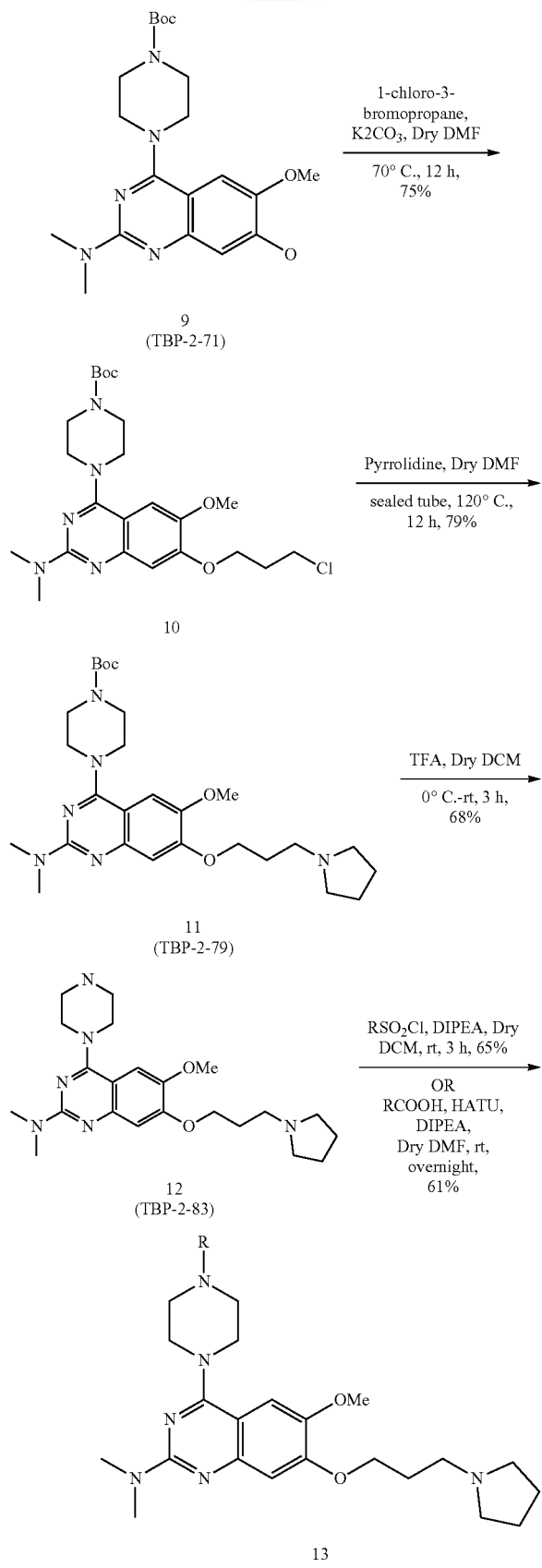
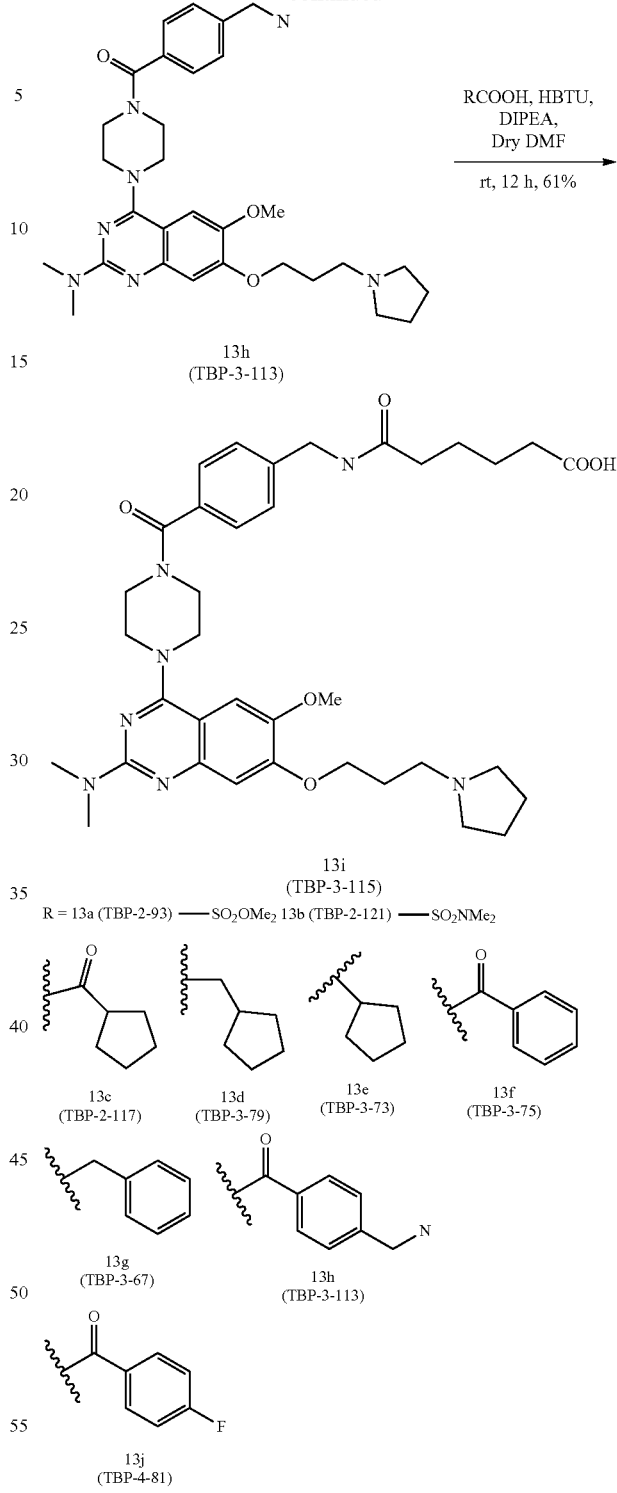
t-Butyl-4-(7-(benzyloxy-2-chloro-6-methoxyquinazoline-4-yl)piperazine-1-carboxylate (7)
N-bocPiperazine (620 mg, 0.003 mmol) was added to a stirred solution of 6 (1 g, 0.0029 mmol) in dry 1,4-Dioxane and DIPEA (0.7 mL, 0.005 mmol). The solution was stirred for 30 min at room temperature. After adding water a precipitate was formed which was filtered to give compound 7 (1.2g, 86% yield) as white solid (m.p—155-158° C.). $^1$H NMR (300 MHz, CDCl$_3$) δ 1.52 (s, 9H), 3.63 (m, 4H), 3.69 (m, 4H), 3.97 (s, 3H), 5.27 (s, 2H), 7.05 (s, 1H), 7.21 (s, 1H), 7.33-7.41 (m, 3H), 7.44-7.47 (m, 2H). EI-HRMS [M]$^+$: Calculated: 484.1877. Found: 484.1877.

t-Butyl4-(7-(benzyloxy)-2-(dimethylamino)-6-methoxyquinazolin-4yl)piperazine-1-carboxylate (8)

2M dimethylamine in THF (1 mL, 2 mmol)) was added to a solution of compound 7 (250 mg, 0.52 mmol) in dry THF (2 mL) and the reaction mixture was stirred for 10 h at 75° C. in sealed tube. THF was removed under vacuum, the residue then dissolved in ethyl acetate and the organic layer was washed with water and brine, dried and concentrated to give compound 8 (220 mg, 87% yield) as a white solid (m.p—192-195° C.). $^1$H NMR (300 MHz, CDCl$_3$) δ 1.52 (s, 9H), 3.21 (s, 6H), 3.63 (t, J=6 Hz, 4H), 3.69 (t, J=6 Hz, 4H), 3.97 (s, 3H), 5.27 (s, 2H), 6.98 (s, 1H), 7.08 (s, 1H), 7.31-7.38 (m, 3H), 7.41-7.49 (m, 2H). EI-HRMS [M]$^+$: Calculated: 493.2689. Found: 494.2757.

t-Butyl-4-(2-(dimethylamino)-7-hydroxy-6-methoxyquinazolin-4yl)piperazine-1-carboxylate (9)

10% Pd/C (50 mg) was added to a solution of compound 8 (500 mg, 0.08 mmol) in MeOH 10 mL followed by the addition of 1 mL DIPEA. A hydrogen balloon was attached and the mixture was stirred at room temperature for 3h. The reaction mixture was filtered through celite and washed with methanol until the filtrate became colourless. The solution was concentrated to provide compound 9 (330 mg, 82% yield) as pale yellow solid (m.p—254-256° C. decompose). $^1$H NMR (300 MHz, CDCl$_3$) δ 1.31 (s, 9H), 3.16 (s, 6H), 3.47-3.51 (m, 4H), 3.75 (s, 3H), 3.80-3.83 (m, 4H), 6.86 (s, 1H), 7.29 (s, 1H), EI-HRMS [M]$^+$: Calculated: 403.2220. Found: 403.2219.

t-Butyl-4-(7-(3-chloropropoxy)-2-(dimethylamino)-6methoxyquinazolin-4yl)piperazine-1-carboxylate (10)

Compound 9 (200 mg, 0.65 mmol) and potassium carbonate (200 mg, 1.43 mmol) was taken in dry DMF (5 mL). The reaction mixture was stirred at room temperature for 30 mins. Then 1-bromo-3-chloropropane (7.2 µL, 0.72 mmol) was added and the mixture was stirred at 110° C. for 12 h. The reaction mixture was extracted with ethyl acetate and washed with 50 mL of water followed by brine wash, dried with sodium sulphate and concentrated. The residue was purified by silica gel flash column chromatography, eluting with 60% ethyl acetate in hexane, to give compound 10 (169 mg, 72% yield) as a colourless gummy solid. $^1$H NMR (300 MHz, CDCl$_3$) δ 1.49 (s, 9H), 2.45-2.31 (m, 2H), 3.22 (s, 6H), 3.63 (t, J=6 Hz, 4H), 3.69 (t, J=6 Hz, 4H), 3.79-3.77 (t, J=6 Hz, 2H), 3.88 (s, 3H), 4.29-4.24 (m, 2H), 6.96 (s, 2H), 7.08 (s, 1H). EI-HRMS [M]$^+$: Calculated: 479.2299 Found: 479.2297.

t-Butyl-4-(2-(dimethylamino)-6-methoxy-7-(3-(pyrrolidine-1-yl)propoxy) quinazoline-4-yl) piperazine-1-carboxylate (11)

To a solution of compound 10 (150 mg, 0.33 mmol) in 2 mL dry DMF I a sealed tube pyrroline (2.8 µL, 0.34 mmol) was added and the reaction mixture was heated at 90° C. for 12 h. The reaction mixture was extracted with ethyl acetate and washed with 50 mL of water followed by brine wash; ethyl acetate part was dried with sodium sulphate and concentrated. The residue was purified by silica gel flash column chromatography, eluting with 20% CMA (NH$_3$: MeOH:CHCl$_3$=5:10:85) in chloroform, to give compound 11 as a gummy solid. $^1$H NMR (300 MHz, CDCl$_3$) δ 1.49 (s, 9H), 2.45-2.31 (m, 2H), 3.22 (s, 6H), 3.63 (br. s, 4H), 3.69 (br. s, 4H), 3.79-3.77 (m, 2H), 3.88 (s, 3H), 4.31 (t, J=6.2 Hz, 2H), 7.2 (s, 2H), 7.99 (s, 1H). EI-HRMS [M]$^+$: Calculated: 514.3268 Found: 514.3270.

6-Methoxy-N,N-dimethyl-4-(piperazin-1-yl)-7-(3-(pyrrolidin-1yl)propoxy)quinazolin-2-amine (12)

To a solution of compound 11 (100 mg, 0.19 mmol) in 2 mL dry DCM 0.5 mL TFA was added at 0° C. and the reaction mixture was stirred at room temperature for 2 h. The reaction mixture was quenched by adding 2 (N) NaOH solution, then the mixture was extracted with DCM and washed the organic part with brine, dried over sodium sulphate, concentrating the organic part gives compound 12 as pure colourless solid (70 mg, 67% yield). EI-HRMS [M]$^+$: Calculated: 414.2743. Found: 414.2741.

General Procedure for the Synthesis of Compound 13a, 13b

To a solution of compound 12 (50 mg, 0.12 mmol) in 2 mL dry DCM, DIPEA (0.1 mL, 0.24 mmol) and 1.5 eqv of sulphonyl chloride were added keeping the reaction mixture in 0° C. Then it was stirred at room temperature for 4 hrs. Reaction mixture was washed with water and extracted in DCM. Concentrating the organic part gives a mixture. Purification using chloroform-methanol (15%) gives the corresponding compounds as solid.

General Procedure for the Synthesis of Compound 13c, 13f, 13h and 13i

Carboxylic acid (1.0 eqv.) was taken in 2 mL dry DMF followed by the addition of HATU/HBTU (1.5 eqv.) and DIPEA (1.5 eqv.). The reaction mixture was stirred at room temperature for 30 mins. Then compound 12 (50 mg, 0.12 mmol, 1.1 eqv.) in dry DMF was added. Reaction mixture at stirred at room temperature for overnight. The reaction mixture was extracted with ethyl acetate and washed with excess of water followed by brine wash; ethyl acetate part was dried with sodium sulphate and concentrated. The residue was purified by flash column to provide compound 13c, 13f, 13h, 13i.

General Procedure for the Synthesis of Compound 13d and 13g

To a solution of compound 12 (80 mg, 0.19 mmol) in dry toluene corresponding aldehydes (cyclopentanecarboxaldehyde and benzaldehyde, 2 eqv.) and activated molecular sieves (4A) were added and the reaction mixture was refluxed for 12 h. Toluene was removed in vacuum and dry DCE was added followed by the addition of Sodium triacetoxyborohydride (2 eqv.). This reaction mixture was stirred at room temperature for 4 h. Saturated NaHCO$_3$ solution was added and extracted with chloroform. The organic layer was washed with brine, dried over sodium sulphate and concentrated. The residue was purified by flash column to provide pure corresponding derivatives.

Procedure for the Synthesis of Compound 13e

To a solution of compound 12 (80 mg, 0.19 mmol) in 5 mL dry DMF bromocyclopentane (3.1 μL, 0.28 mmol) was added followed by the addition of potassium carbonate (58 mg, 0.38 mmol) and the reaction mixture was stirred at room temperature for 10 h. 50 mL water was added and extracted with ethylacetate. The organic layer was washed with brine, dried over sodium sulphate and concentrated. The residue was purified by flash column to provide compound 13e as gummy solid.

4-(4-(Isopropylsulfonyl)piperazin-1-yl)-6-methoxy-N,N-dimethyl-7-(3-(pyrrolidin-1-yl)propoxy)quinazolin-2-amine (13a)

$^1$H NMR (300 MHz, CDCl$_3$) δ 1.25 (br. s, 6H), 1.38 (d, J=5.49 Hz, 6H), 2.06 (br. s, 4H), 2.34 (br. s, 2H), 3.23 (br. s, 6H), 3.55 (br. s, 4H), 3.66 (br. s, 5H), 3.88 (br. s, 3H), 4.20 (br. s, 2H), 6.91 (br. s, 1H), 7.00 (br. s, 1H). EI-HRMS [M]$^+$: Calculated: 520.2832. Found: 520.2838.

4-(4-(Dimethylamino)-6-methoxy-7-(3-(pyrrolidin-1yl)propoxy)quinazolin-4-yl)-N,N-dimethylpiperazin-1-sulfonamide (13b)

$^1$H NMR (600 MHz, CDCl$_3$) δ 1.73-1.75 (m, 2H), 1.82 (br. s., 6H), 2.13-2.17 (m, 2H), 2.62 (br. s, 2H), 2.68-2.75 (m, 2H), 2.87 (s, 6H), 3.21 (s, 6H), 3.42-3.44 (m, 2H), 3.59-3.63 (m, 4H), 3.88 (s, 3H), 4.18-4.20 (m, 2H), 6.92 (s, 1H), 6.96 (s, 1H). EI-HRMS [M]$^+$: Calculated: 521.2784. Found: 521.2789.

Cyclopentyl-(4-(2-(dimethylamino)-6-methoxy-7-(3-(pyrrolidin-1-yl)propoxy)quinazolin-4-yl)piperazine-1yl)methanone (13c)

(35 mg, 55% yield). $^1$H NMR (300 MHz, CDCl$_3$) δ 1.60 (dd, J=7.16, 4.52 Hz, 2H), 1.75 (d, J=6.03 Hz, 2H), 1.86 (d, J=5.27 Hz, 8H), 2.21 (d, J=3.77 Hz, 1H), 2.59 (t, J=6.40 Hz, 2H), 2.74 (br. s, 2H), 2.81 (br. s, 2H), 2.93 (d, J=7.91 Hz, 2H), 3.22 (s, 6H), 3.57 (br. s, 4H), 3.74 (br. s, 2H), 3.83 (br. s, 2H), 3.89 (s, 3H), 4.19 (t, J=6.40 Hz, 2H), 6.96 (s, 2H). EI-HRMS [M]$^+$: Calculated: 510.3318. Found: 510.3311.

4-(4-(Cyclopentylmethyl)piperazin-1-yl)-6-methoxy-N,N-dimethyl-7-(3-(pyrrolidin-1yl)propoxy)quinazolin-2-amine (13d)

$^1$H NMR (300 MHz, CDCl$_3$) δ 1.20-1.28 (m, 2H), 1.58 (dd, J=17.05, 7.25 Hz, 5H), 1.81 (br. s, 6H), 2.13 (d, J=6.97 Hz, 2H), 2.34 (d, J=7.35 Hz, 2H), 2.56-2.63 (m, 8H), 2.66-2.71 (m, 2H), 3.16-3.26 (m, 6H), 3.51-3.63 (m, 4H), 3.91 (s, 3H), 4.17-4.22 (m, 2H), 6.94 (br. s, 1H), 6.99 (s, 1H). ESI [M+H]$^+$:497.73.

4-(4-(Cyclopentylpiperazin-1-yl)-6-methoxy-N,N-dimethyl-7-(3-(pyrrolidin-1yl)propoxy)quinazolin-2-amine (13e)

$^1$H NMR (300 MHz, CDCl$_3$) δ 1.40 (d, J=8.29 Hz, 2H), 1.43-1.55 (m, 2H), 1.64 (d, J=4.14 Hz, 2H), 1.77 (br. s, 6H), 2.08-2.14 (m, 2H), 2.48 (d, J=7.72 Hz, 1H), 2.55-2.64 (m, 8H), 2.67 (d, J=7.72 Hz, 2H), 3.14 (s, 6H), 3.54 (d, J=13.75 Hz, 4H), 3.81 (s, 3H), 4.12 (t, J=6.50 Hz, 2H), 6.86 (s, 1H), 6.94 (s, 1H). ESI [M+H]$^+$:483.55.

(4-(2-(Dimethylamino)-6-methoxy-7-(3-(pyrrolidin-1-yl)propoxy)quinazoline-4-yl)piperazin-1-yl)(phenyl)methanone (13e)

$^1$H NMR (600 MHz, CDCl$_3$) δ 1.86 (br. s, 4H), 2.15-2.19 (m, 2H), 2.75 (br. s, 4H), 2.83 (t, J=7.34 Hz, 2H), 3.19 (s, 6H), 3.45-3.70 (m, 8H), 3.86 (s, 3H), 4.18 (t, J=6.38 Hz, 2H), 6.94 (d, J=7.56 Hz, 2H), 7.42 (s, 5H). ESI [M+H]$^+$: 519.61.

4-(4-Benzylpiperazin-1-yl)-6-methoxy-N,N-dimethyl-7-(3-(pyrrolidin-1-yl)propoxy)quinazolin-2-amine (13g)

$^1$H NMR (600 MHz, CDCl$_3$) δ 1.79 (t, J=3.23 Hz, 4H), 2.09-2.15 (m, 2H), 2.55 (br. s, 4H), 2.62-2.67 (m, 6H), 3.20 (s, 6H), 3.58 (s, 2H), 3.58-3.63 (m, 4H), 3.86 (s, 3H), 4.17 (t, J=6.71 Hz, 2H), 6.96 (d, J=11.15 Hz, 2H), 7.25-7.28 (m, 1H), 7.31-7.37 (m, 4H). EI-HRMS [M]$^+$: 504.3198.

(4-(Aminomethyl)phenyl)(4-(2-(dimethylamino)-6-methoxy-7-(3-(pyrrolidin-1-yl)propoxy)quinazolin-4-yl)piperazin-1-yl)methanone (13h)

$^1$H NMR (300 MHz, CDCl$_3$) δ 1.81 (t, J=6.6 Hz, 4H), 2.08-2.17 (m, 4H), 2.57 (t, J=6 Hz, 4H), 2.68 (t, J=7.2 Hz, 2H), 3.20 (s, 6H), 3.54-3.64 (m, 6H), 3.87 (s, 3H), 3.93 (d, J=13.8 Hz, 2H), 4.19 (t, J=6.6 Hz, 2H), 6.94 (d, J=6.6 Hz, 2H), 7.36-7.43 (m, 4H). ESI [M+H]$^+$:548.40.

6-((4-(4-(2-(Dimethylamino)-6-methoxy-7-(3-(pyrrolidin-1-yl)propoxy)quinazolin-4-yl)piperazine-1-carbonyl)benzyl)amino)-6-oxohexanoic acid (13i)

$^1$H NMR (300 MHz, CDCl$_3$) δ 1.58-1.66 (m, 4H), 1.94 (t, J=6 Hz, 4H), 2.18-2.27 (m, 6H), 3.00 (t, J=9.9 Hz, 6H), 3.18 (s, 6H), 3.59 (br. s, 6H), 3.85 (s, 3H), 4.01 (br. s, 2H), 4.15 (t, J=6 Hz, 2H), 4.43 (d, J=6 Hz, 2H), 6.92 (d, J=6.3 Hz, 2H), 7.29-7.35 (m, 4H), 7.41 (br. s, 1H). ESI [M+H]$^+$:676.19

Example 3

SCHEME:3

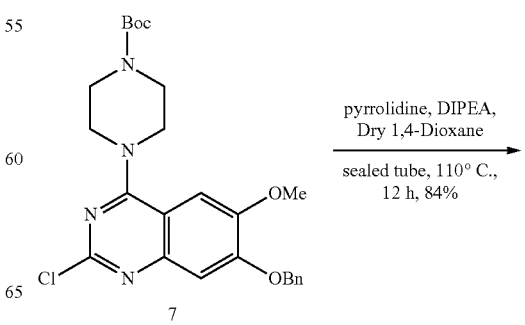

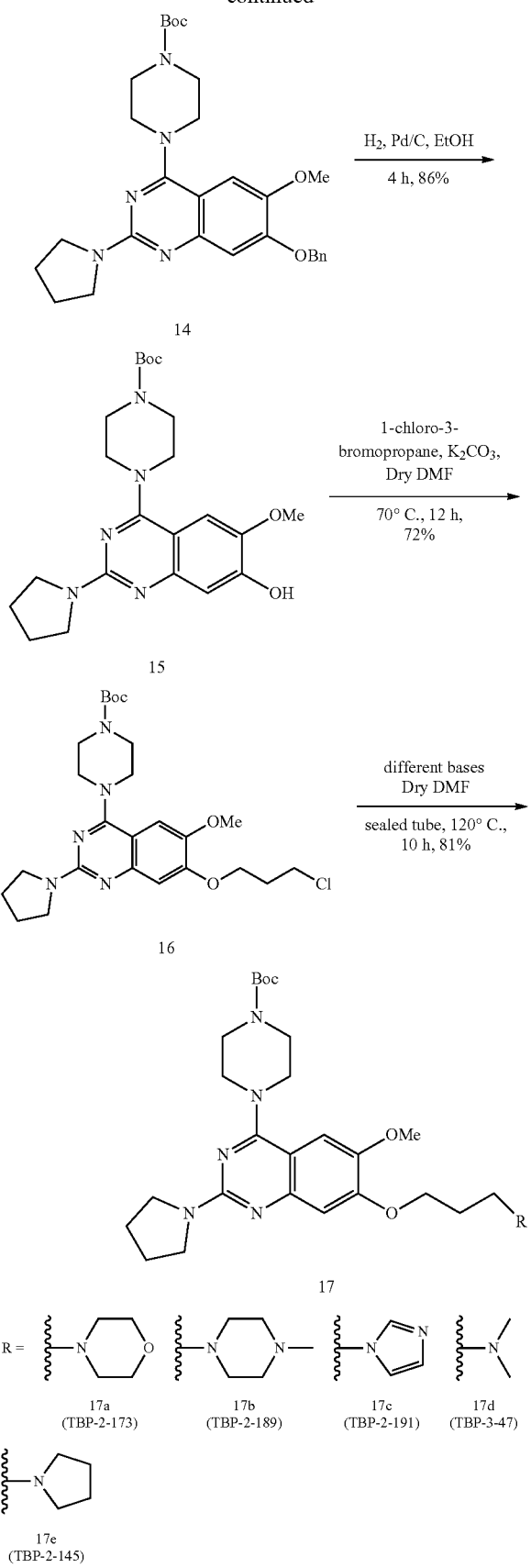

t-Butyl-4-(7-(benzyloxy)-6-methoxy-2-(pyrrolidin-1-yl)quinazoline-4-yl)piperazine-1-carboxylate (14)

Pyrrolidine (0.1 mL, 1.24 mmol was added to a solution of compound 7 (500 mg, 1.03 mmol) in dry 1,4-Dioxane (10 mL) and the reaction mixture was stirred for 12 h at 110° C. Dioxane was removed under vacuum, the residue then dissolved in ethyl acetate and the organic layer was washed with water and brine, dried and concentrated. The residue was purified by silica gel flash column chromatography, eluting with 30% ethyl acetate in hexane, to give compound to give compound 14 (459 mg, 84% yield) as a brown solid (m.p—188-190° C.). $^1$H NMR (600 MHz, CDCl$_3$) δ 1.49 (s, 9H), 1.96 (t, J=6.53 Hz, 4H), 3.54 (br. s, 4H), 3.60-3.63 (m, 8H), 3.89 (s, 3H), 5.22 (s, 2H), 6.98 (s, 1H), 7.04 (s, 1H), 7.31 (d, J=7.48 Hz, 1H), 7.37 (t, J=7.56 Hz, 2H), 7.46 (d, J=7.56 Hz, 2H); $^{13}$C NMR (75 MHz, CDCl$_3$) δ 28.40, 37.06, 49.59, 56.18, 70.48, 79.99, 104.47, 105.03, 106.94, 127.44, 128.01, 128.58, 136.22, 145.17, 153.91, 154.87, 164.74. EI-HRMS [M]$^+$: Calculated: 519.2846. Found: 519.2845.

t-Butyl-4-(7-hydroxy-6-methoxy-2-(pyrrolidin-1-yl)quinazoline-4-yl)piperazine-1-carboxylate (15)

10% Pd/C (50 mg) was added to a solution of compound 8 (500 mg, 0.96 mmol) in 10 Ml ethanol. A hydrogen balloon was attached and the mixture was stirred at room temperature for 3 hrs. The reaction mixture was filtered through celite and washed with methanol until the filtrate became colourless. The filtrate was concentrated and purified by column chromatography eluting by 8% methanol in Chloroform to provide compound 15 (345 mg, 82%) as yellowish green solid. $^1$H NMR (300 MHz, CDCl$_3$) δ 1.50 (s, 9H), 1.92 (br. s, 4H), 3.57 (br. s, 4H), 3.61 (br. s, 8H), 3.72 (s, 1H), 3.83 (s, 3H), 6.70 (br. s, 1H), 7.20 (s, 1H); $^{13}$C NMR (75 MHz, CDCl$_3$) δ 25.47, 28.43, 49.68, 55.60, 80.07, 103.06, 103.36, 106.97, 144.64, 149.46, 154.03, 154.82, 155.49, 164.36. EI-HRMS [M]$^+$: Calculated: 429.2376. Found: 429.2376.

t-Butyl-4-(7-(3-chloropropoxy)-6-methoxy-2-(pyrrolidin-1-yl)quinazoline-4-yl)piperazine-1-carboxylate (16)

Compound 15 (300 mg, 0.69 mmol) and potassium carbonate (194 mg, 1.39 mmol) was taken in dry DMF (5 mL). The reaction mixture was stirred at room temperature for 30 mins. Then 1-bromo-3-chloropropane (8.0 μL, 0.76 mmol) was added and the mixture was stirred at 110° C. for 12 h. The reaction mixture was extracted with ethyl acetate and washed with 50 mL of water followed by brine wash, dried with sodium sulphate and concentrated. The residue was purified by silica gel flash column chromatography, eluting with 2% methanol in chloroform, to give compound 16 (250 mg, 72%) as a colourless gummy solid. $^1$H NMR (300 MHz, CDCl$_3$) δ 1.50 (s, 9H), 1.97-2.02 (m, 4H), 2.33-2.39 (m, 2H), 3.60 (br. s, 4H), 3.62-3.68 (m, 8H), 3.79 (t, J=6.22 Hz, 2H), 3.90 (s, 3H), 4.26-4.32 (m, 2H), 6.98 (s, 1H), 7.07-7.16 (m, 1H); $^{13}$C NMR (75 MHz, CDCl$_3$) δ 56.06, 25.48, 28.35, 29.80, 31.85, 46.54, 49.54, 85.11, 79.81, 104.58, 105.10, 106.45, 144.69, 151.54, 153.75, 154.78, 157.00, 164.71. EI-HRMS [M]$^+$: Calculated: 505.2456. Found: 505.2456.

General Procedure for the Synthesis of Compounds 17 Series

To a solution of compound 16 (150 mg, 0.29 mmol) in 2 mL dry DMF in a sealed tube corresponding base 1.1 eqv was added and the reaction mixture was heated at 90° C. for 10 h. The reaction mixture was extracted with ethyl acetate and washed with 50 mL of water followed by brine wash; ethyl acetate part was dried with sodium sulphate and concentrated. The residue was purified by silica gel flash column chromatography.

t-Butyl-4-(6-methoxy-7-(3-morpholinpropoxy)-2-(pyrrolidin-1-yl)quinazoline-4-yl)piperazine-1-carboxylate (17a)

Compound (17a) was prepared by the same procedure as 17 as white solid. $^1$H NMR (300 MHz, CDCl$_3$) δ 1.49 (s, 9H), 1.98 (t, J=6.40 Hz, 6H), 2.05-2.11 (m, 3H), 2.47 (br. s, 4H), 2.53 (s, 2H), 3.56 (br. s, 4H), 3.60-3.64 (m, 7H), 3.71-3.74 (m, 4H), 3.89 (s, 3H), 4.20 (t, J=6.59 Hz, 2H), 6.96 (s, 1H), 7.27 (s, 1H). EI-HRMS [M]$^+$: Calculated: 556.3373 Found: 556.3375.

t-Butyl-4-(6-methoxy-7-(3-(4-methylpiperazin-1-yl)propoxy)-2-(pyrrolidin-1-yl)quinazoline-4-yl)piperazine-1-carboxylate (17b)

$^1$H NMR (600 MHz, CDCl$_3$) δ 1.48 (s, 9H), 1.95-1.97 (m, 4H), 2.05-2.08 (m, 2H), 2.28 (s, 3H), 2.39-2.50 (m, 4H), 2.52 (t, J=7.12 Hz, 4H), 3.53 (br. s, 4H), 3.59-3.64 (m, 10H), 3.87 (s, 3H), 4.17 (t, J=6.71 Hz, 2H), 6.95 (s, 1H), 6.97 (s, 1H). EI-HRMS [M]$^+$: Calculated: 569.3690. Found: 569.3694.

t-Butyl-4-(7-(3-(1H-imidazol-1-yl)propoxy)-6-methoxy-2-(pyrrolidin-1-yl)quinazolin-4-yl)piperazine-1-carboxylate (17c)

$^1$H NMR (300 MHz, CDCl$_3$) δ 1.47 (s, 9H), 1.96 (br. s, 4H), 2.26-2.37 (m, 2H), 3.60 (br. s, 12H), 3.89 (s, 3H), 4.07 (t, J=5.56 Hz, 2H), 4.20 (t, J=6.59 Hz, 2H), 6.93 (br. s, 1H), 6.96 (s, 1H), 7.03 (br. s, 1H), 7.06-7.13 (m, 1H), 7.50 (br. s, 1H). ESI [M+H]$^+$:538.46.

t-Butyl-4-(7-(3-(1H-imidazol-1-yl)propoxy)-6-methoxy-2-(pyrrolidin-1-yl)quinazoline-4-yl)piperazine-1-carboxylate (17d)

$^1$H NMR (300 MHz, CDCl$_3$) δ 1.50 (s, 9H), 2.00 (br. s, 4H), 2.31-2.39 (m, 2H), 3.66 (d, J=10.98 Hz, 12H), 3.91 (s, 3H), 4.12 (d, J=5.49 Hz, 2H), 4.22 (t, J=6.49 Hz, 2H), 6.93-7.12 (m, 3H), 7.51 (br. s, 2H). ESI [M+H]$^+$:515.71.

t-Butyl-4-(6-methoxy-2-(pyrrolidin-1-yl)-7-(3-(pyrrolidin-1-yl)propoxy)quinazolin-4-yl)piperazine-1-carboxylate (17e)

$^1$H NMR (300 MHz, CDCl$_3$) δ 1.49 (s, 9H), 1.92 (br. s, 4H), 1.98 (br. s, 4H), 2.23-2.29 (m, 2H), 2.81-2.94 (m, 8H), 3.30 (br. s, 2H), 3.60 (d, J=4.90 Hz, 4H), 3.65 (br. s, 4H), 3.88 (s, 3H), 4.21 (t, J=6.40 Hz, 2H), 6.96 (s, 1H), 7.12 (s, 1H). ESI [M+H]$^+$:541.66.

Example 4

SCHEME:4

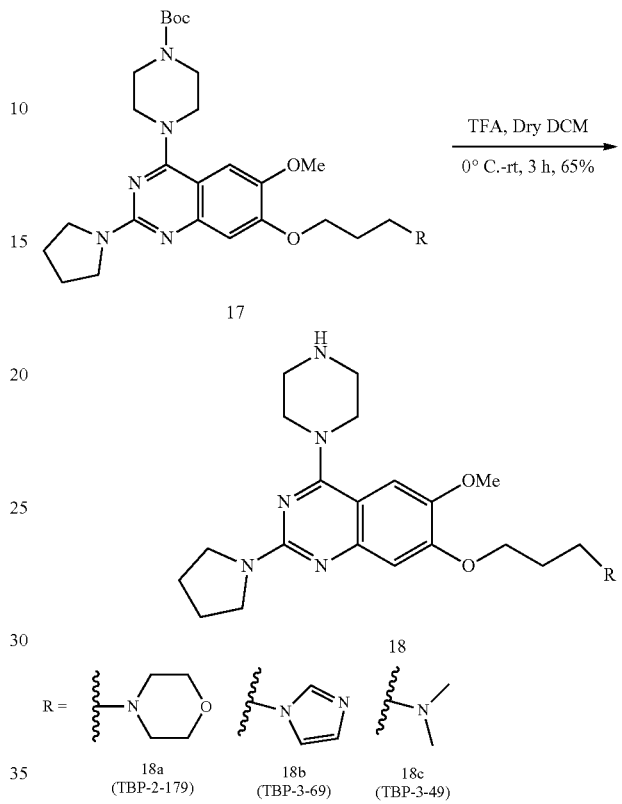

General Procedure for Boc-Deprotection

To a solution of compound 17 (100 mg, 0.19 mmol) in 2 mL dry DCM 0.5 mL TFA was added at 0° C. and the reaction mixture was stirred at room temperature for 2 hrs. The reaction mixture was quenched by adding 2 (N) NaOH solution, then the mixture was extracted with DCM and washed the organic part with brine, dried over sodium sulphate, concentrating the organic part gives compound 18.

4-(3-(6-Methoxy-4-(piperazin-1-yl)-2-(pyrrolidin-1-yl)quinazolin-7-yloxy)propyl)morpholine (18a)

(150 mg, 0.27 mmol) of compound 17a was taken in 3 mL dry 1,4-dioxane. Then the reaction mixture was cooled to 0° C. and 1 ml 4N HCl was added. A ppt was formed which was filtered and the precipitate was the chloride salt of compound 18. $^1$H NMR (300 MHz, CD$_3$OD) δ2.03-2.24 (m, 4H), 2.36-2.52 (m, 2H), 3.21-3.35 (m, 4H), 3.44-3.55 (m, 6H), 3.64-3.83 (m, 6H), 3.88-3.95 (m, 2H), 3.99 (s, 2H), 4.10 (br. s, 2H), 4.28 (br. s, 3H), 4.37 (t, J=5.27 Hz, 2H), 7.28 (s, 1H), 7.40 (s, 1H). ESI [M+H]$^+$:457.31

7-(3-(1H-Imidazol-1-yl)propoxy)-6-methoxy-4-(piperazin-1-yl)-2-(pyrrolidin-1-yl)quinazoline (18b)

$^1$H NMR (600 MHz, CDCl$_3$) δ 1.97 (t, J=3.19 Hz, 4H), 2.12-2.15 (m, 1H), 2.33 (t, J=6.13 Hz, 2H), 3.07 (d, J=5.21 Hz, 2H), 3.57-3.59 (m, 4H), 3.62-3.65 (m, 4H), 3.87-3.90

(m, 2H), 3.91 (s, 3H), 4.07 (t, J=5.87 Hz, 2H), 4.22 (t, J=6.75 Hz, 2H), 6.93-6.94 (m, 1H), 6.97 (s, 1H), 7.00 (s, 1H), 7.04 (s, 1H), 7.49 (s, 1H). EI-HRMS [M]+: Calculated 437.2539. Found: 437.2539.

3-((6-Methoxy-4-(piperazin-1-yl)-2-(pyrrolidin-1-yl) quinazolin-7-yl)oxy)-N,N-dimethylpropan-1-amine (18c)

$^1$H NMR (300 MHz, CDCl$_3$) δ 1.91-2.55 (m, 4H), 2.04-2.13 (m, 2H), 2.26 (s, 6H), 2.45-2.50 (m, 2H), 3.06 (d, J=3.66 Hz, 4H), 3.56 (d, J=4.03 Hz, 4H), 3.61-3.67 (m, 4H), 3.89 (s, 3H), 4.17 (t, J=6.77 Hz, 2H), 6.99 (s, 1H), 7.01 (s, 1H). EI-HRMS [M]+: Calculated: 414.2743. Found: 414.2743.

Example 5

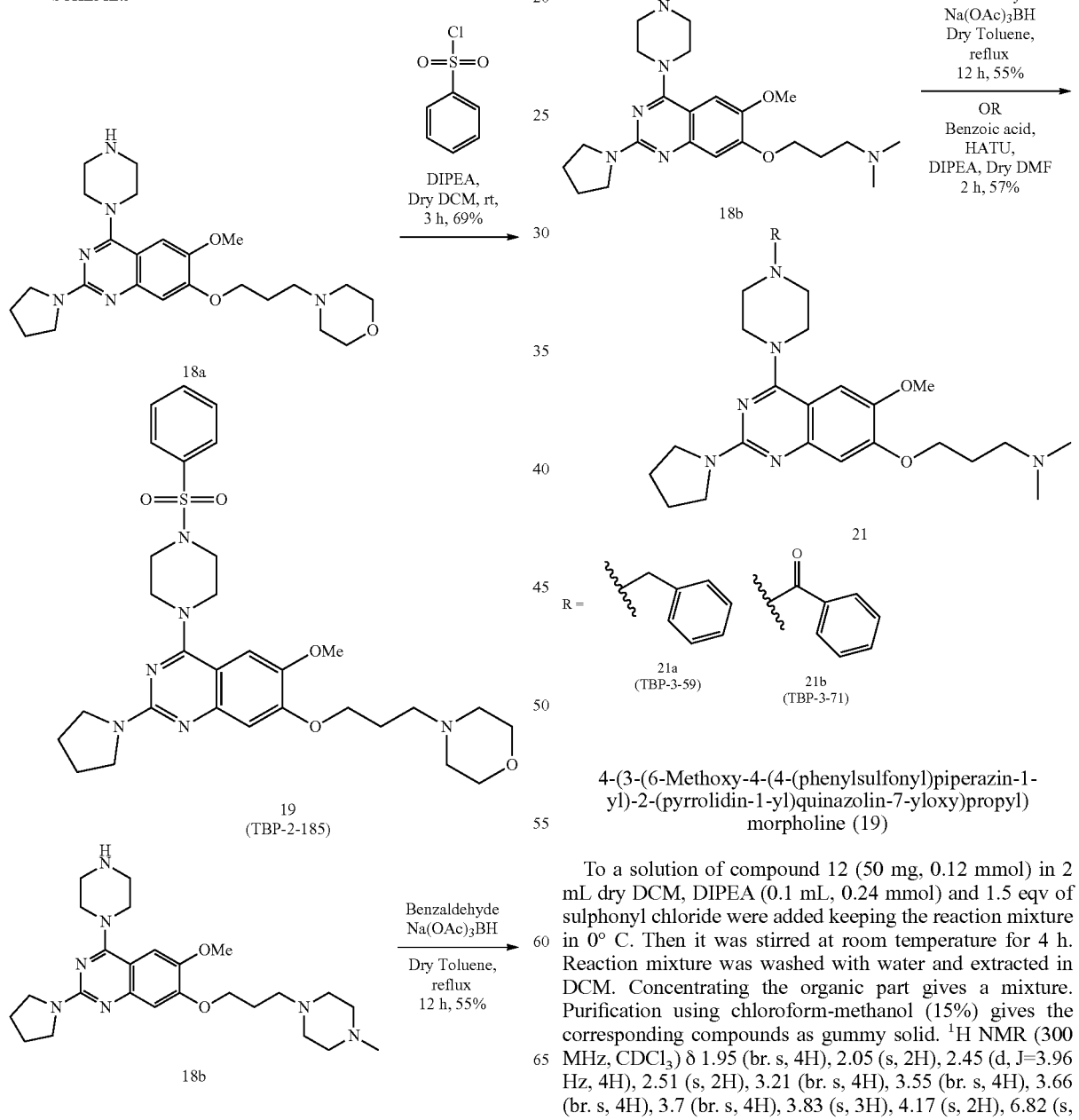

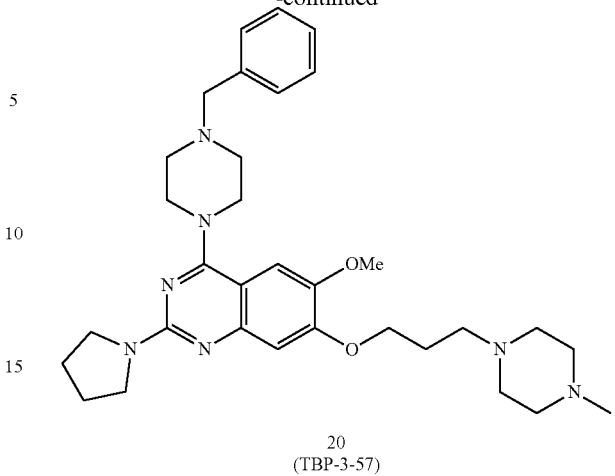

4-(3-(6-Methoxy-4-(4-(phenylsulfonyl)piperazin-1-yl)-2-(pyrrolidin-1-yl)quinazolin-7-yloxy)propyl) morpholine (19)

To a solution of compound 12 (50 mg, 0.12 mmol) in 2 mL dry DCM, DIPEA (0.1 mL, 0.24 mmol) and 1.5 eqv of sulphonyl chloride were added keeping the reaction mixture in 0° C. Then it was stirred at room temperature for 4 h. Reaction mixture was washed with water and extracted in DCM. Concentrating the organic part gives a mixture. Purification using chloroform-methanol (15%) gives the corresponding compounds as gummy solid. $^1$H NMR (300 MHz, CDCl$_3$) δ 1.95 (br. s, 4H), 2.05 (s, 2H), 2.45 (d, J=3.96 Hz, 4H), 2.51 (s, 2H), 3.21 (br. s, 4H), 3.55 (br. s, 4H), 3.66 (br. s, 4H), 3.7 (br. s, 4H), 3.83 (s, 3H), 4.17 (s, 2H), 6.82 (s, 1H), 6.95 (s, 1H), 7.61-7.54 (m, 3H), 7.80-7.77 (m, 2H). EI-HRMS [M]⁺: Calculated: 596.2781 Found: 596.2785.

4-(4-Benzylpiperazin-1yl)-6-methoxy-7-(3-(4-methylpiperazin-1-yl)propoxy)-2-(pyrrolidin-1-yl) quinazoline (20)

Compound 20 was prepared by the same procedure as 13d. $^1$H NMR (300 MHz, CDCl$_3$) δ 1.96 (t, J=6.40 Hz, 4H), 2.06 (d, J=6.78 Hz, 2H), 2.29 (s, 3H) 2.35 (d, J=7.72 Hz, 4H), 2.56-2.50 (m, 6H), 2.66-2.61 (m, 4H), 3.65-3.57 (m, 10H), 3.87 (s, 3H), 4.17 (t, J=6.69 Hz, 2H), 6.96 (s, 1H), 6.98 (s, 1H), 7.40-7.28 (m, 5H). EI-HRMS [M]⁺: Calculated: 559.3635. Found: 559.3641.

3-(4-(4-Benzylpiperazin-1-yl)-6-methoxy-2-(pyrrolidin-1-yl)quinazolin-7-yloxy)-N,N-dimethylpropan-1-amine (21a)

Compound 21a was prepared by the same procedure as 13g. $^1$H NMR (600 MHz, CDCl$_3$) δ 1.79 (t, J=3.23 Hz, 4H), 2.15-2.09 (m, 2H), 2.55 (br. s, 4H), 2.67-2.62 (m, 6H), 3.20 (s, 6H), 3.58 (s, 2H), 3.63-3.58 (m, 4H), 3.86 (s, 3H), 4.17 (t, J=6.71 Hz, 2H), 6.96 (d, J=11.15 Hz, 2H), 7.28-7.25 (m, 1H), 7.37-7.31 (m, 4H). EI-HRMS [M]⁺: Calculated: 504.3213. Found: 504.3198.

(4-(7-(3-(Dimethylamino)propoxy)-6-methoxy-2-(pyrrolidin-1-yl)quinazolin-4-yl)piperazin-1-yl)(phenyl)methanone (21b)

Compound 21b was prepared by the same procedure as 13c. $^1$H NMR (300 MHz, CDCl$_3$) δ 1.97 (d, J=4.52 Hz, 4H), 2.14-2.05 (m, 2H), 2.30 (s, 6H), 2.54 (t, J=7.25 Hz, 2H), 3.62 (d, J=6.22 Hz, 8H), 3.87 (s, 3H), 4.04-3.88 (m, 4H), 4.16 (t, J=6.50 Hz, 2H), 6.94 (s, 1H), 7.01 (s, 1H), 7.43 (s, 5H). ESI [M+H]⁺:519.61.

Example 6

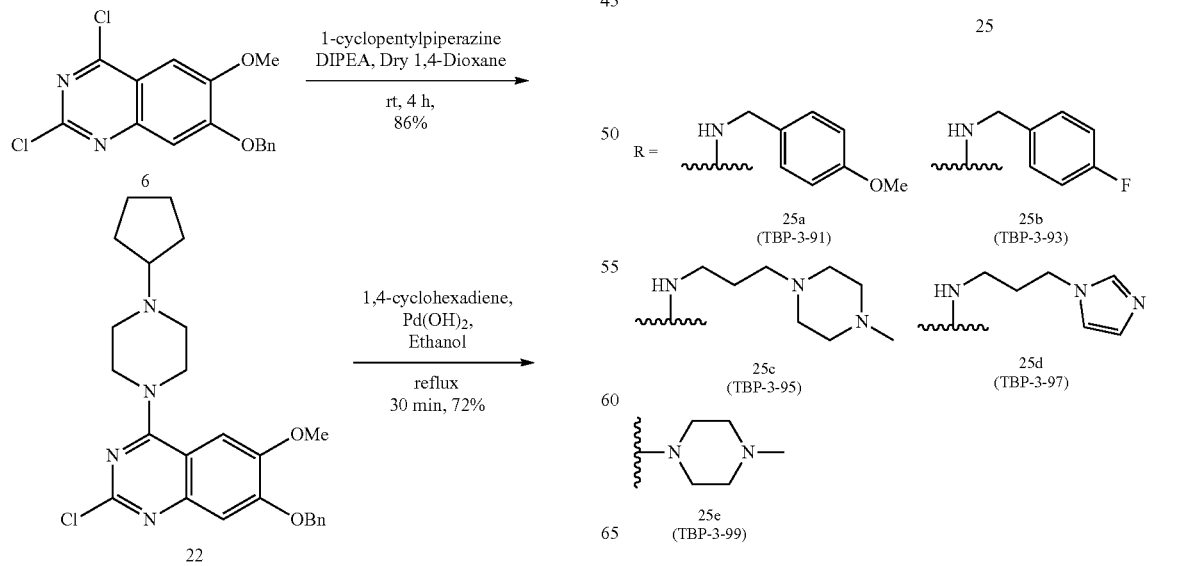

7-(Benzyloxy)-2-chloro-4-(4-cyclopentylpiperazin-1-yl)-6-methoxyquinazoline (22)

1-cyclopentyl Piperazine (507 mg, 0.003 mmol) was added to a stirred solution of 6 (1 g, 0.0029 mmol) in dry 1,4-Dioxane and DIPEA (0.7 mL, 0.005 mmol). The solution was stirred for 4 h at room temperature. After adding water a precipitate was formed which was filtered to give compound 7 (1.1g, 86% yield) as white solid (m.p—156-159° C.). $^1$H NMR (300 MHz, CDCl$_3$) δ 1.39-1.50 (m, 2H), 1.58 (dd, J=7.72, 4.71 Hz, 2H), 1.68-1.75 (m, 2H), 1.88 (br. s, 2H), 2.51-2.60 (m, 1H), 2.64-2.70 (m, 4H), 3.66-3.71 (m, 1H), 3.76-3.82 (m, 4H), 3.96 (s, 3H), 5.25 (s, 2H), 7.06 (s, 1H), 7.18 (s, 1H), 7.31-7.41 (m, 3H), 7.42-7.48 (m, 2H). ESI [M+H]$^+$:453.40.

2-Chloro-4-(4-cyclopentylpiperazin-1-yl)-6-methoxyquinazolin-7-ol (23)

Pd(OH)$_2$ (50 mg) was added to a solution of compound 22 (500 mg, 1.12 mol) and 1,4-cyclohexadiene (3 mL, 2.21 mol) in 20 mL Ethanol. Reaction mixture was heated at 70° C. for 30 min. The reaction mixture was filtered through celite and washed with methanol until the filtrate became colourless. The solution was concentrated to provide compound 23 (300 mg, 72% yield) as pale yellow solid (m.p—135° C.). $^1$H NMR (300 MHz, CDCl$_3$) δ 1.43-1.61 (m, 4H), 1.66-1.74 (m, 2H), 1.88 (d, J=7.54 Hz, 2H), 2.57-2.65 (m, 1H), 2.65-2.81 (m, 4H), 3.64-3.85 (m, 4H), 3.95 (s, 3H), 7.01 (s, 1H), 7.17 (s, 1H). ESI [M+H]$^+$: 363.22.

2-Chloro-4-(4-cyclopentylpiperazin-1-yl)-6-methoxy-7-(3-(pyrrolidin-1yl)propoxy)quinazoline (24)

Compound 23 (200 mg, 0.55 mmol) and potassium carbonate (153 mg, 1.1 mmol) was taken in dry DMF (5 mL). The reaction mixture was stirred at room temperature for 30 min. Then 1-(3-chloropropyl)pyrrolidine (121.8 mg, 0.0825 mmol) was added and the mixture was stirred at 120° C. for 2 h. The reaction mixture was extracted with ethyl acetate and washed with 50 mL of water followed by brine wash, dried with sodium sulphate and concentrated. The residue was purified by flash column chromatography, eluting with 2% methanol in chloroform, to give compound 24 (170 mg, 79%) as a colourless gummy solid. $^1$H NMR (300 MHz, CDCl$_3$) δ 1.37-1.51 (m, 2H), 1.52-1.64 (m, 2H), 1.66-1.76 (m, 2H), 1.83 (d, J=3.01 Hz, 4H), 1.88 (br. s, 2H), 2.10-2.22 (m, 2H), 2.50-2.59 (m, 1H), 2.60-2.71 (m, 8H), 2.71-2.76 (m, 2H), 3.77 (d, J=4.52 Hz, 4H), 3.93 (s, 3H), 4.19 (t, J=6.40 Hz, 2H), 7.04 (s, 1H), 7.14 (s, 1H). ESI [M+H]$^+$: 474.63.

General Procedure for the Synthesis of Compound 25

Compound 24 (80 mg, 0.17 mmol) and K$_2$CO$_3$ (93.9 mg, 0.68 mmol) were taken in dry 1,4-dioxane in a sealed tube followed by the addition of corresponding amines (1.1 eqv.). Reaction mixture was heated at 120° C. for 24 h. 1,4-dioxane was removed under vacuum. The residue was extracted with chloroform and washed with 50 mL of water followed by brine wash, dried with sodium sulphate and concentrated and purified by flash column chromatography, eluting with Chloroform-CMA (Chloroform-methanol-5% NH$_3$), to give corresponding derivatives.

4-(4-Cyclopentylpiperazin-1-yl)-6-methoxy-N-(4-methoxybenzyl)-7-(3-(pyrrolidin-1-yl)propoxy)quinazolin-2-amine (25a)

$^1$H NMR (600 MHz, CDCl$_3$) δ 1.43-1.46 (m, 2H), 1.59 (d, J=5.46 Hz, 2H), 1.74 (m, 2H), 1.86 (br. s, 4H), 1.90 (br. s., 2H), 2.16-2.20 (m, 2H), 2.55 (dt, J=15.91, 7.94 Hz, 1H), 2.62-2.70 (m, 6H), 2.76 (t, J=7.26 Hz, 2H), 2.81-2.85 (m, 1H), 3.03 (s, 1H), 3.71 (br. s, 4H), 3.81 (s, 3H), 3.90 (s, 3H), 4.09-4.12 (m, 1H), 4.21 (t, J=6.33 Hz, 2H), 4.61 (d, J=4.89 Hz, 2H), 6.87 (d, J=8.33 Hz, 2H), 6.97 (s, 1H), 7.00 (s, 1H), 7.32 (d, J=8.21 Hz, 2H). ESI [M+H]$^+$:575.68

4-(4-Cyclopentylpiperazin-1-yl)-N-(4-fluorobenzyl)-6-methoxy-7-(3-(pyrrolidin-1-yl)propoxy)quinazolin-2-amine (25b)

$^1$H NMR (300 MHz, CDCl$_3$) δ 1.41-1.50 (m, 2H), 1.56-1.63 (m, 2H), 1.73 (d, J=4.03 Hz, 2H), 1.76-1.86 (m, 4H), 1.89 (m, 2H), 2.13-2.19 (m, 2H), 2.55-2.62 (m, 4H), 2.66 (d, J=5.49 Hz, 4H), 2.68-2.72 (m, 2H), 3.50 (q, J=6.95 Hz, 1H), 3.59-3.69 (m, 4H), 3.91 (s, 3H), 4.20 (t, J=6.59 Hz, 2H), 4.65 (d, J=5.12 Hz, 2H), 6.94 (s, 1H), 6.97-7.04 (m, 3H), 7.32-7.39 (m, 2H). ESI [M+H]$^+$:563.46.

4-(4-Cyclopentylpiperazin-1-yl)-6-methoxy-N-(3-(4-methylpiperazin-1-yl)propyl)-7-(3-(pyrrolidin-1-yl)propoxy)quinazolin-2-amine (25c)

$^1$H NMR (300 MHz, CDCl$_3$) δ 1.43-1.51 (m, 2H), 1.57-1.62 (m, 2H), 1.70-1.75 (m, 2H), 1.81 (d, J=4.03 Hz, 4H), 1.84-1.91 (m, 2H), 2.10-2.19 (m, 4H), 2.31 (s, 3H), 2.52 (dd, J=13.72, 6.40 Hz, 12H), 2.63-2.72 (m, 8H), 3.41 (dd, J=11.71, 5.85 Hz, 1H), 3.50-3.56 (m, 2H), 3.59-3.66 (m, 4H), 3.90 (s, 3H), 4.19 (t, J=6.77 Hz, 2H), 6.92-6.96 (m, 1H), 7.00 (s, 1H). ESI [M+H]$^+$:595.52.

N-(3-(1H-Imidazol-1-yl)propyl)-4-(4-cyclopentylpiperazin-1-yl)-6-methoxy-7-(3-(pyrrolidin-1-yl)propoxy)quinazolin-2-amine (25d)

$^1$H NMR (300 MHz, CDCl$_3$) δ 1.44 (d, J=8.29 Hz, 2H), 1.60 (m, 2H), 1.73 (m, 2H), 1.83 (m, 4H), 1.91 (m, 2H), 2.07-2.18 (m, 4H), 2.30 (d, J=6.03 Hz, 4H), 2.56-2.73 (m, 8H), 3.48 (d, J=6.03 Hz, 3H), 3.66 (br. s, 4H), 3.85-3.94 (m, 3H), 4.09 (t, J=6.78 Hz, 2H), 4.20 (t, J=6.59 Hz, 2H), 6.92 (s, 1H), 6.98 (d, J=6.03 Hz, 2H), 7.06 (s, 1H), 7.53 (s, 1H). ESI [M+H]$^+$:563.40.

4-(4-Cyclopentylpiperazin-1-yl)-6-methoxy-2-(4-methylpiperazin-1-yl)-7-(3-(pyrrolidin-1-yl)propoxy)quinazoline (25e)

$^1$H NMR (300 MHz, CDCl$_3$) δ 1.38-1.50 (m, 2H), 1.51-1.63 (m, 2H), 1.65-1.74 (m, 2H), 1.74-1.81 (m, 4H), 1.87-1.93 (m, 2H), 2.12 (dd, J=14.18, 7.04 Hz, 2H), 2.22-2.30 (m, 2H), 2.33 (s, 3H), 2.48 (d, J=4.57 Hz, 4H), 2.53 (br. s, 4H), 2.62 (d, J=7.68 Hz, 2H), 2.66 (d, J=5.12 Hz, 4H), 2.85-2.91 (m, 1H), 3.45 (s, 1H), 3.60 (br. s, 3H), 3.85 (br. s, 2H), 3.87 (s, 3H), 4.16 (t, J=6.59 Hz, 2H), 6.92 (s, 1H), 6.97 (s, 1H). ESI [M+H]$^+$:538.62.

Example 7
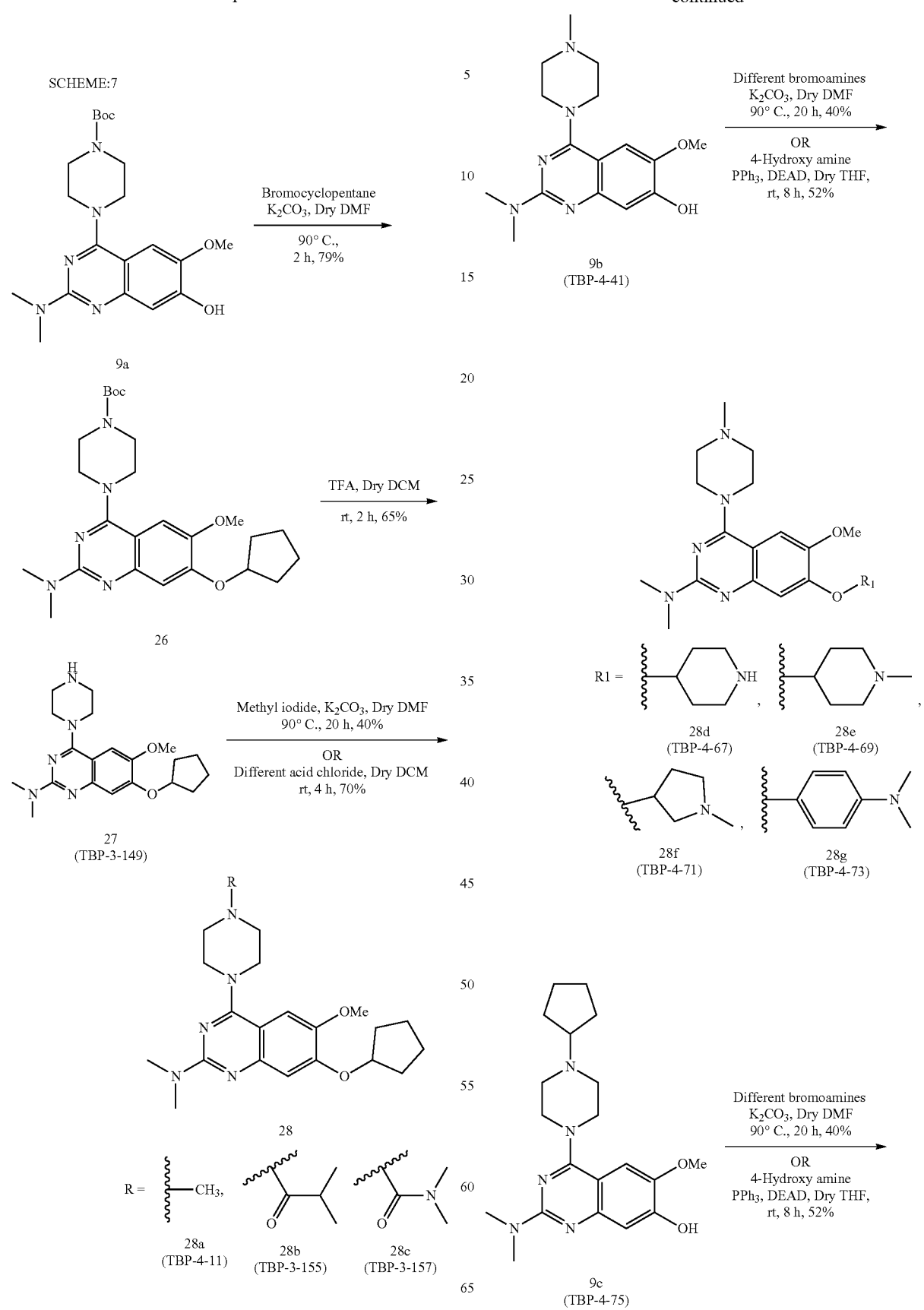

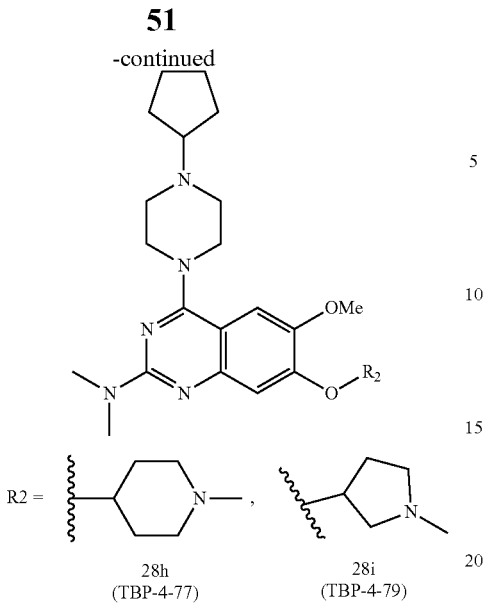

28h (TBP-4-77)    28i (TBP-4-79)

t-Butyl-4-(2-(dimethylamino)-7-hydroxy-6-methoxyquinazolin-4-yl)piperazine-1-carboxylate (26)

Compound 26 was synthesized according to the procedure of compound 10 was synthesized as a yellow solid. $^1$H NMR (300 MHz, CDCl$_3$) δ 1.50 (s, 9H), 1.58-1.66 (m, 2H), 1.81-1.87 (m, 2H), 1.20-1.95 (m, 2H), 2.04-2.08 (m, 2H), 3.23 (s, 6H), 3.52-3.56 (m, 4H), 3.61-3.65 (m, 4H), 3.87 (s, 3H), 4.89-4.94 (m, 1H), 6.96 (s, 2H). ESI [M+H]$^+$:472.37.

7-(Cyclopentyloxy)-6-methoxy-N,N-dimethyl-4-(piperazin-1-yl)quinazolin-2-amine (27)

Compound 27 was synthesized in the same way as compound 12 was synthesized. $^1$H NMR (300 MHz, CDCl$_3$) δ 1.62-1.67 (m, 2H), 1.81-1.86 (m, 2H), 1.90-1.97 (m, 2H), 2.04-2.08 (m, 2H), 2.98-3.00 (m, 1H), 3.12 (t, J=9 Hz, 4H), 3.23 (s, 6H), 3.62 (t, J=9 Hz, 4H), 3.86 (s, 3H), 6.95 (s, 1H), 7.00 (s, 1H). ESI [M+H]$^+$:372.35.

7-(Cyclopentyloxy)-6-methoxy-N,N-dimethyl-4-(4-methylpiperazin-1-yl)quinazolin-2-amine (28a)

Compound 28a was synthesized in the same way as compound 13a and 13b was synthesized. $^1$H NMR (300 MHz, CDCl$_3$) δ 1.61-1.66 (m, 2H), 1.81-1.86 (m, 2H), 1.90-1.97 (m, 2H), 2.02-2.11 (m, 2H), 2.37 (s, 3H), 2.62 (t, J=9 Hz, 4H), 3.23 (s, 6H), 3.65 (t, J=9 Hz, 4H), 3.87 (s, 3H), 4.89-4.94 (m, 1H), 6.97 (s, 1H), 7.00 (s, 1H). ESI [M+H]$^+$: 386.43.

1-(4-(7-(Cyclopentyloxy)-2-(dimethylamino)-6-methoxyquinazolin-4-yl)piperazin-1-yl)-2-methyl-propan-1-one (28b)

Compound 28b was synthesized according to the procedure of compound 13a and 13b was synthesized. $^1$H NMR (300 MHz, CDCl$_3$) δ 1.15 (s, 3H), 1.17 (s, 3H), 1.61-1.66 (m, 2H), 1.81-1.86 (m, 2H), 1.90-2.01 (m, 2H), 2.01-2.08 (m, 2H), 2.80-2.89 (m, 1H), 3.22 (s, 6H), 3.54-3.60 (m, 4H), 3.73 (t, J=9 Hz, 2H), 3.83 (t, J=9 Hz, 2H), 3.87 (s, 3H), 4.90-4.92 (m, 1H), 6.93 (s, 1H), 6.95 (s, 1H). ESI [M+H]$^+$: 442.40.

4-(7-(Cyclopentyloxy)-2-(dimethylamino)-6-methoxyquinazolin-4-yl)-N,N-dimethylpiperazine-1-carboxamide (28c)

Compound 28c was synthesized in the same way as compound 13a and 13b was synthesized. $^1$H NMR (300 MHz, CDCl$_3$) δ 1.61-1.65 (m, 2H), 1.80-1.87 (m, 2H), 1.90-1.97 (m, 2H), 2.03-2.07 (m, 2H), 2.88 (s, 6H), 3.21 (s, 6H), 3.41-3.44 (m, 4H), 3.55-3.59 (m, 4H), 3.86 (s, 3H), 4.88-4.93 (m, 1H), 6.92 (s, 1H), 6.96 (s, 1H). ESI [M+H]$^+$: 443.36.

Example 8

SCHEME:8

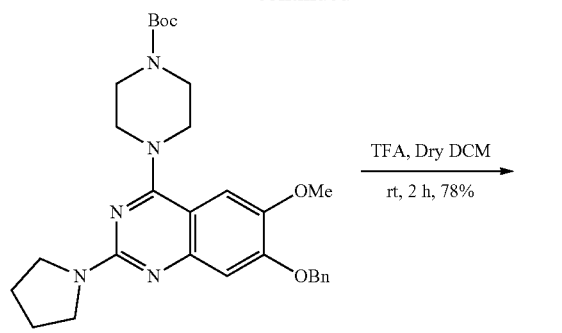

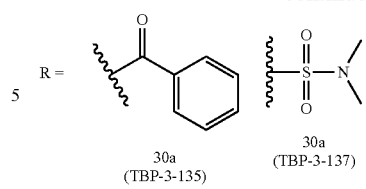

7-(Benzyloxy)-6-methoxy-N,N-dimethyl-4-(piperazin-1-yl)quinazolin-2-amine (29a)

Compound 29a was synthesized according to the procedure of compound 12. ¹H NMR (300 MHz, CDCl₃) δ 2.39 (s, 2H), 3.13 (t, J=9 Hz, 2H), 3.23 (s, 6H), 3.63 (t, J=9 Hz, 4H), 3.92 (s, 3H), 5.25 (s, 2H), 7.00 (s, 1H), 7.08 (s, 1H), 7.31-7.43 (m, 3H), 7.50 (d, J=9 Hz, 2H). ESI [M+H]⁺: 394.42.

(4-(7-(Benzyloxy)-2-(dimethylamino)-6-methoxyquinazolin-4-yl)piperazin-1-yl)(phenyl)methanone (30a)

Compound 30a was synthesized in the same way as described for compound 13c and 13f. ¹H NMR (300 MHz, CDCl₃) δ 3.23 (s, 6H), 3.68 (br. s, 8H), 3.91 (s, 3H), 5.25 (s, 2H), 6.99 (s, 1H), 7.05 (s, 1H), 7.34-7.51 (m, 10H). ESI [M+H]⁺:498.35.

4-(7-(Benzyloxy)-2-(dimethylamino)-6-methoxyquinazolin-4-yl)-N,N-dimethylpiperazine-1-sulfonamide (30b)

Compound 30b was synthesized according to the procedure of compound 13a and 13b. ¹H NMR (300 MHz, CDCl₃) δ 2.87 (s, 6H), 3.21 (s, 6H), 3.44 (t, J=9 Hz, 4H), 3.62 (t, J=9 Hz, 4H), 3.90 (s, 3H), 5.23 (s, 2H), 6.95 (s, 1H), 7.02 (s, 1H), 7.32-7.41 (m, 3H), 7.46-7.49 (m, 2H). ESI [M+H]⁺:501.42.

7-(Benzyloxy)-6-methoxy-4-(piperazin-1-yl)-2-(pyrrolidin-1-yl)quinazoline (30c)

Compound 30c was synthesized in the same way as compound 12 was synthesized. ¹H NMR (300 MHz, CDCl₃) δ 1.85-1.88 (m, 2H), 3.17-3.19 (m, 2H), 3.47 (t, J=9 Hz, 3H), 3.73-3.78 (m, 3H), 4.12 (s, 8H), 5.10 (s, 2H), 6.88 (s, 1H), 7.00 (s, 1H), 7.20-7.25 (m, 5H), 7.28-7.33 (m, 5H). ESI [M+H]⁺:524.47.

(4-(7-(Benzyloxy)-6-methoxy-2-(pyrrolidin-1-yl)quinazolin-4-yl)piperazin-1-yl)(phenyl)methanone (31)

Compound 31 was synthesized in the same way as compound 13a and 13b was synthesized. ¹H NMR (300 MHz, CDCl₃) δ 1.97 (t, J=6 Hz, 4H), 3.66 (t, J=6.3 Hz, 12H), 3.87 (s, 3H), 6.88 (s, 1H), 7.31 (s, 1H), 7.45 (s, 5H). EI-HRMS [M]⁺: Calculated: 433.2114. Found: 433.2115.

Example 9

SCHEME:9

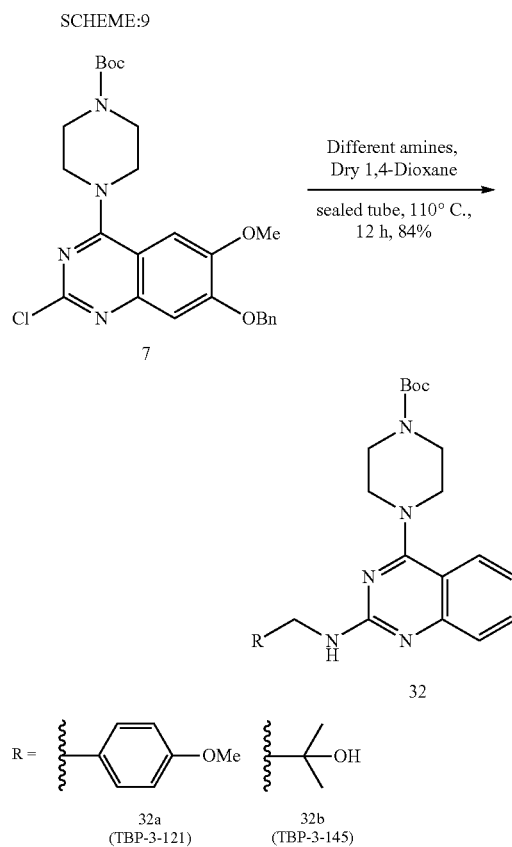

t-Butyl-4-(7-(benzyloxy)-6-methoxy-2-((4-methoxybenzyl)amino)quinazolin-4-yl)piperazine-1-carboxylate (32a)

Compound 31a was synthesized in the same way as compound 14 was synthesized. $^1$H NMR (300 MHz, CDCl$_3$) δ 1.5 (s, 9H), 3.56 (d, J=6 Hz, 4H), 3.61 (d, J=6 Hz, 4H), 3.81 (s, 3H), 3.93 (s, 3H), 4.61 (d, J=6 Hz, 2H), 5.25 (s, 2H), 6.86 (s, 1H), 6.89 (s, 1H), 7.01 (s, 2H), 7.30-7.33 (m, 2H), 7.36-7.43 (m, 3H), 7.48-7.51 (m, 2H). EI-HRMS [M]$^+$: Calculated 585.2951. Found: 585.2945.

t-Butyl-4-(7-(benzyloxy)-2-((2-hydroxy-2-methylpropyl)amino)-6-methoxyquinazolin-4-yl)piperazine-1-carboxylate (32b)

Compound 31b was synthesized according to the procedure of compound 14. $^1$H NMR (300 MHz, CDCl$_3$) δ 1.26 (s, 6H), 1.47 (s, 9H), 3.42 (d, J=6 Hz, 2H), 3.53 (t, J=9 Hz, 4H), 3.62 (t, J=9 Hz, 4H), 3.87 (s, 3H), 5.16 (s, 2H), 6.95 (s, 1H), 6.96 (s, 1H), 7.30-7.39 (m, 3H), 7.43-7.46 (m, 2H). EI-HRMS [M]$^+$: Calculated 537.2951. Found: 537.2950.

Example 10

SCHEME:10

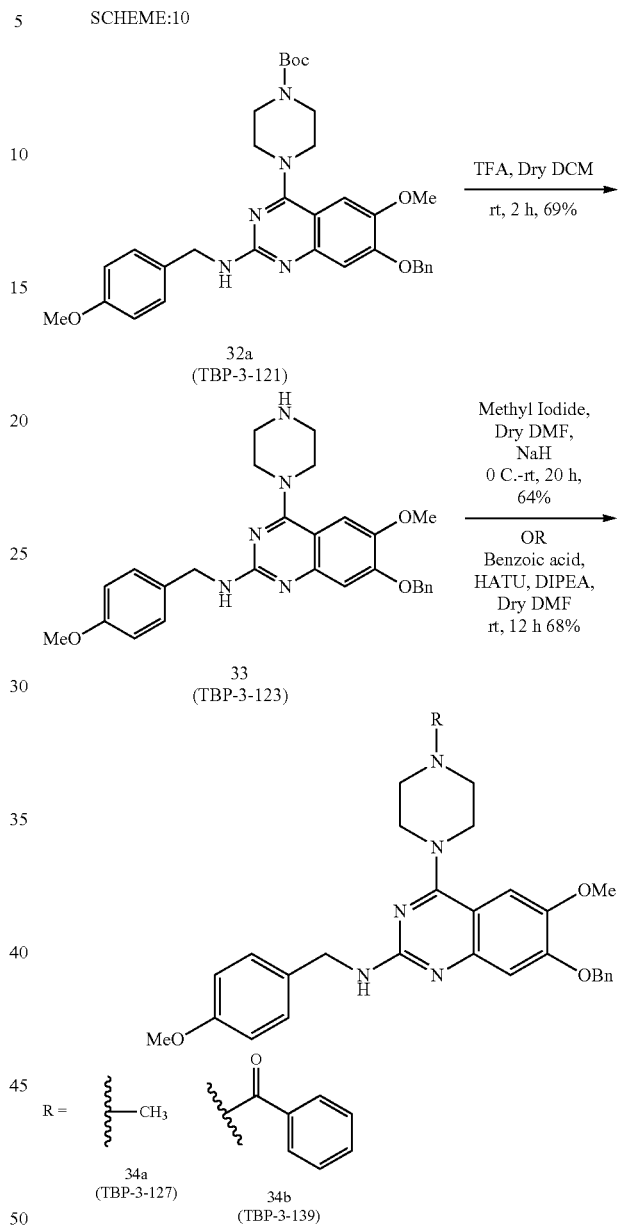

7-(Benzyloxy)-6-methoxy-2-(4-methoxyphenethyl)-4-(piperazin-1-yl)quinazoline (33)

Compound 33 was synthesized in the same way as compound 12 was synthesized. $^1$H NMR (300 MHz, CDCl$_3$) δ 3.60 (t, J=9 Hz, 4H), 3.70 (t, J=9 Hz, 4H), 3.80 (s, 3H), 3.92 (s, 3H), 4.60 (d, J=6 Hz, 2H), 5.24 (s, 2H), 6.85 (s, 1H), 6.88 (s, 1H), 7.02 (d, J=6 Hz, 2H), 7.29-7.43 (m, 5H), 7.49 (d, J=6 Hz, 2H). ESI [M+H]$^+$:486.44.

7-(Benzyloxy)-6-methoxy-2-(4-methoxyphenethyl)-4-(4-methylpiperazin-1-yl)quinazoline (34a)

Compound 34a was synthesized in the same way as described for compound 13a and 13b. $^1$H NMR (300 MHz, CDCl$_3$) δ 2.37 (s, 3H), 2.57 (t, J=9 Hz, 4H), 3.76 (t, J=9 Hz, 4H), 3.80 (s, 3H), 3.91 (s, 3H), 4.60 (d, J=6 Hz, 2H), 5.25 (s, 2H), 6.85 (s, 1H), 6.88 (s, 1H), 7.01-7.05 (m, 2H), 7.29-7.43 (m, 5H), 7.48-7.51 (m, 2H). EI-HRMS [M]$^+$: Calculated 499.2583. Found: 499.2584.

(4-(7-(Benzyloxy)-6-methoxy-2-(4-methoxyphenethyl)quinazolin-4-yl)piperazin-1-yl)(phenyl)methanone (34b)

Compound 33b was synthesized according to the procedure of compound 13c and 13f. $^1$H NMR (300 MHz, CDCl$_3$) δ 2.72 (br. s, 4H), 3.51 (t, J=6 Hz, 2H), 3.80 (br. s, 3H), 3.89-3.94 (m, 5H), 4.61 (d, J=6 Hz, 2H), 5.30 (s, 2H), 6.84 (s, 1H), 6.86 (s, 1H), 6.96 (s, 1H), 7.17 (s, 1H), 7.30 (s, 1H), 7.34-7.40 (m, 3H), 7.44-7.49 (m, 5H), 7.51-7.55 (m, 2H), 8.17-8.20 (m, 1H). ESI [M+H]$^+$:509.38.

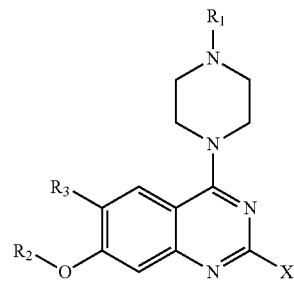

Formula (I)

TABLE 1

Quinazoline with formula (I) composition of the Invention

| ID | X | R1 | R2 | R3 |
|---|---|---|---|---|
| TBP-2-71 | -N(CH$_3$)$_2$ | -C(=O)-O-C(CH$_3$)$_3$ | -H | -O-CH$_3$ |
| TBP-2-169 | -N(CH$_3$)$_2$ | -H | -H | -O-CH$_3$ |
| TBP-2-79 | -N(CH$_3$)$_2$ | -C(=O)-O-C(CH$_3$)$_3$ | -(CH$_2$)$_n$-N(pyrrolidine) | -O-CH$_3$ |
| TBP-2-83 | -N(CH$_3$)$_2$ | -H | -(CH$_2$)$_n$-N(pyrrolidine) | -O-CH$_3$ |
| TBP-2-117 | -N(CH$_3$)$_2$ | -C(=O)-cyclopentyl | -(CH$_2$)$_n$-N(pyrrolidine) | -O-CH$_3$ |
| TBP-2-93 | -N(CH$_3$)$_2$ | -S(=O)$_2$-CH(CH$_3$)$_2$ | -(CH$_2$)$_n$-N(pyrrolidine) | -O-CH$_3$ |
| TBP-2-121 | -N(CH$_3$)$_2$ | -S(=O)$_2$-N(CH$_3$)$_2$ | -(CH$_2$)$_n$-N(pyrrolidine) | -O-CH$_3$ |
| TBP-2-165 | -N(CH$_3$)$_2$ | -C(=O)-O-C(CH$_3$)$_3$ | -(CH$_2$)$_n$-N(morpholine) | -O-CH$_3$ |

TABLE 1-continued

Quinazoline with formula (I) composition of the Invention

| ID | X | R1 | R2 | R3 |
|---|---|---|---|---|
| TBP-2-175 | N(CH₃)₂ | H | -(CH₂)₃-morpholine | -O-CH₃ |
| TBP-2-151 | pyrrolidine | -C(=O)-phenyl | H | -O-CH₃ |
| TBP-2-145 | pyrrolidine | -C(=O)-O-tBu | -(CH₂)₃-pyrrolidine | -O-CH₃ |
| TBP-2-173 | pyrrolidine | -C(=O)-O-tBu | -(CH₂)₃-morpholine | -O-CH₃ |
| TBP-2-179 | pyrrolidine | H | -(CH₂)₃-morpholine | -O-CH₃ |
| TBP-2-185 | pyrrolidine | -S(=O)₂-phenyl | -(CH₂)₃-morpholine | -O-CH₃ |
| TBP-2-191 | pyrrolidine | -C(=O)-O-tBu | -(CH₂)₃-imidazole | -O-CH₃ |
| TBP-2-189 | pyrrolidine | -C(=O)-O-tBu | -(CH₂)₃-(N-methylpiperazine) | -O-CH₃ |
| TBP-1-69 | N-methylpiperazine | -C(=O)-phenyl | -CH₂-phenyl | -O-CH₃ |
| TBP-2-135 | pyrrolidine | -C(=O)-O-tBu | H | -O-CH₃ |
| TBP-2-149 | pyrrolidine | -C(=O)-phenyl | -CH₂-phenyl | -O-CH₃ |
| TBP-3-59 | pyrrolidine | -CH₂-phenyl | -(CH₂)₃-N(CH₃)₂ | -O-CH₃ |

TABLE 1-continued
Quinazoline with formula (I) composition of the Invention
| ID | X | R1 | R2 | R3 |
|---|---|---|---|---|
| TBP-3-71 | 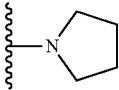 | 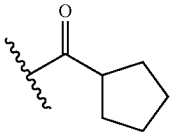 [SMILES: *C(=O)C1CCCC1] | 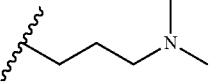 [SMILES: *CCCN(C)C] | 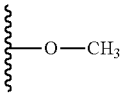 |
| TBP-3-57 | 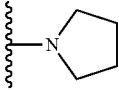 | 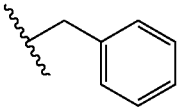 [SMILES: *Cc1ccccc1] | 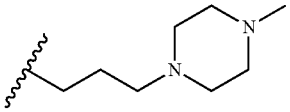 [SMILES: *CCCN1CCN(C)CC1] | 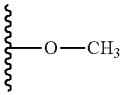 |
| TBP-3-67 | 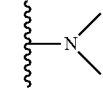 | 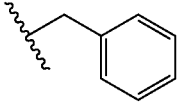 [SMILES: *Cc1ccccc1] | 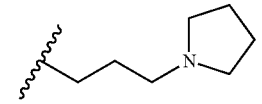 [SMILES: *CCCN1CCCC1] | 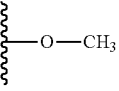 |
| TBP-3-75 | 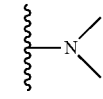 | 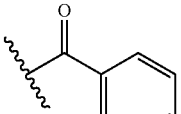 | 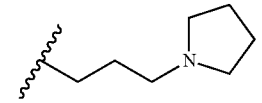 [SMILES: *CCCN1CCCC1] | 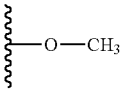 |
| TBP-4-81 | 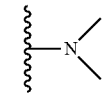 | 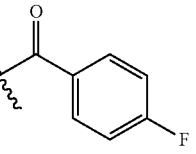 | 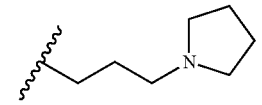 [SMILES: *CCCN1CCCC1] | 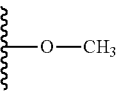 |
| TBP-3-79 | 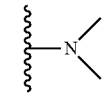 | 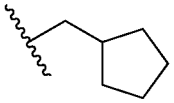 [SMILES: *CC1CCCC1] | 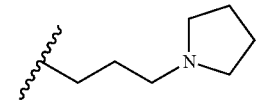 [SMILES: *CCCN1CCCC1] | 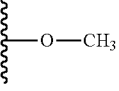 |
| TBP-3-73 | 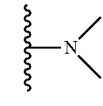 | 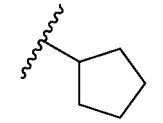 [SMILES: *C1CCCC1] | 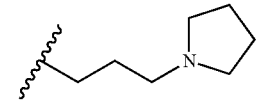 [SMILES: *CCCN1CCCC1] | 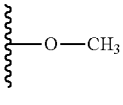 |
| TBP-3-113 | 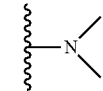 | 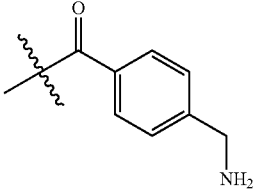 [SMILES: *C(=O)c1ccc(CN)cc1] | 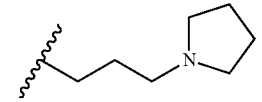 [SMILES: *CCCN1CCCC1] | 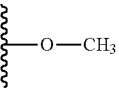 |
| TBP-3-91 | 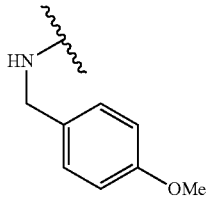 | 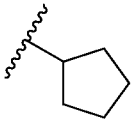 [SMILES: *C1CCCC1] | 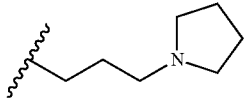 [SMILES: *CCCN1CCCC1] | 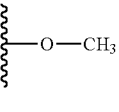 |

TABLE 1-continued
Quinazoline with formula (I) composition of the Invention
| ID | X | R1 | R2 | R3 |
|---|---|---|---|---|
| TBP-3-93 | 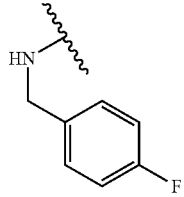 | 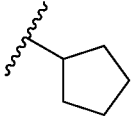 | 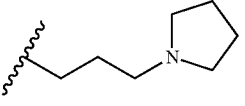 [SMILES: *CCCN1CCCC1] | 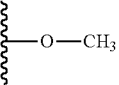 |
| TBP-3-95 | 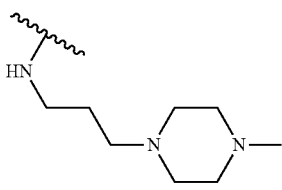 [SMILES: *NCCCN1CCN(C)CC1] | 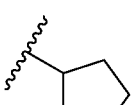 | 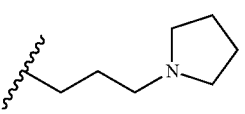 [SMILES: *CCCN1CCCC1] | 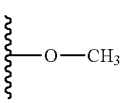 |
| TBP-3-97 | 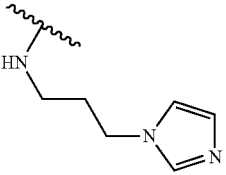 [SMILES: *NCCCn1ccnc1] | 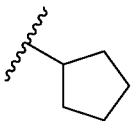 | 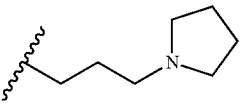 [SMILES: *CCCN1CCCC1] | 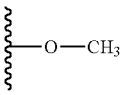 |
| TBP-3-99 | 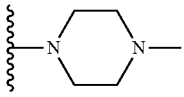 | 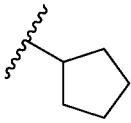 [SMILES: *C1CCCC1] | 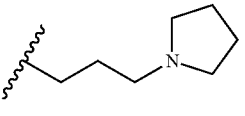 [SMILES: *CCCN1CCCC1] | 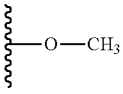 |
| TBP-3-69 | 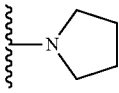 |  | 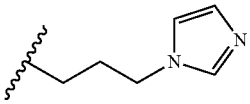 [SMILES: *CCCn1ccnc1] | 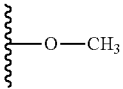 |
| TBP-4-9 |  |  |  | 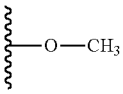 |
| TBP-4-11 |  |  | 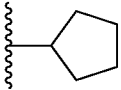 | 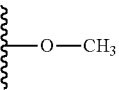 |
| TBP-3-149 |  |  | 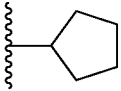 | 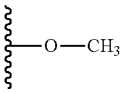 |
| TBP-3-155 |  | 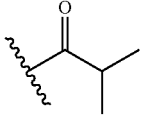 [SMILES: *C(=O)C(C)C] | 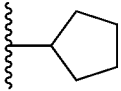 | 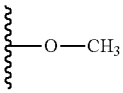 |
| TBP-3-157 |  | 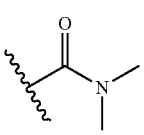 [SMILES: *C(=O)N(C)C] | 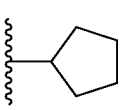 | 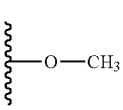 |

TABLE 1-continued

Quinazoline with formula (I) composition of the Invention

| ID | X | R1 | R2 | R3 |
|---|---|---|---|---|
| TBP-3-135 | —N(CH₃)₂ | —C(O)—phenyl | —CH₂—phenyl | —O—CH₃ |
| TBP-3-137 | —N(CH₃)₂ | —S(O)₂—N(CH₃)₂ | —CH₂—phenyl | —O—CH₃ |
| TBP-4-7 | —N(CH₃)₂ | —CH₃ | —CH₂—phenyl | —O—CH₃ |
| TBP-2-159 | —N(CH₃)₂ | —H | —CH₂—phenyl | —O—CH₃ |
| TBP-4-75 | —N(CH₃)₂ | cyclopentyl | —H | —O—CH₃ |
| TBP-4-77 | —N(CH₃)₂ | cyclopentyl | N-methylpiperidin-4-yl | —O—CH₃ |
| TBP-4-79 | —N(CH₃)₂ | cyclopentyl | N-methylpyrrolidin-3-yl | —O—CH₃ |
| TBP-3-121 | —NH—CH₂—(4-methoxyphenyl) | —C(O)—O—C(CH₃)₃ | —CH₂—phenyl | —O—CH₃ |
| TBP-3-123 | —NH—CH₂—(4-methoxyphenyl) | —H | —CH₂—phenyl | —O—CH₃ |
| TBP-3-127 | —NH—CH₂—(4-methoxyphenyl) | —CH₃ | —CH₂—phenyl | —O—CH₃ |

TABLE 1-continued

Quinazoline with formula (I) composition of the Invention

| ID | X | R1 | R2 | R3 |
|---|---|---|---|---|
| TBP-3-139 | HN-CH2-(4-methoxyphenyl) | C(=O)-phenyl (benzoyl) | -CH2-phenyl (benzyl) | -O-CH3 |
| TBP-3-145 | -NH-CH2-C(CH3)2-OH | -C(=O)-O-C(CH3)3 (Boc) | -CH2-phenyl (benzyl) | -O-CH3 |
| TBP-4-65 | -N(CH3)2 | -CH3 | 4-(N-Boc)-piperidinyl | -O-CH3 |
| TBP-4-67 | -N(CH3)2 | -CH3 | 4-piperidinyl (NH) | -O-CH3 |
| TBP-4-69 | -N(CH3)2 | -CH3 | 1-methyl-4-piperidinyl | -O-CH3 |
| TBP-4-71 | -N(CH3)2 | -CH3 | 1-methyl-3-pyrrolidinyl | -O-CH3 |
| TBP-4-73 | -N(CH3)2 | -CH3 | 4-(dimethylamino)phenyl | -O-CH3 |

Example 11

Experimental Procedure for Screening Toll-Like Receptor 9 Antagonistic Activity

To screen the synthesized small molecules based on quinazoline scaffolds for toll-like receptor 9 (TLR9) antagonisms, we designed a medium throughput biological assay based on toll-like receptor 9 activation in primary human immune cells. Among the immune cell subsets circulating in the peripheral blood, TLR9 has significant expression in plasmacytoid dendritic cells (PDCs) and B lymphocytes. Among these two cell subsets, plasmacytoid dendritic cells are capable of producing type I interferons (e.g. IFN-alpha) in response to TLR9 ligands. Type A and type B unmethylated cytosine-guanine rich DNA oligonucleotides (CpG oligonucleotides) are the bona fide ligands for TLR9.

Example 12

We established that IFN-alpha production from human peripheral blood mononuclear cells in response to type A CpG oligonucleotides (CpGA) almost exclusively results from TLR9 triggering on the PDCs (data not shown). Based on this principle we designed our screening assay where we isolated peripheral blood mononuclear cells (PBMCs) from venous blood collected from healthy donors using density gradient centrifugation. Then we cultured the PBMCs at 2-3*10^5 cells/200 ul/well in a 96 well plate. We added the TLR9 agonist CpGA at 1 uM in presence of escalating doses of the synthesized small molecules (0 uM, 0.1 uM, 1 uM, 5 uM, 10 uM and 20 uM). After overnight culture we collected the supernatants from the culture wells and looked for IFN-alpha using enzyme linked immunosorbent assay (ELISA). Molecules having TLR9 antagonistic activity inhibited IFN-alpha production in this screening assay.

Example 13

The structural evolution of the successively synthesized molecules was rationalized using the IFN-alpha inhibition data as depicted in the FIG. 1. A number of compounds with formula (I) were found to be efficient at antagonizing TLR9 activation at nanomolar concentration (FIG. 1).

Example 14

Experimental Procedure for TLR9 Antagonism in Primary Human pDC.

To screen the synthesized small molecules based on quinazoline scaffolds for toll-like receptor 9 antagonism, we designed a medium throughput biological assay based on toll-like receptor 9 activation in plasmacytoid dendritic cells (pDC), which were isolated from PBMCs of healthy donors. pDCs were isolated from PBMCs by magnetic immunoselection using anti-BDCA4 microbeads. The isolated pDCs were then cultured at 3*10^4 cells/100 μl/well in a 96 well plate. We added the TLR9 agonist CpGA at 500 nM in presence of escalating doses of the synthesized small molecules. After overnight culture we collected the supernatants from the culture wells and looked for IFN-alpha using enzyme linked immunosorbent assay (ELISA). Molecules having TLR9 antagonistic activity inhibited IFN-alpha production in this screening assay (FIG. 2).

Example 15

Experimental Procedure for TLR9 Reporter Assay

The synthesized small molecules based on quinazoline scaffolds were screened for TLR9 antagonism using a HEK-Blue-hTLR9 Secreted Alkaline Phosphatase (SEAP) reporter assay. Reporter HEK cell lines expressing human TLR9 along with a NF-κB promoter driven secreted embryonic alkaline phosphatase (SEAP) reporter gene were used. 70,000 cells per well were incubated overnight at 37° C. and 5% $CO_2$ in a 96 well plate in complete DMEM medium supplemented with 100 μg/ml Normocin. After incubation, the TLR9 agonist CpGB was added to the wells at a concentration of 1 μM in presence of escalating doses of the synthesized small molecules and incubated at 37° C. and 5% $CO_2$ for 24 hours. After incubation of the HEK cells, supernatants were collected and 20 μl of supernatant was added to wells containing 200 μl of Quanti-Blue Detection media. After 2 hours of further incubation, OD values were taken at 620 nm in a spectrophotometer. Molecules having TLR9 antagonistic activity inhibited TLR9-mediated NF-kB activation in a dose-dependent manner (FIGS. 3A-3D).

Example 16

Experimental Procedure for Screening for Cytotoxicity of the Identified TLR9 Antagonists MTT assay is a colorimetric assay for assessing cell viability. It is widely used for screening drugs and testing their cytotoxicity. NAD(P)H-dependent cellular oxidoreductase enzymes may, under defined conditions, reflect the number of viable cells present. These enzymes are capable of reducing the tetrazolium dye MTT 3-(4,5dimethylthiazol-2-yl)-2,5-diphenyltetrazolium bromide to its insoluble formazan, which has a purple colour. Viable cells with active metabolism convert MTT into a purple colored formazan product with an absorbance maximum near 570 nm. When cells die, they lose the ability to convert MTT into formazan, thus colour formation serves as a useful and convenient marker of only the viable cells. The exact cellular mechanism of MTT reduction into formazan is not well understood, but likely involves reaction with NADH or similar reducing molecules that transfer electrons to MTT.

Example 17

To check cytotoxicity of the synthesized TLR9 antagonists, HepG2 (a hepatic epithelial cell line) and SW480 (an intestinal mucosal epithelial cell line) cells were cultured in DMEM Complete media in 96 well plates at density of 30,000 cells per well, making a final volume of 100 μl/well. Treatment with different concentrations (0.1, 0.5, 1, 10, 20 and 100 μM) of different candidate small molecule antagonists was added. Plates were incubated for 24 hours at 37 deg C. and 5% CO2 in incubator. After 24 hrs 50 μl of MTT (5 mg/ml) was added to each well and further incubated for 1 to 4 hours at 37° C. Then 100 μl of DMSO was added to each well and properly mixed to ensure complete solubilisation of formazan crystals. Then absorbance was measured at 570 nm using an ELISA plate reader. None of the identified TLR9 antagonists showed considerable cytotoxicity at concentrations below 100 μM on this assay (FIG. 4).

Advantages of the Invention

The main advantages of the present invention are:
The synthesized new compounds with general formula (I) of the present invention have several advantages.
1. The invention provides small molecules with general formula (I) which can effect immune stimulation via TLR9 antagonism.
2. The invention provides small molecules with general formula (I) which can inhibit immune stimulation via TLR9 antagonism.
3. The invention provides a medium throughput biological assays results involving human peripheral blood mononuclear cells, isolated human primary pDCs and reporter assay using transfected TLR9 cells to screen compounds with formula (I). All the three assays system was standardized and the results from all three assay systems can be correlated.
4. This invention provides compounds with formula (I) which can be used in a number of clinical contexts of autoreactive inflammation, including as pharmaceutical agents and methods for treating conditions involving unwanted immune activity in response to a suitable TLR ligand or TLR signalling agonist.

We claim:
1. A compound of general formula 1,
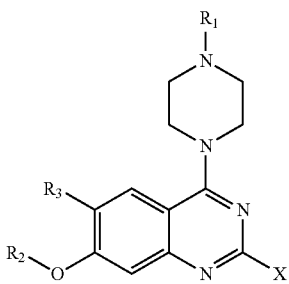
General Formula 1
wherein
X is independently selected from the group consisting of:
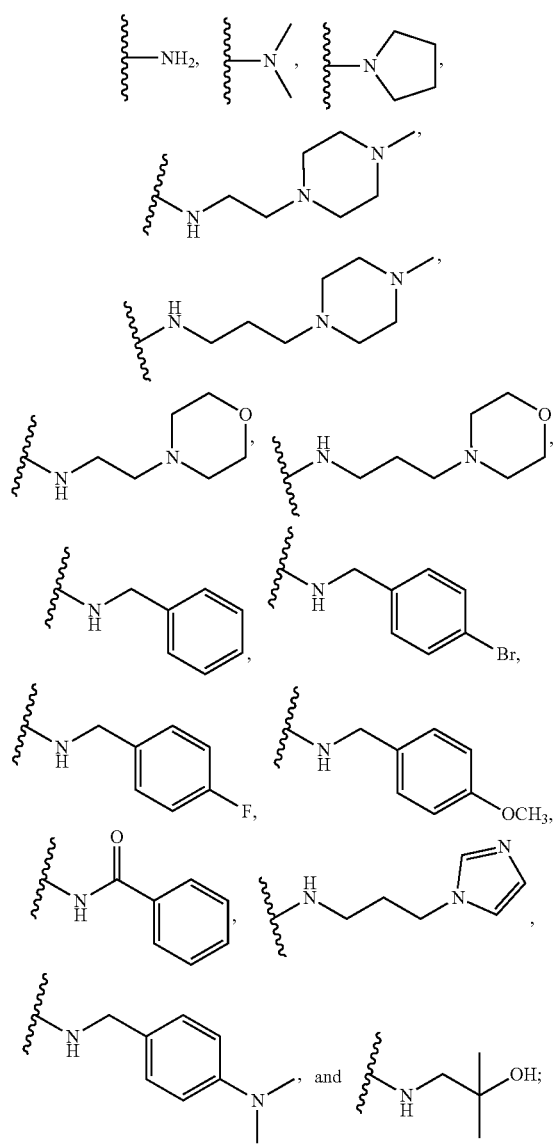
wherein R₁ is independently selected from the group consisting of:
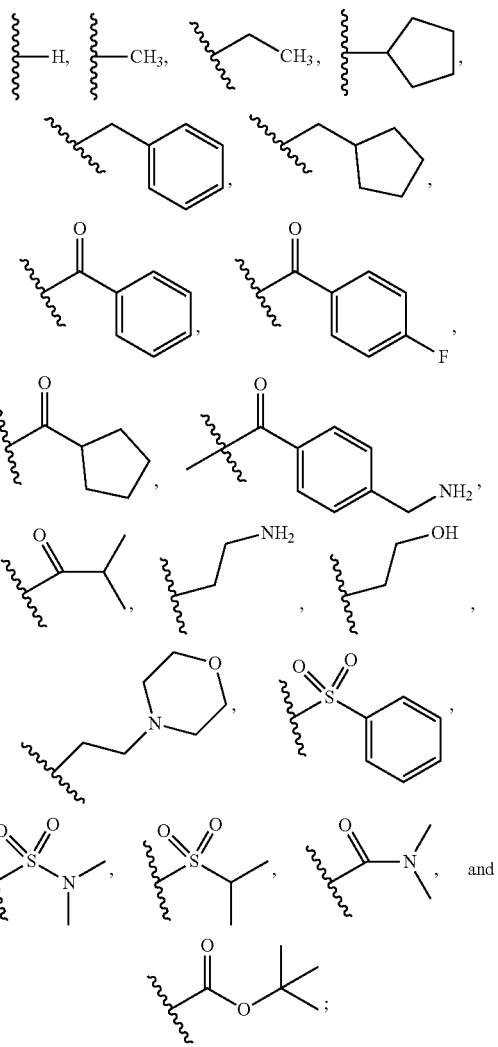
wherein R₂ is independently selected from the group consisting of:
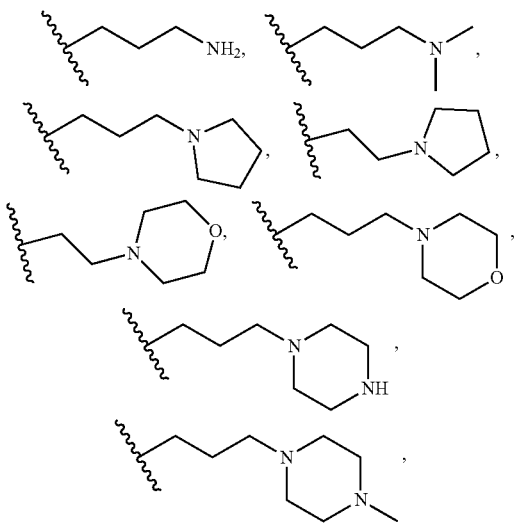

wherein $R_3$ is independently selected from the group consisting of hydrogen, —OH and $OCH_3$ groups.

2. The compound of general formula 1 as claimed in claim 1, wherein the compound is selected from the group consisting of:

4-(4-(Isopropylsulfonyl)piperazin-1-yl)-6-methoxy-N,N-dimethyl-7-(3-(pyrrolidin-1-yl)propoxy)quinazolin-2-amine 13a(TBP-2-93);
4-(4-(Dimethylamino)-6-methoxy-7-(3-(pyrrolidin-1yl)propoxy)quinazolin-4-yl)-N,N-dimethylpiperazin-1-sulfonamide 13b(TBP-2-121);
Cyclopentyl(4-(2-(dimethylamino)-6-methoxy-7-(3-(pyrrolidin-1yl)propoxy)quinazolin-4-yl)piperazine-1yl)methanone 13c(TBP-2-117);
4-(4-(Cyclopentylmethyl)piperazin-1-yl)-6-methoxy-N,N-dimethyl-7-(3-(pyrrolidin-1yl)propoxy)quinazolin-2-amine 13d(TBP-3-79);
4-(4-(Cyclopentylpiperazin-1-yl)-6-methoxy-N,N-dimethyl-7-(3-(pyrrolidin-1yl)propoxy)quinazolin-2-amine 13e(TBP-3-73);
(4-(2-(Dimethylamino)-6-methoxy-7-(3-(pyrrolidin-1-yl)propoxy)quinazoline-4-yl)piperazin-1-yl)(phenyl)methanone 13f(TBP-3-75);
4-(4-Benzylpiperazin-1-yl)-6-methoxy-N,N-dimethyl-7-(3-(pyrrolidin-1-yl)propoxy)quinazolin-2-amine 13g (TBP-3-67);
(4-(Aminomethyl)phenyl)(4-(2-(dimethylamino)-6-methoxy-7-(3-(pyrrolidin-1-yl)propoxy)quinazolin-4-yl)piperazin-1-yl)methanone 13h (TBP-3-113);
2-(4-(2-(dimethylamino)-6-methoxy-7-(3-(pyrrolidin-1-yl)propoxy)quinazolin-4-yl)piperazin-1-yl)-1-(4-fluorophenyl)ethanone 13j (TBP-4-81);
t-Butyl-4-(6-methoxy-7-(3-morpholinpropoxy)-2-(pyrrolidin-1-yl)quinazoline-4-yl)piperazine-1-carboxylate 17a(TBP-2-173);
t-Butyl-4-(6-methoxy-7-(3-(4-methylpiperazin-1-yl)propoxy)-2-(pyrrolidin-1-yl)quinazoline-4-yl)piperazine-1-carboxylate 17b(TBP-2-189);
t-Butyl-4-(7-(3-(1H-imidazol-1-yl)propoxy)-6-methoxy-2-(pyrrolidin-1-yl)quinazolin-4-yl)piperazine-1-carboxylate 17c(TBP-2-191);
t-Butyl-4-(7-(3-(1H-imidazol-1-yl)propoxy)-6-methoxy-2-(pyrrolidin-1-yl)quinazoline-4-yl)piperazine-1-carboxylate 17d(TBP-3-47);
t-Butyl-4-(6-methoxy-2-(pyrrolidin-1-yl)-7-(3-(pyrrolidin-1-yl)propoxy)quinazolin-4-yl)piperazine-1-carboxylate 17e(TBP-2-145);
4-(3-(6-Methoxy-4-(piperazin-1-yl)-2-(pyrrolidin-1-yl)quinazolin-7-yloxy)propyl)morpholine 18a(TBP-2-179);
7-(3-(1H-Imidazol-1-yl)propoxy)-6-methoxy-4-(piperazin-1-yl)-2-(pyrrolidin-1-yl)quinazoline 18b(TBP-3-69);
3-((6-Methoxy-4-(piperazin-1-yl)-2-(pyrrolidin-1-yl)quinazolin-7-yl)oxy)-N,N-dimethylpropan-1-amine 18c (TBP-3-49);
4-(3-(6-Methoxy-4-(4-(phenylsulfonyl)piperazin-1-yl)-2-(pyrrolidin-1-yl)quinazolin-7-yloxy)propyl)morpholine 19(TBP-2-185);
4-(4-Benzylpiperazin-1-yl)-6-methoxy-7-(3-(4-methylpiperazin-1-yl)propoxy)-2-(pyrrolidin-1-yl)quinazoline 20(TBP-3-57);
3-(4-(4-Benzylpiperazin-1-yl)-6-methoxy-2-(pyrrolidin-1-yl)quinazolin-7-yloxy)-N,N-dimethylpropan-1-amine 21a(TBP-3-59);
(4-(7-(3-(Dimethylamino)propoxy)-6-methoxy-2-(pyrrolidin-1-yl)quinazolin-4-yl)piperazin-1-yl)(phenyl)methanone 21b(TBP-3-71);
4-(4-Cyclopentylpiperazin-1-yl)-6-methoxy-N-(4-methoxybenzyl)-7-(3-(pyrrolidin-1-yl)propoxy)quinazolin-2-amine 25a(TBP-3-91);
4-(4-Cyclopentylpiperazin-1-yl)-N-(4-fluorobenzyl)-6-methoxy-7-(3-(pyrrolidin-1-yl)propoxy)quinazolin-2-amine 25b(TBP-3-93);
4-(4-Cyclopentylpiperazin-1-yl)-6-methoxy-N-(3-(4-methylpiperazin-1-yl)propyl)-7-(3-(pyrrolidin-1-yl)propoxy)quinazolin-2-amine 25c(TBP-3-95);
N-(3-(1H-Imidazol-1-yl)propyl)-4-(4-cyclopentylpiperazin-1-yl)-6-methoxy-7-(3-(pyrrolidin-1-yl)propoxy)quinazolin-2-amine 25d(TBP-3-97);
7-(Cyclopentyloxy)-6-methoxy-N,N-dimethyl-4-(piperazin-1-yl)quinazolin-2-amine 27 (TBP-3-149);
7-(Cyclopentyloxy)-6-methoxy-N,N-dimethyl-4-(4-methylpiperazin-1-yl)quinazolin-2-amine 28a (TBP-4-11);
1-(4-(7-(Cyclopentyloxy)-2-(dimethylamino)-6-methoxyquinazolin-4-yl)piperazin-1-yl)-2-methylpropan-1-one 28b (TBP-3-155);
4-(7-(Cyclopentyloxy)-2-(dimethylamino)-6-methoxyquinazolin-4-yl)-N,N-dimethylpiperazine-1-carboxamide 28c (TBP-3-157);
6-methoxy-N,N-dimethyl-4-(4-methylpiperazin-1-yl)-7-(piperidin-4-yloxy)quinazolin-2-amine 28d (TBP-4-67);
6-methoxy-N,N-dimethyl-4-(4-methylpiperazin-1-yl)-'7-((1-methylpiperidin-4-yl)oxy)quinazolin-2-amine 28e (TBP-4-69);
6-methoxy-N,N-dimethyl-4-(4-methylpiperazin-1-yl)-7-((1-methylpyrrolidin-3-yl)oxy)quinazolin-2-amine 28f (TBP-4-71);
4-(4-cyclopentylpiperazin-1-yl)-6-methoxy-N,N-dimethyl-7-(1-methylpiperidin-4-yloxy)quinazolin-2-amine 28h (TBP-4-77);

4-(4-cyclopentylpiperazin-1-yl)-6-methoxy-N,N-dimethyl-7-(1-methylpyrrolidin-3-yloxy)quinazolin-2-amine 28i (TBP-4-79);

7-(Benzyloxy)-6-methoxy-N,N-dimethyl-4-(piperazin-1-yl)quinazolin-2-amine 29a (TBP-2-159);

(4-(7-(Benzyloxy)-2-(dimethylamino)-6-methoxyquinazolin-4-yl)piperazin-1-yl)(phenyl)methanone 30a (TBP-3-135);

4-(7-(Benzyloxy)-2-(dimethylamino)-6-methoxyquinazolin-4-yl)-N,N-dimethylpiperazine-1-sulfonamide 30b (TBP-3-137);

7-(Benzyloxy)-6-methoxy-4-(piperazin-1-yl)-2-(pyrrolidin-1-yl)quinazoline 30c (TBP-2-149);

(4-(7-(Benzyloxy)-6-methoxy-2-(pyrrolidin-1-yl)quinazolin-4-yl)piperazin-1-yl)(phenyl)methanone 31 (TBP-2-151);

t-Butyl-4-(7-(benzyloxy)-6-methoxy-2-(4-methoxybenzyl)amino)quinazolin-4-yl)piperazine-1-carboxylate 32a (TBP-3-121);

t-Butyl-4-(7-(benzyloxy)-2-(2-hydroxy-2-methylpropyl)amino)-6-methoxyquinazolin-4-yl)piperazine-1-carboxylate 32b (TBP-3-145);

7-(Benzyloxy)-6-methoxy-2-(4-methoxyphenethyl)-4-(piperazin-1-yl)quinazoline 33 (TBP-3-123);

7-(Benzyloxy)-6-methoxy-2-(4-methoxyphenethyl)-4-(4-methylpiperazin-1-yl)quinazoline 34a (TBP-3-127);

(4-(7-(Benzyloxy)-6-methoxy-2-(4-methoxyphenethyl)quinazolin-4-yl)piperazin-1-yl)(phenyl)methanone 34b (TBP-3-139);

tert-butyl 4-(2-(dimethylamino)-6-methoxy-7-(3-morpholinopropoxy)quinazolin-4-yl)piperazine-1-carboxylate (TBP-2-165); and tert-butyl 4-(2-(dimethylamino)-6-methoxy-7-(3-(pyrrolidin-1-yl)propoxy)quinazolin-4-yl)piperazine-1-carboxylate 11 (TBP-2-79).

3. The compound of general formula 1 as claimed in claim 1, wherein the compound is selected from the group consisting of:

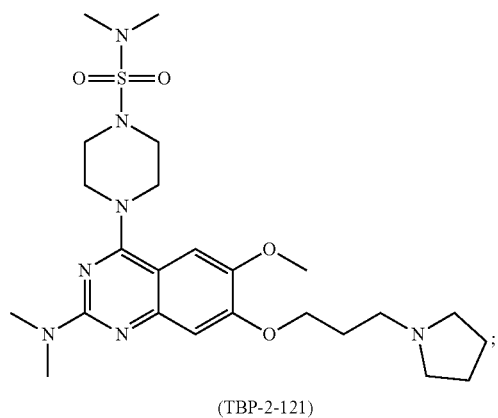

(TBP-2-121)

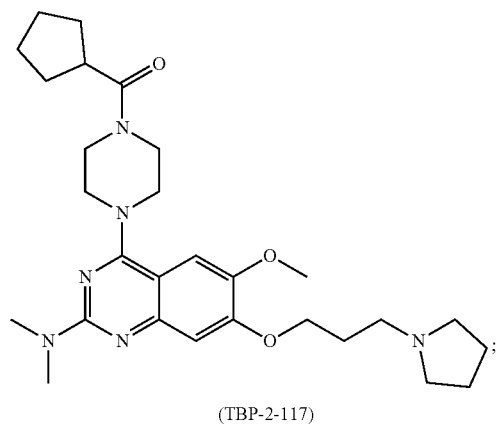

(TBP-2-117)

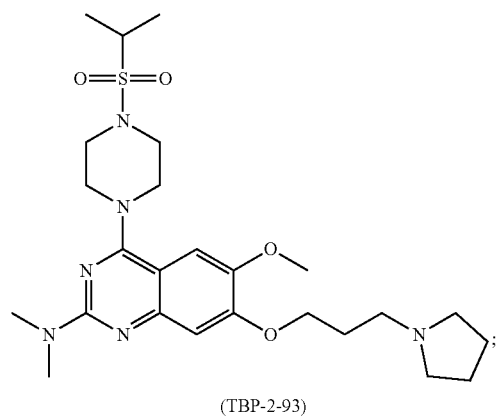

(TBP-2-93)

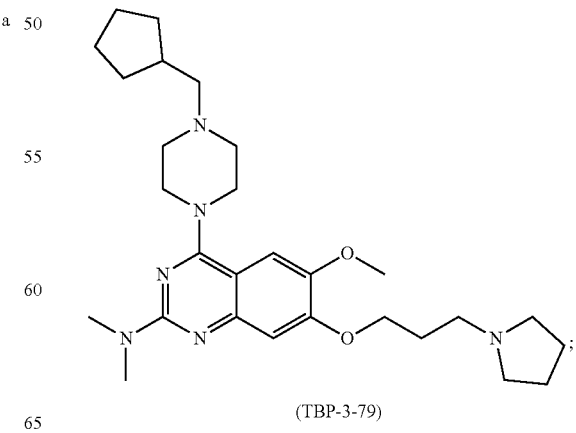

(TBP-3-79)

-continued
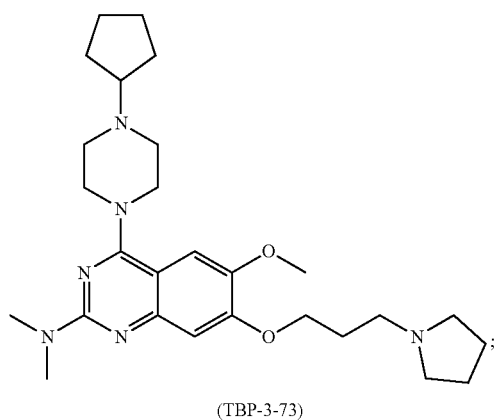
(TBP-3-73)
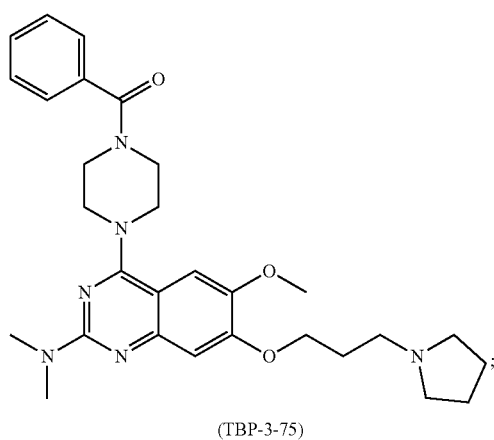
(TBP-3-75)
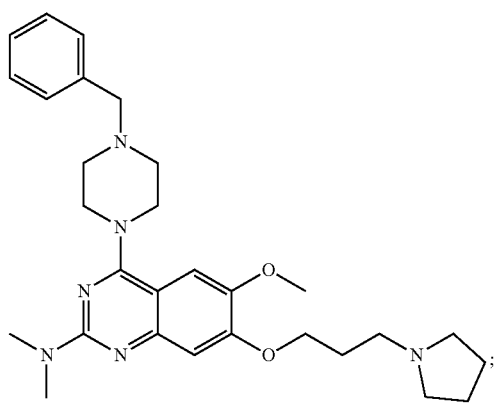
(TBP-3-67)
-continued
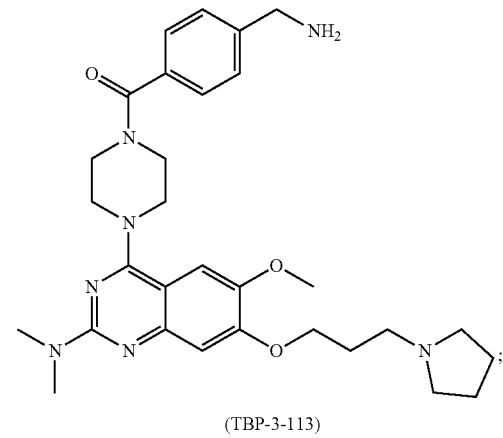
(TBP-3-113)
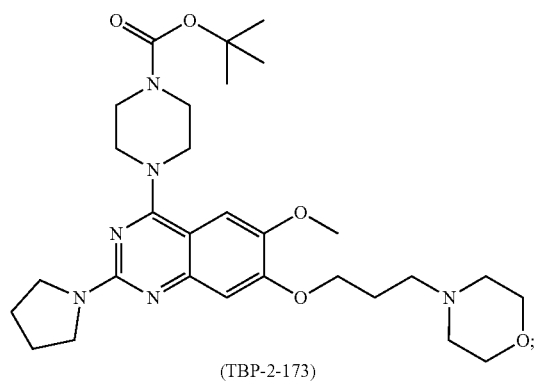
(TBP-2-173)
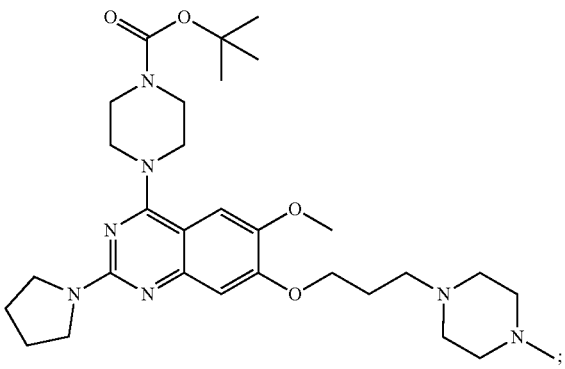
(TBP-2-189)

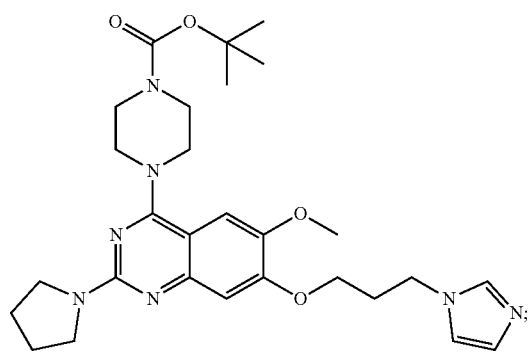
(TBP-2-191)
17c
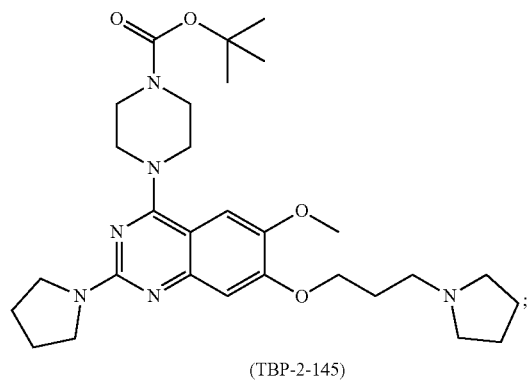
(TBP-3-47)
17d
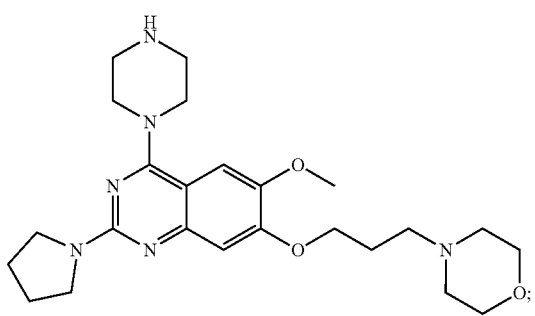
(TBP-2-145)
17e
18a
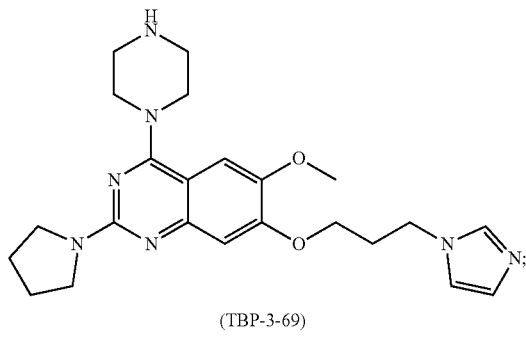
(TBP-3-69)
18b
(TBP-3-49)
18c
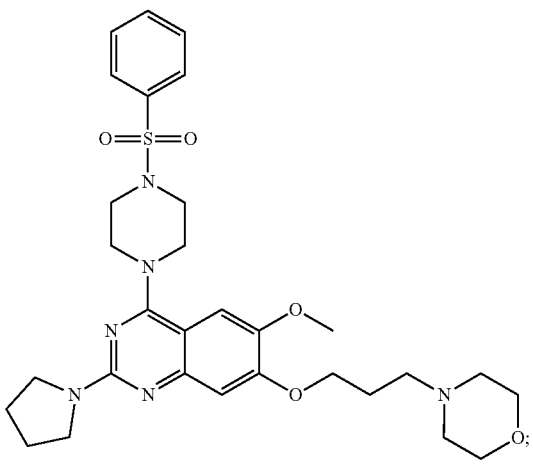
(TBP-2-185)
19

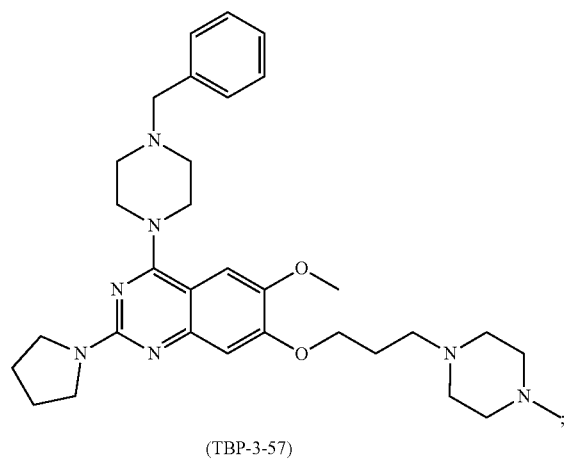
(TBP-3-57)
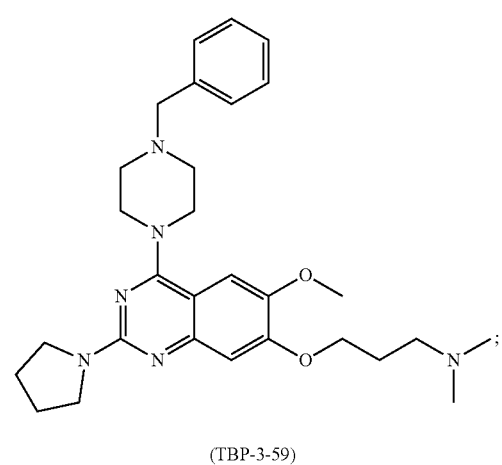
(TBP-3-59)
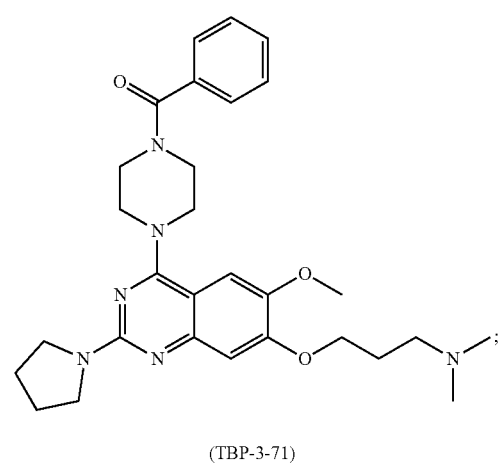
(TBP-3-71)
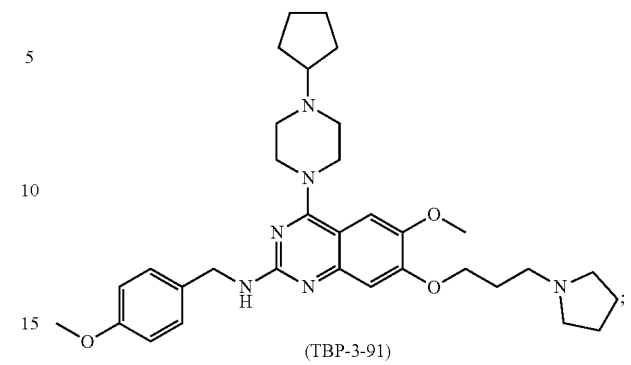
(TBP-3-91)
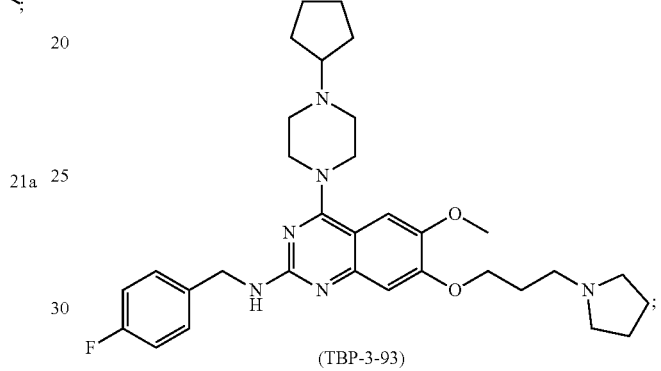
(TBP-3-93)
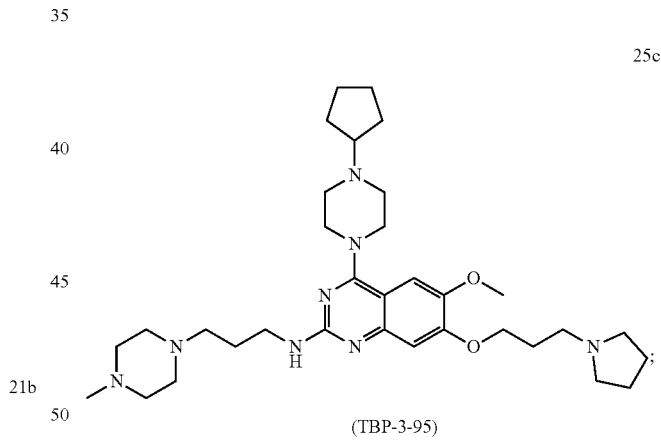
(TBP-3-95)
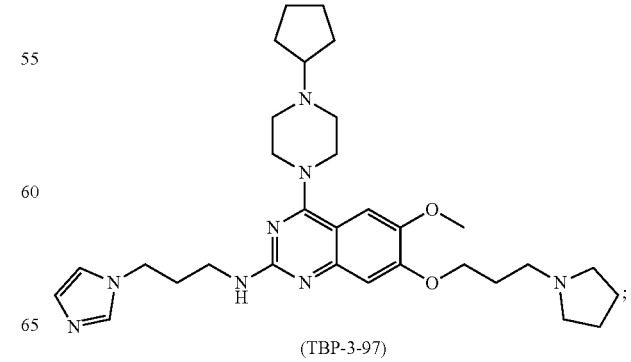
(TBP-3-97)

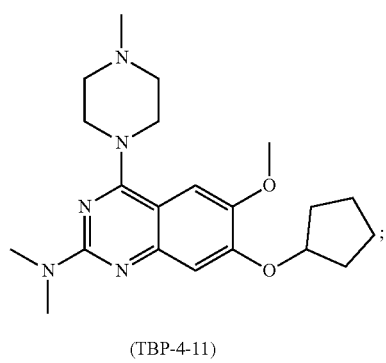
(TBP-4-11)
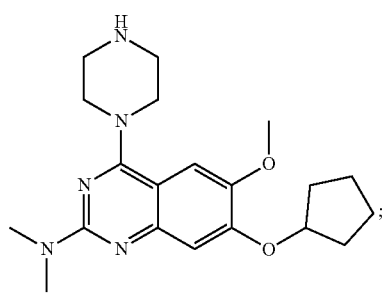
(TBP-3-149)
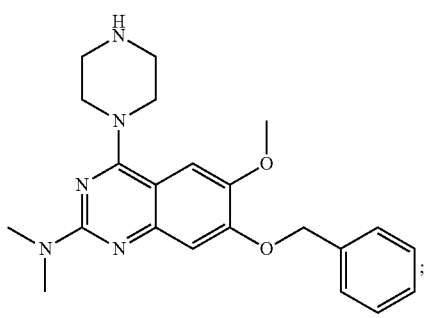
(TBP-2-159)
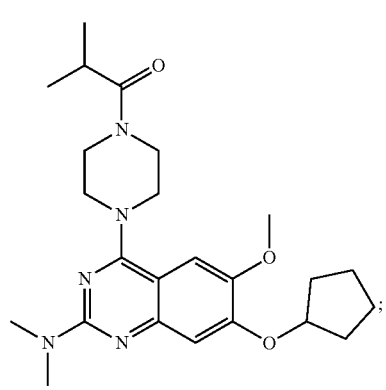
(TBP-3-155)
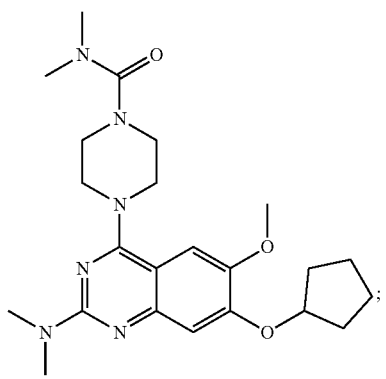
(TBP-3-157)
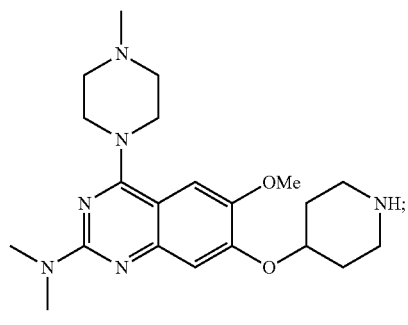
(TBP-4-67)
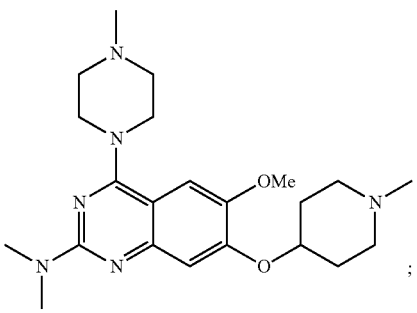
(TBP-4-69)
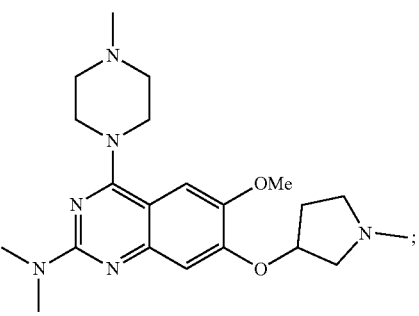
(TBP-4-71)

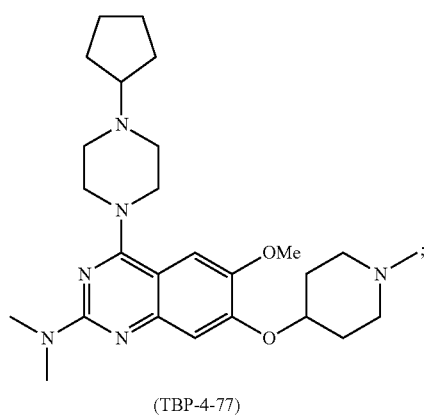
(TBP-4-77) 28h
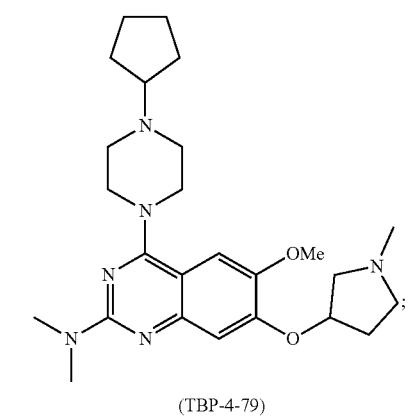
(TBP-4-79) 28i
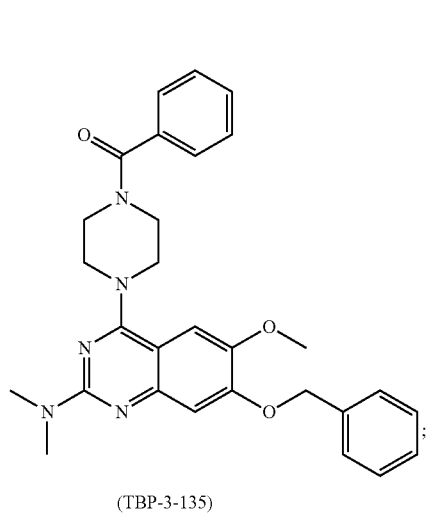
(TBP-3-135) 30a
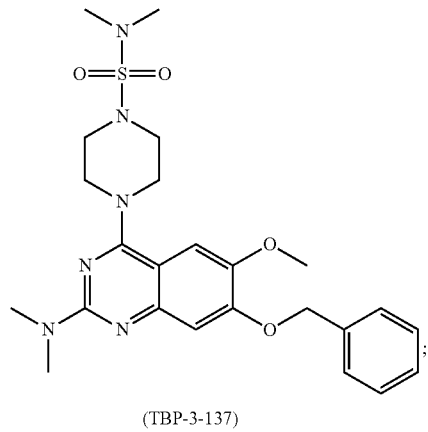
(TBP-3-137) 30b
(TBP-2-149) 30c
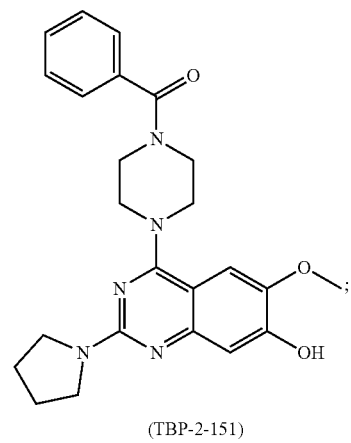
(TBP-2-151) 31

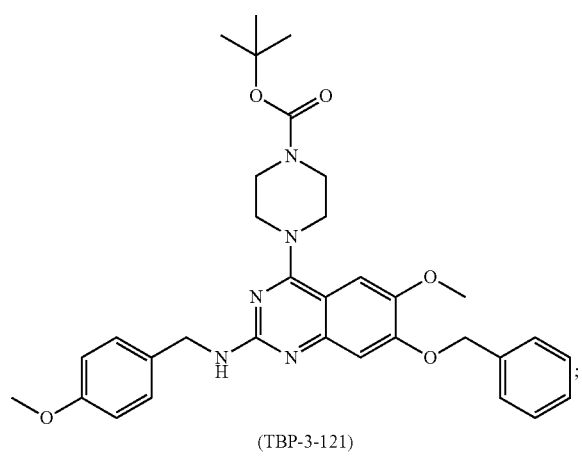
(TBP-3-121)
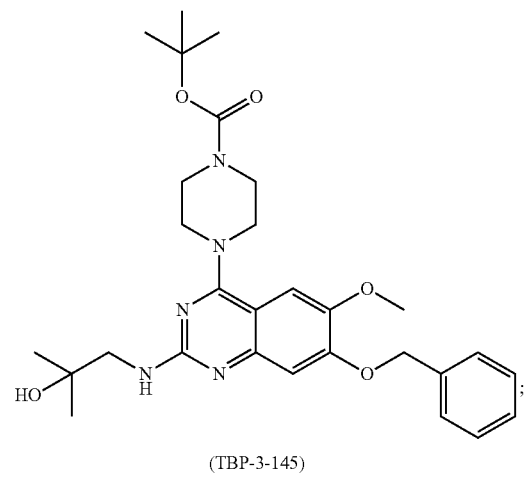
(TBP-3-145)
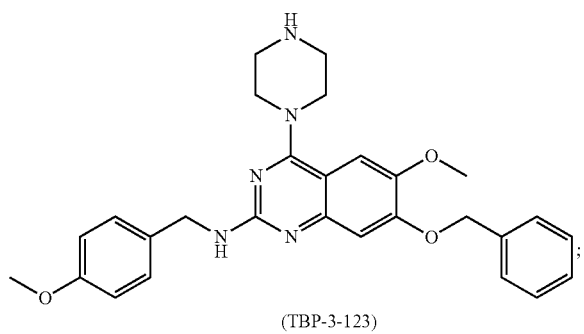
(TBP-3-123)
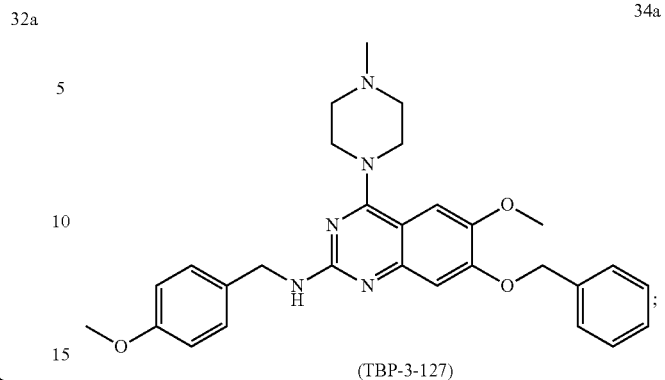
(TBP-3-127)
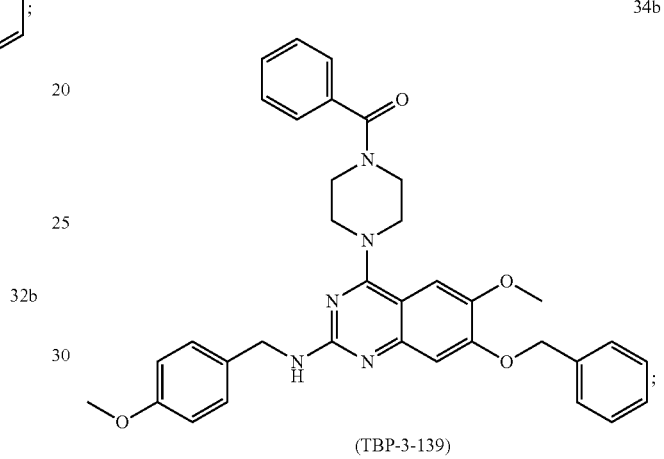
(TBP-3-139)
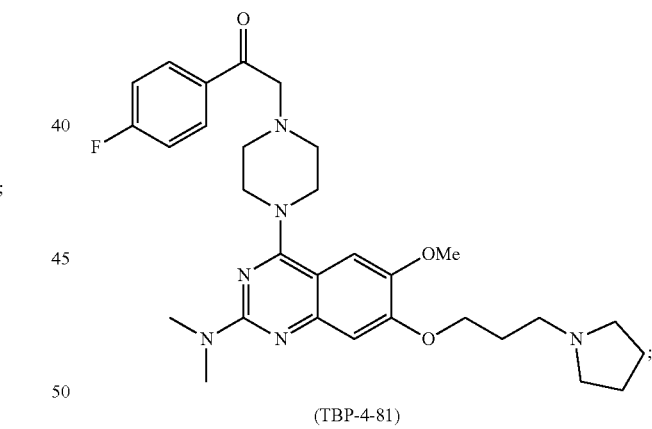
(TBP-4-81)
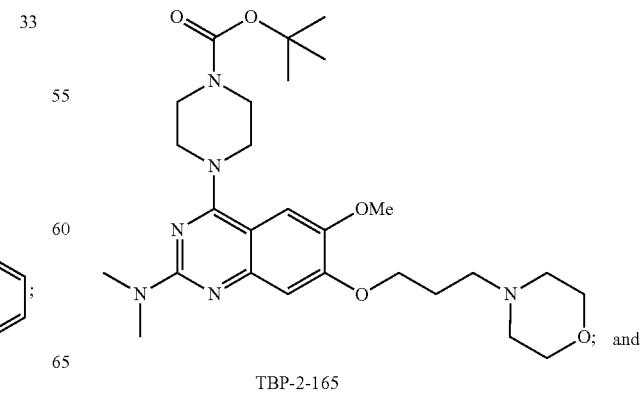
TBP-2-165

4. A process for preparation of the compound of general formula 1 as claimed in claim 1, the method comprising:
   a. reacting compound 6 with Boc-piperazine to obtain compound 7
   b. reacting compound 7 obtained in (a) with amine to obtain compound of formula 8 or 14 or 32;
   c. reacting compound 8 or 14 or 32 of (b) either with hydrogen in presence of Pd/C to obtain compound of 9 or 15 or reacting with TFA to obtain compound 29a or 29b or 33

29a
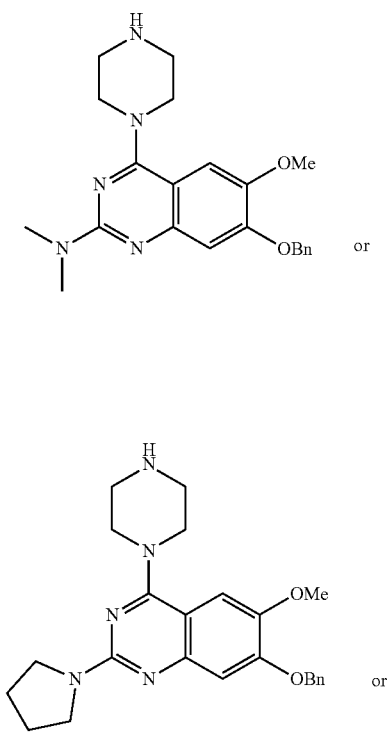
or
29b
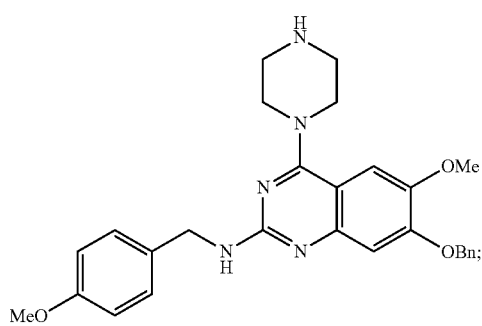
or
33
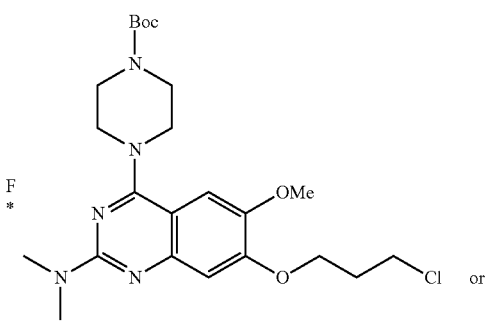
d. reacting compound 9 or 15 of (c) either with 1-chloro-3-bromopropane or bromocyclopentane to obtain compound 10 or 26 or 16
10
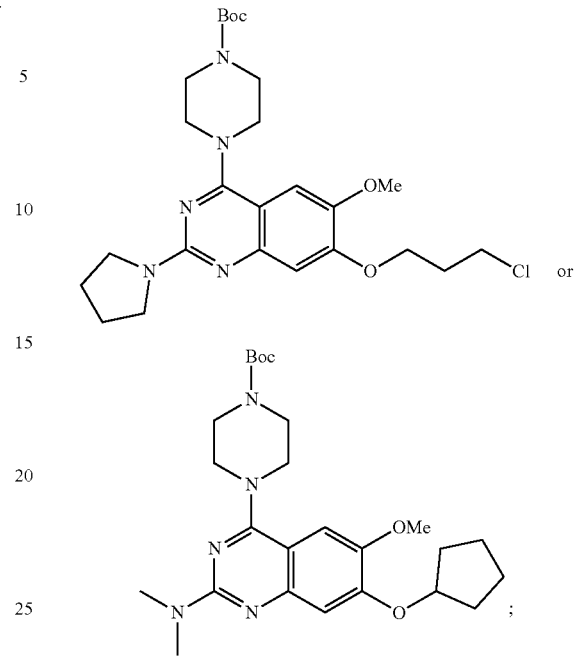
16
26
e. reacting compound 10 or 16 of (d) with amine to obtain compound 11 or 17
11
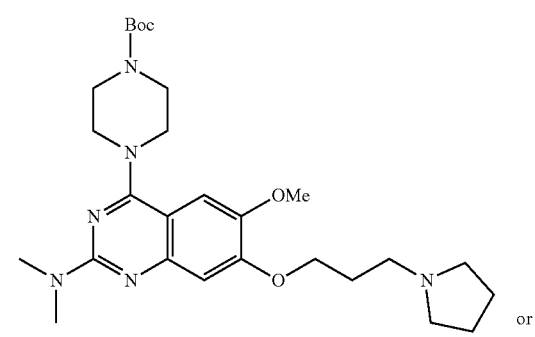
17
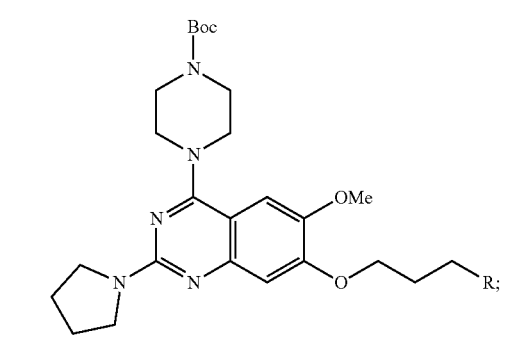
f. reacting compound 11 or 17 of (e) or compound 26 of (d) or compound 14 of (b) with TFA to obtain 12 or 18 or 27

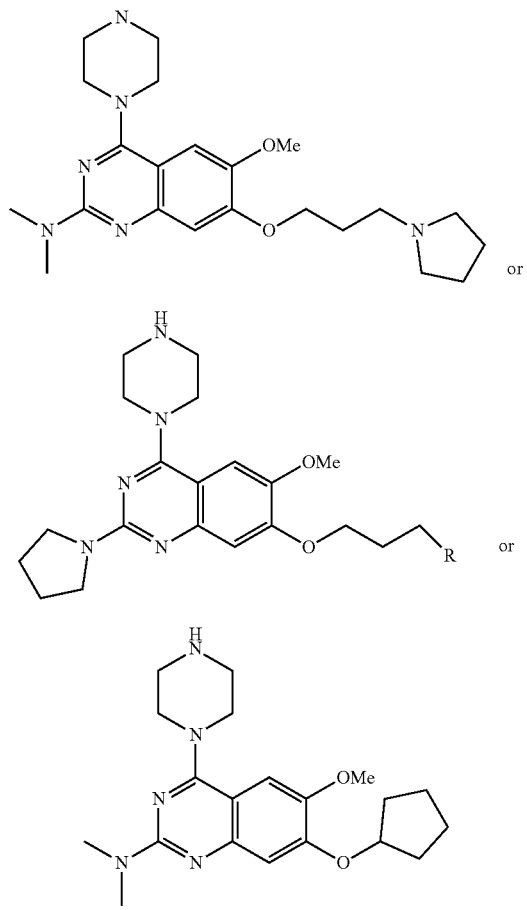

12 or

18

27 g. reacting compound 12 obtained in (f) or 29a or 29b of (c) with sulphonyl chloride, alkyl or aryl carboxylic acid or alkyl halide or aldehyde or reacting compound 33 of (c) with alkyl halide or benzoic acid to obtain the compound of general formula 1.

5. The process as claimed in claim 4, further comprising reacting compound 27 of (f) with alkyl halide or acid chloride to obtain the compound of general formula 1 or compound 31

31

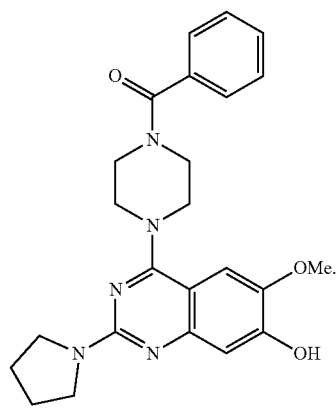

6. The process as claimed in claim 5, wherein compound 31 is further reacted with hydrogen in presence of Pd/C to obtain the compound of general formula 1.

7. The process as claimed in claim 4, further comprising:
(i) reacting compound 6 with N-cyclopentylpiperazine or N-methyl piperazine followed by dimethyl amine to obtain an intermediate;
(ii) reacting the intermediate of (i) with hydrogen in presence of Pd/C to obtain compound 22 or 9b or 9c;

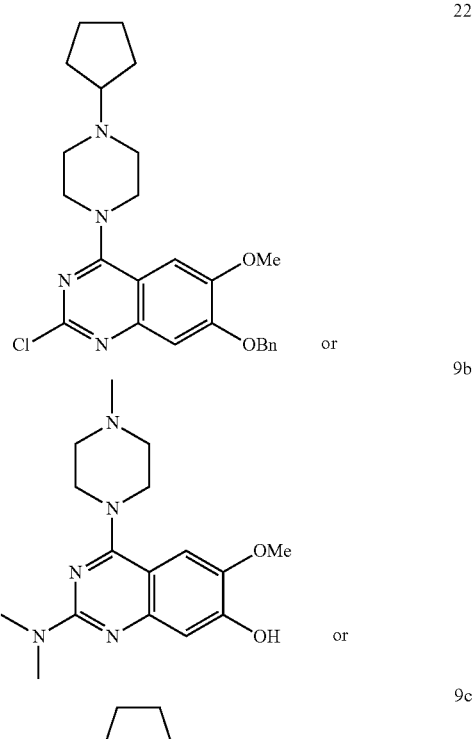

22 or

9b or

9c and
(iii) reacting compound 22, 9b or 9c of (ii) with 1-(3-chloropropyl)pyrrolidine or bromamine or 4-hydroxy amine to obtain the compound of general formula 1.

8. The process as claimed in claim 4, wherein the amine of (b) is selected from the group consisting of:

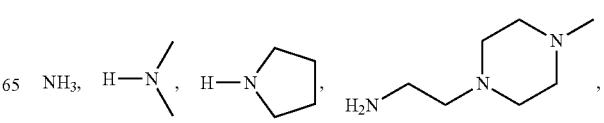

-continued

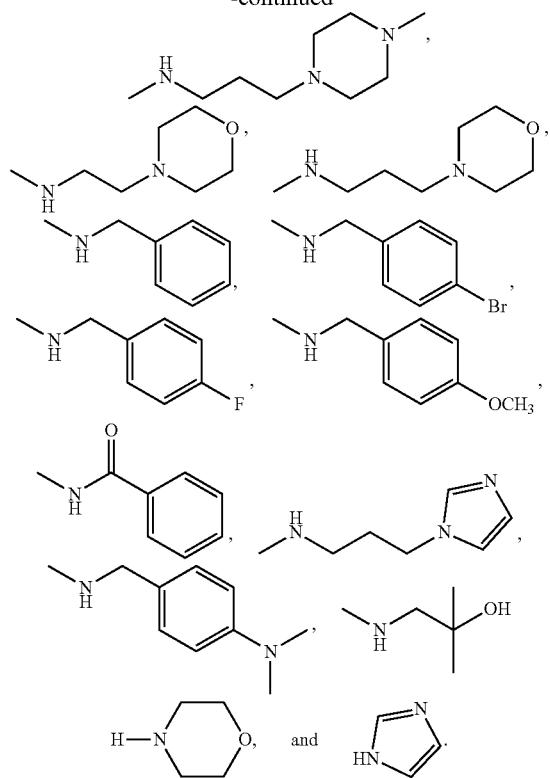

9. The process as claimed in claim 4, wherein the sulphonyl chloride is selected from the group consisting of:

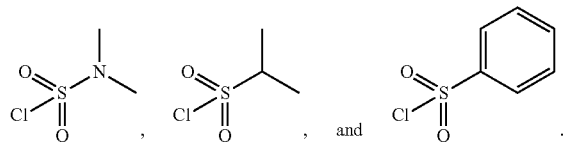

10. The process as claimed in claim 4, wherein the alkyl or aryl carboxylic acid or acid chloride is selected from the group consisting of:

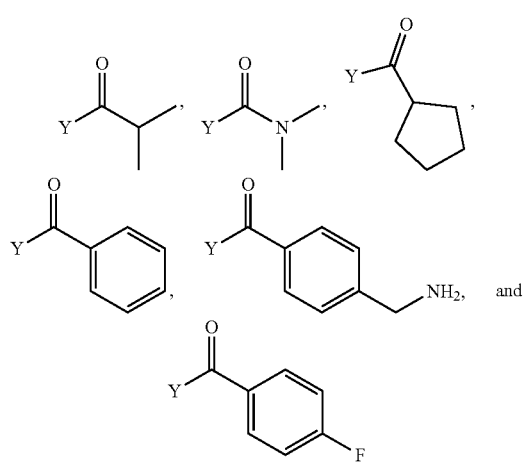

wherein Y=OH, or Cl.

11. The process as claimed in claim 4, wherein the alkyl halide is selected from the group consisting of:

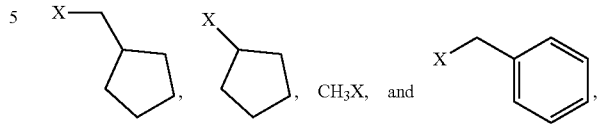

wherein X=halogen.

12. The process as claimed in claim 4, wherein the alkyl or aryl aldehyde is selected from the group consisting of:

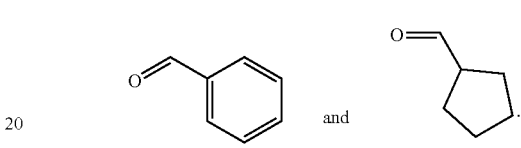

13. The compound as claimed in claim 1, wherein the compound is in free form or in acceptable salt form.

14. A method of inhibiting toll-like receptor mediated signaling comprising contacting the compound of general formula 1 as claimed in claim 1 with TLR9.

15. The compound of formula (I) as claimed in claim 1, wherein the compound of formula 1 inhibits immune stimulation via toll-like receptor 9 (TLR9) antagonism.

16. A pharmaceutical composition comprising the compound of general formula 1 as claimed in claim 1.

17. The process as claimed in claim 4, wherein the amine of (e) is selected from the group consisting of:

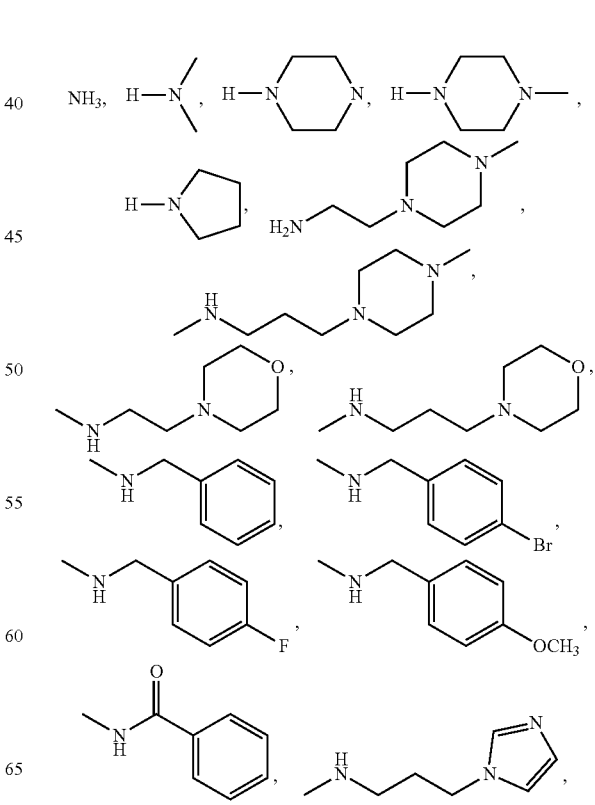

-continued
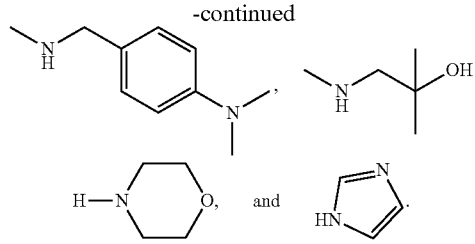
* * * * *